US009752130B2

(12) United States Patent
Spangenberg et al.

(10) Patent No.: US 9,752,130 B2
(45) Date of Patent: Sep. 5, 2017

(54) CHALCONE SYNTHASE DIHYRDOFLAVONOL 4-REDUCTASE AND LEUCOANTHOCYANIDINE REDUCTASE FROM CLOVER, MEDIC RYEGRASS OR FESCUE

(75) Inventors: German Spangenberg, Bundoora (AU); Michael Emmerling, Greensborough (AU); Jason Simmonds, South Morang (AU); Amanda Winkworth, North Coburg (AU); Stephen Panter, Bundoora (AU)

(73) Assignees: Agriculture Victoria Services PTY LTD, Attwood, Victoria (AU); AgResearch Limited, Hamilton (NZ)

( * ) Notice: Subject to any disclaimer, the term of this patent is extended or adjusted under 35 U.S.C. 154(b) by 663 days.

(21) Appl. No.: 13/311,898

(22) Filed: Dec. 6, 2011

(65) Prior Publication Data
US 2012/0131695 A1 May 24, 2012

Related U.S. Application Data

(62) Division of application No. 10/552,857, filed as application No. PCT/AU2004/000494 on Apr. 14, 2004, now Pat. No. 8,093,451.

(30) Foreign Application Priority Data

Apr. 14, 2003 (AU) ................................ 2003901797
Aug. 14, 2003 (AU) ................................ 2003904369

(51) Int. Cl.
A01H 1/00 (2006.01)
C12N 15/82 (2006.01)
C12N 9/06 (2006.01)
C12N 9/02 (2006.01)
C12N 9/04 (2006.01)
C12N 9/10 (2006.01)

(52) U.S. Cl.
CPC ......... C12N 9/0093 (2013.01); C12N 9/0006 (2013.01); C12N 9/0071 (2013.01); C12N 9/1037 (2013.01); C12N 15/825 (2013.01); C12N 15/8243 (2013.01); C12Y 117/01003 (2013.01)

(58) Field of Classification Search
None
See application file for complete search history.

(56) References Cited

U.S. PATENT DOCUMENTS

| 6,080,920 | A | 6/2000 | Holton | |
|---|---|---|---|---|
| 2004/0025202 | A1* | 2/2004 | Laurie et al. ................ | 800/281 |
| 2004/0093632 | A1 | 5/2004 | Dixon et al. | |
| 2005/0069884 | A1 | 3/2005 | Spangenberg et al. | |
| 2005/0260754 | A1 | 11/2005 | Kock et al. | |
| 2012/0216318 | A1* | 8/2012 | La Rosa et al. ............ | 800/298 |

FOREIGN PATENT DOCUMENTS

| EP | 1 033 405 | | 9/2000 | |
|---|---|---|---|---|
| WO | 96/36716 | A1 | 11/1996 | |
| WO | 00/09720 | | 2/2000 | |
| WO | 0022099 | A1 | 4/2000 | |
| WO | 00/78985 | | 12/2000 | |
| WO | 02066625 | A1 | 8/2002 | |
| WO | WO02/066625 | * | 8/2002 | ............ C07K 16/40 |
| WO | WO/02/066625 | * | 8/2002 | |
| WO | 03031622 | A1 | 4/2003 | |
| WO | 03040306 | A2 | 5/2003 | |
| WO | 2004002215 | A2 | 1/2004 | |
| WO | 2004020637 | A1 | 3/2004 | |
| WO | 2004024079 | A2 | 3/2004 | |

OTHER PUBLICATIONS

Altschul, S.F. et al. "Basic Local Alignment Search Tool", J. Mol. Biol., 1990, pp. 403-410, vol. 215.
Arioli, T. et al. "In Trifolium subterraneum, chalcone synthase is encoded by multigene family", Gene, 1994, pp. 79-86, vol. 138.
Database EMBL [Online] "Medicago sativa clojne MsCHS12-1 chalcone synthase mRNA, complete cds.", Nov. 27, 1993, XP002445891, retrieved from EBI accession No. EMBL:U01021.
Database EMBL [Online] "Medicago sativa chalcone synthase (CHS2) mRNA, complete cds.",Sep. 30, 1992, XP002445892, retrieved from EBI accession No. EMBL:L02902.
Database EMBL [Online], "P sativum PSCHS2 mRNA for chalcone synthase",Jun. 5, 1992, XP002445893, retrieved from EBI accession No. EMBL:X63334.
Database EMBL [Online], "Cicer arietinum L. mRNA for chalcone synthase", Nov. 17, 1998, XP002445894, retrieved from EBI accession No. EMBL:AJ012822.1.
Database EMBL [Online], "Cicer arietinum mRNA for chalcone synthase", Nov. 11, 1998, XP002445895, retrieved from EBI accession No. EMBL:AJ012690.1.
Devic, M. et al. "The BANYULS gene encodes a DFR-like protein and is a marker of early seed coat development", Plant Journal, 1999, pp. 387-398, vol. 19, No. 4, Blackwell Scientifice Publications, Oxford, GB XP002982937.
Francois, et al. "Different approaches for multi-transgene-stacking in plants", Plant Science, Aug. 2002, pp. 281-295, vol. 163, No. 2.
Frohman, M.A. et al. "Rapid production of full-length cDNAs from rare transcripts: Amplification using a single gene-specific oligo-nucleotide primer", PNAS, Dec. 1988, pp. 8998-9002, vol. 85.
Frokmann, G. et al. "Metabolic engineering and applications of flavonoids" Current Opinion in Biotechnology, Apr. 2001, pp. 155-160, vol. 12, No. 2.

(Continued)

Primary Examiner — Lee A Visone
(74) Attorney, Agent, or Firm — Larson & Anderson, LLC

(57) ABSTRACT

The present invention relates to nucleic acid fragments encoding amino acid sequences for flavonoid biosynthetic enzymes in plants, and the use thereof for the modification of, for example, flavonoid biosynthesis in plants, and more specifically the modification of the content of condensed tannins. In particularly preferred embodiments, the invention relates to the combinatorial expression of chalcone synthase (CHS) and/or dihydroflavonol 4-reductase (BAN) and/or leucoanthocyanidine reductase (LAR) in plants to modify, for example, flavonoid biosynthesis or more specifically the content of condensed tannins.

7 Claims, 40 Drawing Sheets

(56) References Cited

OTHER PUBLICATIONS

Gish, W. et al. "Identification of protein coding regions by database similarity search", Nature Genetics, Mar. 1993, pp. 266-272, vol. 3, Nature Publishing Group.
Goderis, I. et al. "A set of molecular plant transformation vectors allowing flexible insertion of up to six expression units", Plant Molecular Biology, 2002, pp. 17-27, vol. 50.
Guo, H. et al. "Protein tolerance to random amino acid change", PNAS, Jun. 22, 2004, pp. 9205-9210, vol. 101, No. 25.
Hajdukiewicz, P. et al. "The small, versatile pPZP family of Agrobacterium binary vectors for plant transformation", Plant Molecular Biology, 1994, pp. 989-994, vol. 25.
Halpin, C. et al. "Enabling technologies for manipulating multiple genes on complex pathways", Plant Molecular Biology, Sep. 1, 2001, pp. 295-310, vol. 47, No. 1-2.
Hill, M. et al. "Fuctional Analysis of Conserved Histidines in ADP-Glucose Pyrophosphorylase from *Escherichia coli*" Biochemical and Biophysical Research Communications, 1998, pp. 573-577, vol. 244.
Howles, P. et al. "Nucleotide Sequence of Additional Members of the Gene Family Encoding Chalcone Synthase in Trifolium subterraneum" Plant Physiol., 1995, pp. 1035-1036, vol. 107.
Ichinose, Y. et al. "Molecular cloning of chalcone synthase cDNAs from Pisum sativum" Plant Molecular Biology, 1992, pp. 1009-1012, vol. 18, No. 5.
Jende-Strid, B. et al. "Gene enzyme relations in the pathway of flavonoid biosynthesis in barley", Theoretical and Applied Genetics, 1991, pp. 668-674, vol. 81, No. 5, XP008082140.
Joseph, R. et al. "Proanthocyanidin synthesis in the forage legume onobrychis viciifolia. A study of chalcone synthase, dihydroflavonol 4-reductase and leucoanthocyanidin 4-reductase in developing leaves", Australian Journal of Plant Physiology, 1998, pp. 271-278, vol. 25, No. 3.
Junghans, H. et al. "Stress response in alfalfa (*Medicago sativa* L). 15 Characterization and expression patterns of members of a subset of the chalcone synthase multigene family", Plant Molecular Biology, May 1993, pp. 239-253, Kluwer Academic Publishers, Belgium XP002158812.
Loh, E. et al. "Polymerase Chain Reaction with Single-Sided Specificity: Analysis of T Cell Receptor S Chain", Science, Jan. 1989, pp. 217-220, vol. 243.
Lukaszewicz, M. et al. "Antioxidant capacity manipulation in transgenic potato tuber by changes in phenoiic compounds content", Journal of Agricultural and Food Chemistry, Mar. 24, 2004, pp. 1526-1533, vol. 52, No. 6.
McKhann, H. et al. "Isolation of chalcone synthase and chalcone isomerase cDNAs from Alfalfa (*Medicago sativa* L.): highest transcript levels occur in young roots and root tips", Plant Molecular Biology, 1994, pp. 767-777, vol. 5, No. 24.
Nakashita, H. et al. "Introduction of bacterial metabolism into higher plants of polycistronic transgene expression", Bioscience Biotechnology Biochemistry, Jul. 2001, pp. 1688-1691, vol. 65, No. 7.
Ohara, O. et al. "One-sided polymerase chain reaction: The amplification of cDNA", PNAS, Aug. 1989, pp. 5673-5677, vol. 86.
Robbins, M.P. et al. "Metabolic Engineering of Condensed Tannins and Other Phenotic Pathways in Forage and Fodder Crops", 2000, pp. 165-177, Chapter 8, Kluwer Academic Publishers.
Schardl, C.L. et al. "Design and construction of a versatile system for the expression of foreign genes in plants", Gene. 1987, pp. 1-11, vol. 61.
Suzuki, K. et al. "Flower color modification of Torenia hybrida by cosuppression of anthocyanin biosynthesis genes", Molecular Breeding, 2000, pp. 239-246, vol. 6.
Tanaka, Y. et al. "Metabolic engineering to modify flower color", Plant and Cell Physiology, Nov. 1998, pp. 1119-1126, vol. 39, No. 11.

\* cited by examiner

```
   1 GAATTCACTA GTGATTAAGC AGTGGTAACA ACGCAGAGTA CGCGGGGAAC
  51 AAAAACAACT ACGCATATTA TATATATATA TATATAGTCT ATAATTGAAA
 101 GAAACTGCTA AAGATATTAT TAAGATATGG TGAGTGTAGC TGAAATTCGC
 151 AAGGCTCAGA GGGCTGAAGG CCCTGCAACC ATTTTGGCCA TTGGCACTGC
 201 AAATCCACCA AACCGTGTTG AGCAGAGCAC ATATCCTGAT TTCTACTTCA
 251 AAATTACAAA CAGTGAGCAC AAGACTGAGC TCAAAGAGAA GTTCCAACGC
 301 ATGTGTGACA AATCCATGAT CAAGAGCAGA TACATGTATC TAACAGAAGA
 351 GATTTTGAAA GAAAATCCTA GTCTTTGTGA ATACATGGCA CCTTCATTGG
 401 ATGCTAGGCA AGACATGGTG GTGGTTGAGG TACCTAGACT TGGGAAGGAG
 451 GCTGCAGTCA AGGCCATTAA AGAATGGGGT CAACCAAAGT CAAAGATTAC
 501 TCACTTAATC TTTTGCACCA CAAGTGGTGT TGACATGCCT GGTGCTGATT
 551 ACCAACTCAC AAAACTCTTA GGTCTTCGCC CATATGTGAA AAGGTATATG
 601 ATGTACCAAC AAGGTTGTTT TGCAGGAGGC ACGGTGCTTC GTTTGGCAAA
 651 AGATTTGGCC GAGAACAACA AAGGTGCTCG TGTGCTAGTT GTTTGTTCTG
 701 AAGTCACCGC AGTCACATTT CGCGGCCCCA GTGATACTCA CTTGGACAGT
 751 CTTGTTGGAC AAGCATTGTT TGGAGATGGA GCCGCTGCAC TAATTGTTGG
 801 TTCTGATCCA GTGCCTGAAA TTGAGAAACC AATATTTGAG ATGGTTTGGA
 851 CTGCACAAAC AATTGCTCCA GACAGTGAAG GTGCCATTGA TGGTCATCTT
 901 CGTGAAGCTG GGCTAACATT TCATCTTCTT AAAGATGTTC CTGGGATTGT
 951 ATCAAAGAAC ATTAATAAAG CATTGGTTGA GGCTTTCCAA CCATTAGGAA
1001 TTTCTGACTA CAACTCAATC TTTTGGATTG CACACCCGGG TGGACCTGCA
1051 ATTCTTGATC AAGTAGAACA AAAGCTAGCC TTGAAGCCCG AAAAGATGAG
1101 GGCCACGAGG GAAGTTCTAA GTGAATATGG AAACATGTCA AGCGCATGTG
1151 TATTGTTCAT CTTAGATGAG ATGCGGAAGA AATCGGCTCA AAATGGACTT
1201 AAGACAACTG GAGAAGGACT TGATTGGGGT GTGTTGTTCG GCTTCGGACC
1251 AGGACTTACC ATTGAAACCG TTGTTCTTCG TAGCGTGGCT ATATAAGATG
1301 TGTGATTGTT TTTATTTTAA TGTATTACTT TTAATCTTGC TGCCTTGAAT
1351 TTCGATTTAA GAATAAATAA ATATATCTTT TGATAAAAAA AAAAAAAAAA
1401 AAAAAAAAAA AAGTACTCTG CGTTGTTACC ACTGCTTAAT CGAATTC
```

FIGURE 2

```
  1  MVSVAEIRKA QRAEGPATIL AIGTANPPNR VEQSTYPDFY FKITNSEHKT
 51  ELKEKFQRMC DKSMIKSRYM YLTEEILKEN PSLCEYMAPS LDARQDMVVV
101  EVPRLGKEAA VKAIKEWGQP KSKITHLIFC TTSGVDMPGA DYQLTKLLGL
151  RPYVKRYMMY QQGCFAGGTV LRLAKDLAEN NKGARVLVVC SEVTAVTFRG
201  PSDTHLDSLV GQALFGDGAA ALIVGSDPVP EIEKPIFEMV WTAQTIAPDS
251  EGAIDGHLRE AGLTFHLLKD VPGIVSKNIN KALVEAFQPL GISDYNSIFW
301  IAHPGGPAIL DQVEQKLALK PEKMRATREV LSEYGNMSSA CVLFILDEMR
351  KKSAQNGLKT TGEGLDWGVL FGFGPGLTIE TVVLRSVAI
```

```
   1 GAATTCGATT AAGCAGTGGT AACAACGCAG AGTACGCGGG GATTCAATCT
  51 GTTGTGCATA AAATTCACTC ATTGCATAGA AAACCATACA CATTTGATCT
 101 TGCAAAGAAG AAATATGGGA GACGAAGGTA TAGTGAGAGG TGTCACAAAG
 151 CAGACAACCC CTGGGAAGGC TACTATATTG GCTCTTGGCA AGGCATTCCC
 201 TCACCAACTT GTGATGCAAG AGTGTTTAGT TGATGGTTAT TTTAGGGACA
 251 CTAATTGTGA CAATCCTGAA CTTAAGCAGA AACTTGCTAG ACTTTGTAAG
 301 ACAACCACGG TAAAAACAAG GTATGTTGTT ATGAATGAGG AGATACTAAA
 351 GAAATATCCA GAACTTGTTG TCGAAGGCGC CTCAACTGTA AAACAACGTT
 401 TAGAGATATG TAATGAGGCA GTAACACAAA TGGCAATTGA AGCTTCCCAA
 451 GTTTGCCTAA AGAATTGGGG TAGATCCTTA TCGGACATAA CTCATGTGGT
 501 TTATGTTTCA TCTAGTGAAG CTAGATTACC CGGTGGTGAC CTATACTTGT
 551 CAAAAGGACT AGGACTAAAC CCTAAAATTC AAAGAACCAT GCTCTATTTC
 601 TCTGGATGCT CGGGAGGCGT AGCCGGCCTT CGCGTTGCGA AAGACGTAGC
 651 TGAGAACAAC CCTGGAAGTA GAGTTTTGCT TGCTACTTCG GAAACTACAA
 701 TTATTGGATT CAAGCCACCA AGTGTTGATA GACCTTATGA TCTTGTTGGT
 751 GTGGCACTCT TTGGAGATGG TGCTGGTGCA ATGATAATTG GCTCAGACCC
 801 GGTATTTGAA ACTGAGACAC CATTGTTTGA GCTGCATACT TCAGCTCAGG
 851 AGTTTATACC AGACACCGAG AAGAAAATTG ATGGGCGGCT GACGGAGGAG
 901 GGCATAAGTT TCACACTAGC AAGGGAACTT CCGCAGATAA TCGAAGACAA
 951 TGTTGAGGGA TTCTGTAATA AACTAATTGA TGTTGTTGGG TTGGAGAATA
1001 AGGAGTACAA TAAGTTGTTT TGGGCTGTGC ATCCAGGTGG GCCTGCGATA
1051 TTGAATCGCG TGGAGAAGCG GCTTGAGTTG TCGCCGCAGA AGCTGAATGC
1101 TAGTAGAAAA GCTCTAATGG ATTATGGAAA TGCTAGCAGC AATACTATTG
1151 TTTATGTGCT GGAATATATG CTAGAAGAGG AAAAGAAGAT TAAAAAGGCG
1201 GGTGGAGGAG ATTCTGAATG GGGATTGATA CTTGCTTTTG GACCTGGAAT
1251 TACTTTTGAG GGGATTCTAG CAAGGAACTT GTGTGCATGA AGTCTTATAC
1301 AATTGTGATG CATGACTTAT ACTCTTATTT CTACTAATTA TTATATTAAG
1351 CAAATTCAGA ACTTTTAAGT AATGATTTAA TGAAGAATAC TTATAGTATA
1401 TTGACTTTAT TCACTTTCAA AGCAAGTTTA TGATCCTAAG ACATGGTAGA
1451 ACTTGAGCAT GTGGAATAGT TGTAACAAAA ACTCTAAGCA AATAGAGACT
1501 TTATGTAGTA TAAAGCATTT CCAGACATGA TAAATAATGG TACCTCAGAA
1551 CATAAATAT ATTTAGCTAT CTTTCATCCC CAACTTTACA CATCCACCAA
1601 GGTACAGAAT AAGCATATGT CAACACAAAA TGTACTCTAA GTCTAACATG
1651 AGTAACCAAA CATGATGCCT GATTAAGTTA AAAGAAAAGA AAATCTGAGG
1701 GCATAGATCT TCAATCACAC CACTCCAGAG GGAAGGCGTA GAACAAGCTG
```

FIGURE 6

```
1751 TCCGCCGAAA ACACTGCAAT TCAATAAATA TCATTAGGAC AACAGTGCAG
1801 AGTCATGCGG GAAATGTCTT AAGTCACTGT ACTAAAAATA TAGGATTATA
1851 TTATGAACTA TACTAACCTT TTCACATAAT AGTAACAGAA ATCAGCTAAG
1901 ATGAATGTCT GGACAATTTC TGAGATAAGA ACCATGACGG CCATAAGCCA
1951 TACCCCAAGG CAACCAATAA ATGTCCACGG GTATCTAACA CCTGTTGCAA
2001 GAAATAGTAA GTTATTAGGA GATGTGCGGT TACGAAATTC AAGCTACACA
2051 ACAAAAGGAG GCCAGAACAA CAGCAATCTT GTAACCAGAT GACAACAATA
2101 AAATGTAAAC TTAAAGAGAC CGAACACACA AACATTGCAA CTCAGATGGA
2151 ATTGCTGCCA TGTAACTAGT AGGAGATTTG GGACGTCAAA TCAGTATATT
2201 ATGCAAATAC AAGGTATGAC CGCCTTGTCT ATTGTAGCAT ACAACAAACG
2251 TACAGTGGGT TTGTCCCTCT CAAAATGGCA GGATCTTTAC AGCACAATAT
2301 TTGGTTTTGT CATACTTATA CCATAAAAAA AAAAAAAAAA AAAAAAAAAA
2351 AAAGTACTCT GCGTTGTTAC CACTGCTTAA TCACTAGTGA ATTC
```

FIGURE 6 (cont.)

```
  1 MGDEGIVRGV TKQTTPGKAT ILALGKAFPH QLVMQECLVD GYFRDTNCDN
 51 PELKQKLARL CKTTTVKTRY VVMNEEILKK YPELVVEGAS TVKQRLEICN
101 EAVTQMAIEA SQVCLKNWGR SLSDITHVVY VSSSEARLPG GDLYLSKGLG
151 LNPKIQRTML YFSGCSGGVA GLRVAKDVAE NNPGSRVLLA TSETTIIGFK
201 PPSVDRPYDL VGVALFGDGA GAMIIGSDPV FETETPLFEL HTSAQEFIPD
251 TEKKIDGRLT EEGISFTLAR ELPQIIEDNV EGFCNKLIDV VGLENKEYNK
301 LFWAVHPGGP AILNRVEKRL ELSPQKLNAS RKALMDYGNA SSNTIVYVLE
351 YMLEEEKKIK KAGGGDSEWG LILAFGPGIT FEGILARNLC A
```

FIGURE 7

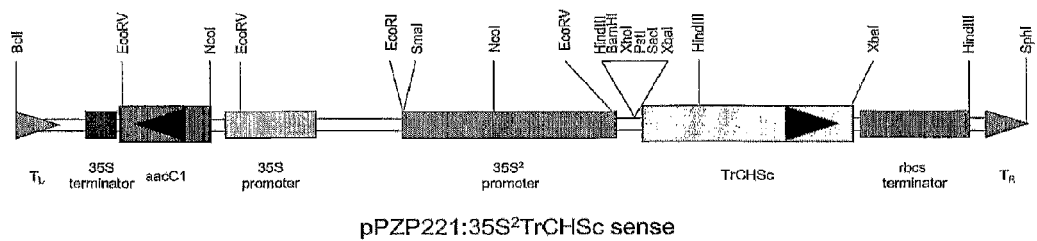
pPZP221:35S²TrCHSc sense
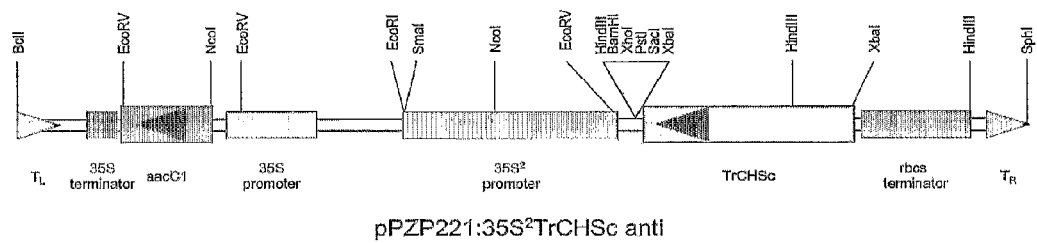
pPZP221:35S²TrCHSc anti
FIGURE 8

```
   1 GAATTCGATT AAGCAGTGGT AACAACGCAG AGTACGCGGG ACTAAGCCTT
  51 GATTCATTGT TTGTTTCCAT AACACAAGAA CTAGTGTTTG CTTGAATCTT
 101 AAGAAAAAAT GCCTCAAGGT GATTTGAATG GAAGTTCCTC GGTGAATGGA
 151 GCACGTGCTA GACGTGCTCC TACTCAGGGA AAGGCAACGA TACTTGCATT
 201 AGGAAAGGCT TTCCCCGCCC AGGTCCTCCC TCAAGAGTGC TTGGTGGAAG
 251 GATTCATTCG CGACACTAAG TGTGACGATA CTTATATTAA GGAGAAATTG
 301 GAGCGTCTTT GCAAAAACAC AACTGTGAAA ACAAGATACA CAGTAATGTC
 351 AAAGGAGATC TTAGACAACT ATCCAGAGCT AGCCATAGAT GGAACACCAA
 401 CAATAAGGCA AAAGCTTGAA ATAGCAAATC CAGCAGTAGT TGAAATGGCA
 451 ACAAGAGCAA GCAAAGATTG CATCAAAGAA TGGGAAGGT CACCTCAAGA
 501 TATCACACAC ATAGTCTATG TTTCCTCGAG CGAAATTCGT CTACCCGGTG
 551 GTGACCTTTA TCTTGCAAAT GAACTCGGCT TAAACAGCGA TGTTAATCGC
 601 GTAATGCTCT ATTTCCTCGG TTGCTACGGC GGTGTCACTG GCTTACGTGT
 651 CGCCAAAGAC ATCGCCGAAA ATAACCCTGG TAGTAGGGTG TTACTCACAA
 701 CATCCGAGAC CACTATTCTC GGTTTTCGAC CACCGAGTAA AGCTAGACCT
 751 TATGACCTCG TTGGCGCTGC ACTTTTCGGT GATGGCGCCG CTGCTGCAAT
 801 AATTGGAACA GACCCTATAT TGAATCAAGA ATCACCTTTC ATGGAATTGA
 851 ACCATGCAGT CCAAAAATTC TTGCCTGATA CACAAAATGT GATTGATGGT
 901 AGAATCACTG AAGAGGGTAT TAATTTTAAG CTTGGAAGAG ACCTTCCTCA
 951 AAAAATTGAA GACAATATTG AAGAATTTTG CAAGAAAATT ATGGCTAAAA
1001 GTGATGTTAA GGAATTTAAT GACTTATTTT GGGCTGTTCA TCCTGGTGGG
1051 CCAGCTATAC TCAATAAGCT AGAAAATATA CTCAAATTGA AAAGTGATAA
1101 ATTGGATTGT AGTAGGAAGG CATTAATGGA TTATGGAAAT GTTAGTAGCA
1151 ATACTATATT CTATGTGATG GAGTATATGA GAGATTATTT GAAGGAAGAT
1201 GGAAGTGAAG AATGGGGATT AGGATTGGCT TTTGGACCAG GGATTACTTT
1251 TGAAGGGGTT CTCCTCCGTA GCCTTTAATC TTGAAATAAT AATTCATATG
1301 AAATTACTTG TCTTAAGATT GTGATAGGAA GATGAATATG TATTGGATTA
1351 ATATTGATAT GGTGTTATTT TAAGTTGATT TTAAAAAAAG TTTATTAATA
1401 AAGTATGATG TAACAATTGT TGTTTGAATG TTAAAAGGGA AGTATACTAT
1451 TTTAAGTTCT TGACCATACT GATTTTTTCT TTACACATTT TCATATCTAA
1501 AATTGTTCTA TGATATCTTC ATTGTTGATA CTGTAATAAT ATAATATCTA
1551 ATTTGGCTGG CAAAATGAAA GATTTTTCAC CGAAAAAAAA AAAAAAAAA
1601 AAAAAAAAAA AAGTACTCTG CGTTGTTACC ACTGCTTAAT CACTAGTGAA
1651 TTC
```

FIGURE 10

```
  1  MPQGDLNGSS SVNGARARRA PTQGKATILA LGKAFPAQVL PQECLVEGFI
 51  RDTKCDDTYI KEKLERLCKN TTVKTRYTVM SKEILDNYPE LAIDGTPTIR
101  QKLEIANPAV VEMATRASKD CIKEWGRSPQ DITHIVYVSS SEIRLPGGDL
151  YLANELGLNS DVNRVMLYFL GCYGGVTGLR VAKDIAENNP GSRVLLTTSE
201  TTILGFRPPS KARPYDLVGA ALFGDGAAAA IIGTDPILNQ ESPFMELNHA
251  VQKFLPDTQN VIDGRITEEG INFKLGRDLP QKIEDNIEEF CKKIMAKSDV
301  KEFNDLFWAV HPGGPAILNK LENILKLKSD KLDCSRKALM DYGNVSSNTI
351  FYVMEYMRDY LKEDGSEEWG LGLAFGPGIT FEGVLLRSL
```

FIGURE 11

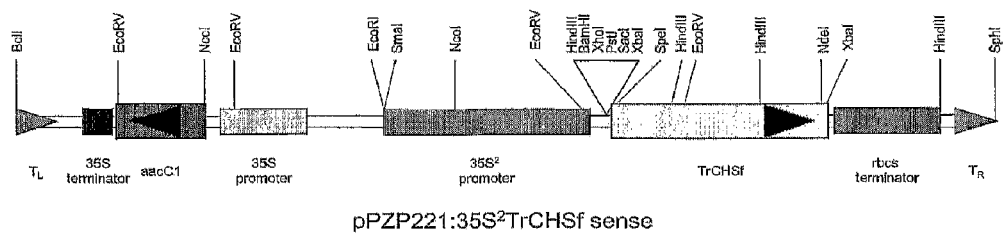
pPZP221:35S²TrCHSf sense
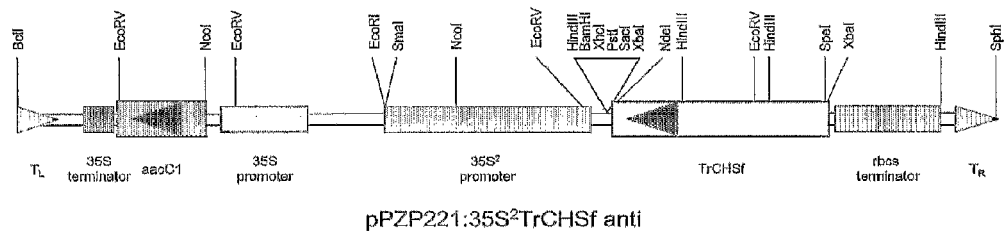
pPZP221:35S²TrCHSf anti
FIGURE 12

TrCHSh

```
   1 GAATTCACTA GTGATTAAGC AGTGGTAACA ACGCAGAGTA CGCGGGGGAA
  51 TCCACCAAAT CAACACCATT AATAACCTTC CAAATTCTCG TTACCTCACC
 101 AAATCTCATT TTTCATTATA TATCTTGGGT ACATCTTTTG TTACCTCCAA
 151 CAAAAAAATG GTGACCGTAG AAGAGATTCG TAACGCCCAA CGTTCAAATG
 201 GCCCTGCCAC TATCTTAGCT TTTGGCACAG CCACTCCTTC TAACTGTGTC
 251 ACTCAAGCTG ATTATCCTGA TTACTACTTT CGTATCACCA ACAGCGAACA
 301 TATGACTGAT CTTAAGGAAA AATTCAAGCG GATGTGTGAT AGATCAATGA
 351 TAAAGAAACG TTACATGCAC CTAACAGAAG ACTTTCTGAA GGAGAATCCA
 401 AATATGTGTG AATACATGGC ACCATCACTA GATGTAAGAC GAGACATAGT
 451 GGTTGTTGAA GTACCAAAGC TAGGTAAAGA AGCAGCAAAA AAAGCCATAT
 501 GTGAATGGGG ACAACCAAAA TCCAAAATCA CACATCTTGT TTTCTGCACC
 551 ACTTCCGGTG TTGACATGCC GGGAGCCGAT TACCAACTCA CCAAACTTTT
 601 AGGCTTAAAA CCTTCTGTCA AGCGTCTCAT GATGTATCAA CAAGGTTGTT
 651 TCGCTGGCGG CACAGTTCTC CGCTTAGCAA AAGACCTTGT TGAGAATAAC
 701 AAAAATGCAA GAGTTCTTGT TGTTTGTTCT GAAATTACTG CGGTTACTTT
 751 TCGTGGACCA TCGGATACTC ATCTTGATTC GCTCGTGGGA CAGGCGCTTT
 801 TTGGTGATGG AGCCGCAGCA ATGATTATTG GTGCGGATCC TGATTTAACC
 851 GTGGAGCGTC CGATTTTCGA GATTGTTTCG GCTGCTCAGA CTATTCTTCC
 901 TGATTCTGAT GGCGCAATTG ATGGACATCT TCGTGAAGTG GGGCTCACTT
 951 TTCATTTATT GAAAGATGTT CCGGGGATTA TTTCAAAGAA CATTGAAAAA
1001 AGTTTAGTTG AAGCTTTTGC GCCTATTGGG ATTAATGATT GGAACTCAAT
1051 ATTTTGGGTT GCACATCCAG GTGGACCGGC TATTTTAGAC CAGGTTGAAG
1101 AGAAACTCCA TCTTAAAGAG GAGAAACTCC GGTCCACCCG GCATGTGCTT
1151 AGTGAATATG GAAATATGTC AAGTGCATGT GTTTTATTTA TTTTGGATGA
1201 AATGAGAAAG AGGTCTAAAG AGGAAGGGAT GATTACAACT GGTGAAGGGT
1251 TGGAATGGGG TGTGTTGTTT GGGTTTGGAC CGGGTTTAAC TGTTGAAACC
1301 GTTGTGCTTC ATAGTGTTCC GGTTCAGGGT TGAATTTATT ATACATAGAT
1351 TGGAAAATAA AATTTGCCTG CCGAGAGATG TGAACTAACT TTGTAGGCAA
1401 GCTCAAATTA AAGTTTGAGA TAATATTGTG CTTTAGTTAT TATGGTATGT
1451 AATGTAATGT TTTTACTTTT TTCGAAATTC ATGTAATTTG ATATGTAAAG
1501 TAATATGTTT GGGTTGGAAT ATAATTATTT GTTAACTAAA AAAAAAAAAA
1551 AAAAAAAAAA AAAAGTACT CTGCGTTGTT ACCACTGCTT AATCGAATTC
```

FIGURE 14

```
  1  MVTVEEIRNA  QRSNGPATIL  AFGTATPSNC  VTQADYPDYY  FRITNSEHMT
 51  DLKEKFKRMC  DRSMIKKRYM  HLTEDFLKEN  PNMCEYMAPS  LDVRRDIVVV
101  EVPKLGKEAA  KKAICEWGQP  KSKITHLVFC  TTSGVDMPGA  DYQLTKLLGL
151  KPSVKRLMMY  QQGCFAGGTV  LRLAKDLVEN  NKNARVLVVC  SEITAVTFRG
201  PSDTHLDSLV  GQALFGDGAA  AMIIGADPDL  TVERPIFEIV  SAAQTILPDS
251  DGAIDGHLRE  VGLTFHLLKD  VPGIISKNIE  KSLVEAFAPI  GINDWNSIFW
301  VAHPGGPAIL  DQVEEKLHLK  EEKLRSTRHV  LSEYGNMSSA  CVLFILDEMR
351  KRSKEEGMIT  TGEGLEWGVL  FGFGPGLTVE  TVVLHSVPVQ  G
```

FIGURE 15

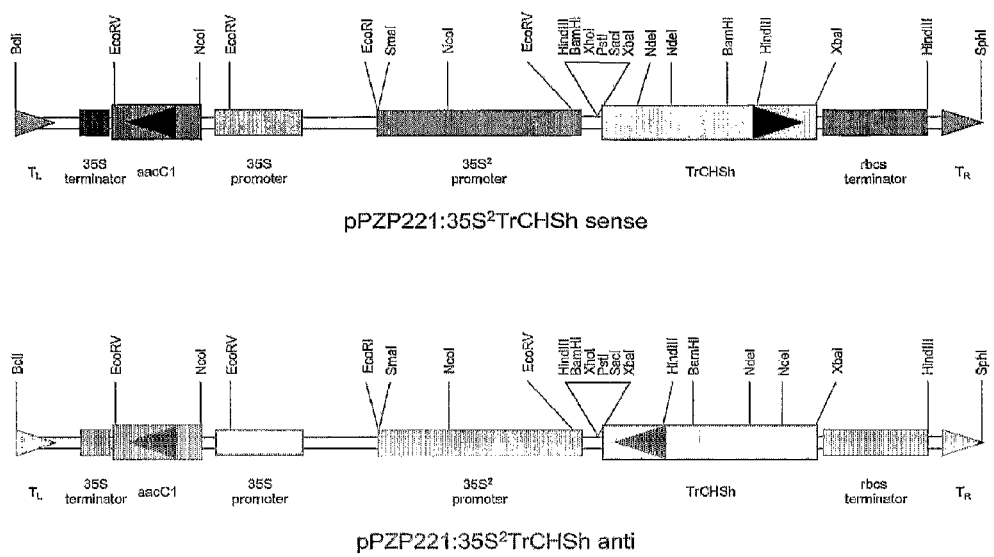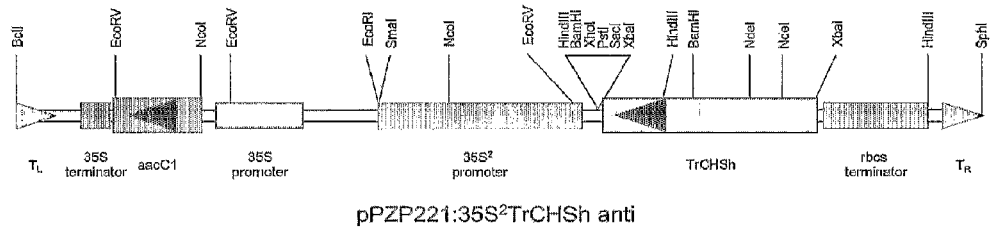
FIGURE 16

```
   1 GAATTCGATT AAGCAGTGGT AACAACGCAG AGTACGCGGG ATAAAAACTG
  51 CACTAGTGTG TATAAGTTTC TTGGTGAAAA AAGAGTTTGT AAATTAACAT
 101 CATGGCTAGT ATCAAACAAA TTGGAAACAA GAAAGCATGT GTGATTGGTG
 151 GCACTGGTTT TGTTGCATCT ATGTTGATCA AGCAGTTACT TGAAAAGGGT
 201 TATGCTGTTA ATACTACCGT TAGAGACCCA GATAGCCCTA AGAAAATATC
 251 TCACCTAGTG GCACTGCAAA GTTTGGGGGA ACTGAATCTA TTTAGAGCAG
 301 ACTTAACAGT TGAAGAAGAT TTTGATGCTC CTATAGCAGG ATGTGAACTT
 351 GTTTTTCAAC TTGCTACACC TGTGAACTTT GCTTCTCAAG ATCCTGAGAA
 401 TGACATGATA AAGCCAGCAA TCAAAGGTGT GTTGAATGTG TTGAAAGCAA
 451 TTGCAAGAGC AAAAGAAGTT AAAAGAGTTA TCTTAACATC TTCGGCAGCC
 501 GCGGTGACTA TAAATGAACT CAAAGGGACA GGTCATGTTA TGGATGAAAC
 551 CAACTGGTCT GATGTTGAAT TTCTCAACAC TGCAAAACCA CCCACTTGGG
 601 GTTATCCTGC CTCAAAAATG CTAGCTGAAA AGGCTGCATG GAAATTTGCT
 651 GAAGAAAATG ACATTGATCT AATCACTGTG ATACCTAGTT TAACAACTGG
 701 TCCTTCTCTC ACACCAGATA TCCCATCTAG TGTTGGCTTG GCAATGTCTC
 751 TAATAACAGG CAATGATTTT CTCATAAATG CTTTGAAAGG AATGCAGTTT
 801 CTGTCGGGTT CGTTATCCAT CACTCATGTT GAGGATATTT GCCGAGCTCA
 851 TATATTTCTT GCAGAGAAAG AATCAGCTTC TGGTAGATAC ATTTGCTGTG
 901 CTCACAATAC TAGTGTTCCC GAGCTTGCAA AGTTTCTCAA CAAACGATAT
 951 CCTCAGTATA AAGTTCCAAC TGAATTTGAT GATTGCCCCA GCAAGGCAAA
1001 GTTGATAATC TCTTCTGAAA AGCTTATCAA AGAAGGGTTC AGTTTCAAGC
1051 ATGGTATTGC CGAAACTTTC GACCAGACTG TCGAGTATTT TAAGACTAAG
1101 GGGGCACTGA AGAATTAGAT TTTGATATTT CTAATTCAAT AGCAAACTCT
1151 AAGCTTGTTA TGTGTTTGTG AAGTTCAGAG TGAAATATCA AATGAATAAG
1201 TGGAGAGAGC ACAATAAGAG GAGAGCACAA TAATTTTGGA AAAAAAAAA
1251 AAAAAAAAAA AAAAAAAGT ACTCTGCGTT GTTACCACTG CTTAATCACT
1301 AGTGAATTC
```

FIGURE 18

```
  1  MASIKQIGNK KACVIGGTGF VASMLIKQLL EKGYAVNTTV RDPDSPKKIS
 51  HLVALQSLGE LNLFRADLTV EEDFDAPIAG CELVFQLATP VNFASQDPEN
101  DMIKPAIKGV LNVLKAIARA KEVKRVILTS SAAAVTINEL KGTGHVMDET
151  NWSDVEFLNT AKPPTWGYPA SKMLAEKAAW KFAEENDIDL ITVIPSLTTG
201  PSLTPDIPSS VGLAMSLITG NDFLINALKG MQFLSGSLSI THVEDICRAH
251  IFLAEKESAS GRYICCAHNT SVPELAKFLN KRYPQYKVPT EFDDCPSKAK
301  LIISSEKLIK EGFSFKHGIA ETFDQTVEYF KTKGALKN
```

FIGURE 19

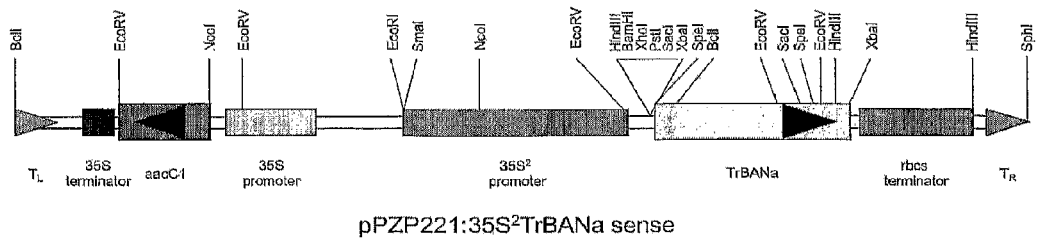
pPZP221:35S²TrBANa sense
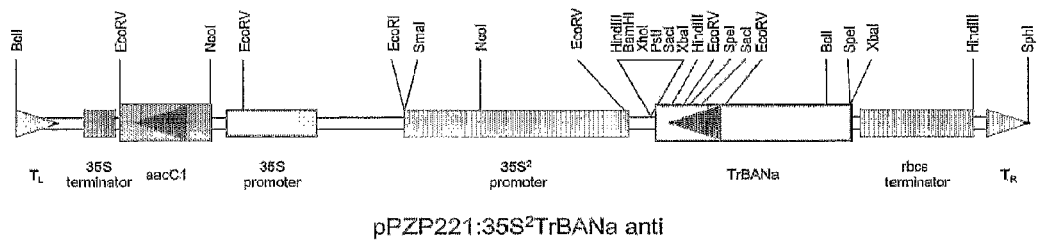
pPZP221:35S²TrBANa anti
FIGURE 20

TrLARa

```
   1 GAATTCGATT AAGCAGTGGT AACAACGCAG AGTACGCGGG GATACCAACA
  51 TTGTCACAAT TAACTCTAAA AGCAAAGCAA TGGCACCAGC AGCAACATCA
 101 TCACCAACCA CTCCTACTAC TACCAAGGGT CGTGTCCTAA TTGTTGGAGG
 151 AACAGGTTTC ATTGGAAAAT TTGTAACTGA GGCAAGTCTT TCCACAACAC
 201 ACCCAACCTA CTTGTTGGTT CGGCCAGGAC CTCTTCTCTC TTCTAAGGCT
 251 GCCACTATTA AGGCATTCCA AGAGAAAGGT GCCATTGTCA TTTATGGTCG
 301 GGTAAATAAT AAGGAGTTCA TGGAGATGAT TTTGAAAAAG TATGAGATAA
 351 ATGTAGTCAT TTCTGCAATA GGAGGCTCTG ATGGCTTGCT GGAACAGCTT
 401 ACTTTGGTGG AGGCCATGAA ATCTATTAAC ACCATTAAGA GGTTTTTGCC
 451 TTCGGAATTT GGTCACGATG TGGACAGAGC AAATCCTGTG GAACCTGGCC
 501 TAACAATGTA CAAACAGAAA CGTTTGGTTA GACGTGTGAT CGAAGAATCT
 551 GGTATACCAT ACACCTACAT CTGTTGCAAT TCGATCGCAT CTTGGCCGTA
 601 CTATGACAAT TGTCATCCAT CACAGCTTCC TCCACCGTTG GATCAATTAC
 651 ATATTTATGG TCATGGCGAT GTCAAAGCTT ACTTTGTTGA TGGCTATGAT
 701 ATTGGGAAAT TCACAATGAA GGTCATTGAT GATGAAAGAA CAATCAACAA
 751 AAATGTTCAT TTTCGACCTT CTAACAATTG TTATAGCATG AATGAGCTTG
 801 CTTCTTTGTG GGAAAACAAA ATTGCACGAA AAATTCCTAG AGTGATCGTC
 851 TCTGAAGACG ATCTTCTAGC AATAGCCGCA GAAAATTGCA TACCGGAAAG
 901 TGTCGTGGCA CCAATCACTC ATGATATATT CATCAATGGA TGTCAAGTTA
 951 ACTTCAAGAT AGATGGAATT CATGATGTTG AAATTGGCAC TCTATATCCT
1001 GGTGAATCGG TAAGAAGTTT GGAGGAATGC TATGAGAAAT TTGTTGTCAT
1051 GGCGGCTGAC AAGATTCATA AGAAGAAAC TGGAGTTACC GCAGGTGGGG
1101 GCGGCACAAC GGCTATGGTA GAGCCGGTGC CAATCACAGC TTCCTGTTGA
1151 AAAGGTTCAC CTGAGGTGGA TATTCTTTTG AGTCATAAGA CATGTTGATT
1201 GTTGATGTTG TTTTCAAGAA TGTTTCATCA TTTCATGTGT TTTATTAATC
1251 CTAAGTACAA ATAATTGCTG TCTACGTACG TTCTTAGTTG CAAAAATTCT
1301 TGTTATTCTC TATTGAGGTA AAAGTCTTCA TGTTTACAAA AAAAAAAAA
1351 AAAAAAAAAA AAAAAAAAGT ACTCTGCGTT GTTACCACTG CTTAATCACT
1401 AGTGAATTC
```

FIGURE 22

```
  1  MAPAATSSPT  TPTTTKGRVL  IVGGTGFIGK  FVTEASLSTT  HPTYLLVRPG
 51  PLLSSKAATI  KAFQEKGAIV  IYGRVNNKEF  MEMILKKYEI  NVVISAIGGS
101  DGLLEQLTLV  EAMKSINTIK  RFLPSEFGHD  VDRANPVEPG  LTMYKQKRLV
151  RRVIEESGIP  YTYICCNSIA  SWPYYDNCHP  SQLPPPLDQL  HIYGHGDVKA
201  YFVDGYDIGK  FTMKVIDDER  TINKNVHFRP  SNNCYSMNEL  ASLWENKIAR
251  KIPRVIVSED  DLLAIAAENC  IPESVVAPIT  HDIFINGCQV  NFKIDGIHDV
301  EIGTLYPGES  VRSLEECYEK  FVVMAADKIH  KEETGVTAGG  GGTTAMVEPV
351  PITASC
```

FIGURE 23

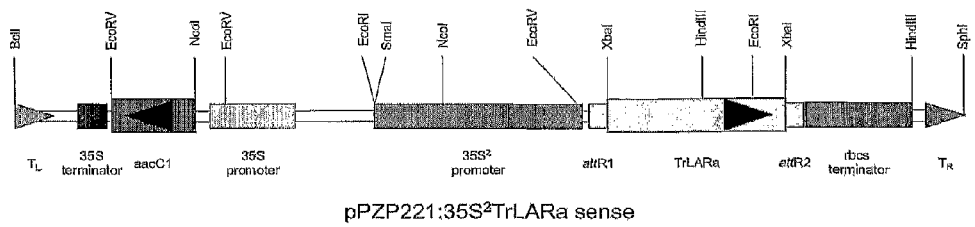
pPZP221:35S²TrLARa sense
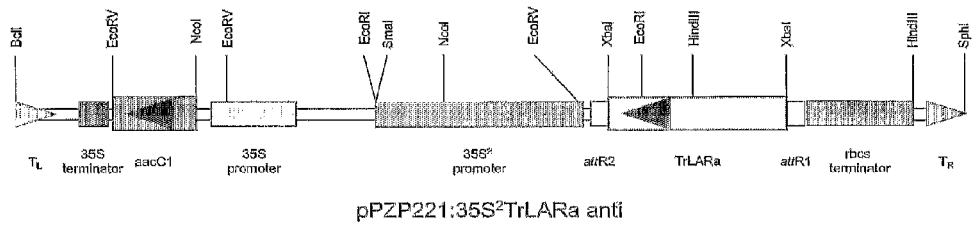
pPZP221:35S²TrLARa anti
FIGURE 24

```
   1 GAATTCGATT AAGCAGTGGT AACAACGCAG AGTACGCGGG AGGATCCTTC
  51 CATTTTGCAT ACCAACATTG TCACAATTAA CTCTAAAAGC AAAGCAATGG
 101 CACCAGCAGC AACATCATCA CCAACCACTC CTACTACTAC CAAGGGTCGT
 151 GTCCTAATTG TTGGAGGAAC AGGTTTCATT GGAAAATTTG TAACTGAGGC
 201 AAGTCTTTCC ACAACACACC CAACCTACTT GTTGGTTCGG CCAGGACCTC
 251 TTCTCTCTTC TAAGGCTGCC ACTATTAAGG CATTCCAAGA GAAAGGTGCC
 301 ATTGTCATTT ATGGTCGGGT AAATAATAAG GAGTTCATGG AGATGATTTT
 351 GAAAAGTAT GAGATAAATG TAGTCATTTC TGCAATAGGA GGCTCTGATG
 401 GCTTGCTGGA ACAGCTTACT TTGGTGGAGG CCATGAAATC TATTAACACC
 451 ATTAAGAGGT TTTTGCCTTC AGAATTTGGT CACGATGTGG ACAGAGCAAA
 501 TCCTGTGGAA CCTGGCCTAA CAATGTACAA ACAGAAACGT TTGGTTAGAC
 551 GTGTGATCGA AGAATCTGGT GTACCATACA CCTACATCTG TTGCAATTCG
 601 ATCGCATCCT GGCCGTACTA TGACAATTGT CATCCATCAC AGCTTCCTCC
 651 ACCGTTGGAT CAATTACATA TTTATGGTCA TGGCGATGTC AAAGCTTACT
 701 TTGTTGATGG CTATGATATT GGGAAATTCA CAATGAAGGT CATTGATGAT
 751 GAAAGAACAA TCAACAAAAA TGTTCATTTT CGACCTTCTA ACAATTGTTA
 801 TAGCATGAAT GAGCTTGCTT CTTTGTGGGA AAACAAAATT GCACGAAAAA
 851 TTCCTAGAGT GATCGTCTCT GAAGACGATC TTCTAGCAAT AGCCGCAGAA
 901 AACTGCATAC CGGAAAGTGT TGTGGCATCA ATCACTCATG ATATATTCAT
 951 CAATGGATGT CAAGTTAACT TCAAGGTAGA TGGAATTCAT GATGTTGAAA
1001 TTGGCACTCT ATATCCTGGT GAATCGGTAA GAAGTTTGGA GGAATGCTAT
1051 GAGAAATTTG TTGTCATGGC GGCTGACAAG ATTCATAAAG AAGAAACTGG
1101 AGTTACCGCA GGTGGGGGCG GCACAACGGC TATGGTAGAG CCGGTGCCAA
1151 TCACAGCTTC CTGTTGAAAA GGTTCACCTG AGGTGGATAT TCTTTTGAGT
1201 CATAAGACAT GTTGATTGTT GATGTTGTTT TCAAGAATGT TTCATCATTT
1251 CATGTGTTTT ATTAATCCTA AGTACAAATA ATTGCTGTCT ACGTACGTTC
1301 TTAGTTGCGA AAATTCTTGT TATTCTCTAT TGGGGTAAAA GTCTTCATGT
1351 TTATTGTAGT TGTGTTGGTT TTTCATATAT GCTATTTGCA ATAATGATTT
1401 TTGTGAAGCA CTTGTGGTGT ATTTACTTAC TACTGAAAAT AATGGTTACA
1451 CAAATATAT AAAAAAATAA AAATAAGCAA AAAAAAAAA AAAAAAAAA
1501 AAAAAAAAAA GTACTCTGCG TTGTTACCAC TGCTTAATCA CTAGTGAATT
1551 C
```

FIGURE 26

```
  1  MAPAATSSPT TPTTTKGRVL IVGGTGFIGK FVTEASLSTT HPTYLLVRPG
 51  PLLSSKAATI KAFQEKGAIV IYGRVNNKEF MEMILKKYEI NVVISAIGGS
101  DGLLEQLTLV EAMKSINTIK RFLPSEFGHD VDRANPVEPG LTMYKQKRLV
151  RRVIEESGVP YTYICCNSIA SWPYYDNCHP SQLPPPLDQL HIYGHGDVKA
201  YFVDGYDIGK FTMKVIDDER TINKNVHFRP SNNCYSMNEL ASLWENKIAR
251  KIPRVIVSED DLLAIAAENC IPESVVASIT HDIFINGCQV NFKVDGIHDV
301  EIGTLYPGES VRSLEECYEK FVVMAADKIH KEETGVTAGG GGTTAMVEPV
351  PITASC
```

FIGURE 27

```
   1 GAATTCGATT AAGCAGTGGT AACAACGCAG AGTACGCGGG GATACCAACA
  51 TTGTCACAAT TAACTCTAAA AGTAAAGCAA TGGCACCAGC AGCAACATCA
 101 TCACCAACCA CTCCCACTAC TACCAAGGGT CGTGTCCTAA TTGTTGGAGG
 151 AACAGGTTTC ATTGGAAAAT TTGTAACTGA GGCAAGTCTT TCCACAACAC
 201 ACCCAACCTA CTTGTTGGTT CGGCCAGGAC CTCTTCTCTC TTCTAAGGCT
 251 GCCACTATTA AGGCATTCCA AGAGAAAGGT GCCATTGTCA TTTATGGTCG
 301 GGTAAATAAT AAGGAGTTCA TGGAGATGAT TTTGAAAAAG TATGAGATAA
 351 ATGTAGTCAT TTCTGCAATA GGAGGCTCTG ATGGCTTGCT GGAACAGCTT
 401 ACTTTGGTGG AGGCCATGAA ATCTATTAAC ACCATTAAGA GGTTTTTGCC
 451 TTCGGAATTT GGTCACGATG TGGACAGAGC AGATCCTGTG GAACCTGGCC
 501 TAACAATGTA CAAACAGAAA CGTTTGGTTA GACGTGTGAT CGAAGAATCT
 551 GGTATACCAT ACACCTACAT CTGTTGCAAT TCGATCGCAT CTTGGCCGTA
 601 CTATGACAAT TGTCATCCAT CACAGCTTCC TCCACCGTTG GATCAATTAC
 651 ATATTTATGG TCATGGCGAT GTCAAAGCTT ACTTTGTTGA TGGCTATGAT
 701 ATTGGGAAAT TCACAATCAA GGTCATTGAT GATGAAAGAA CAATCAACAA
 751 AAATGTTCAT TTTCGACCTT CTAACAATTG TTATAGCATG AATGAGCTTG
 801 CTTCTTTGTG GGAAAACAAA ATTGCACGAA AAATTCCTAG AGTGATCGTC
 851 TCTGAAGACG ATCTTCTAGC AATAGCCGCA GAAAATTGCA TACCGGAAAG
 901 TGTCGTGGCA CCAATCACTC ATGATATATT CATCAATGGA TGTCAAGTTA
 951 ACTTCAAGAT AGATGGAATT CATGATGTTG AAATTGGCAC TCTATATCCT
1001 GGTGAATCGG TAAGAAGTTT GGAGGAATGC TATGAGAAAT TTGTTGTCAT
1051 GGCGGCTGAC AAGATTCATA AGAAGAAAC TGGAGTTACC GCAGGTGGGG
1101 GCGGCACAAC GGCTATGGTA GAGCCGGTGC CAATCACAGC TTCCTGTTGA
1151 AAAGGTTCAC CTGAGGTGGA TATTCTTTTG AGTCATAAGA CATGTTGATT
1201 GTTGATGTTG TTTTCAAGAA TGTTTCATCA TTTCATGTGT TTTATTAATC
1251 CTAAGTACAA ATAATTGCTG TCTACGTACG TTCTTAGTTG CAAAAATTCT
1301 TGTTATTCTC TATCAAAAAA AAAAAAAAAA AAAAAAAAAA AAAGTACTCT
1351 GCGTTGTTAC CACTGCTTAA TCACTAGTGA ATTC
```

FIGURE 30

```
  1  MAPAATSSPT TPTTTKGRVL IVGGTGFIGK FVTEASLSTT HPTYLLVRPG
 51  PLLSSKAATI KAFQEKGAIV IYGRVNNKEF MEMILKKYEI NVVISAIGGS
101  DGLLEQLTLV EAMKSINTIK RFLPSEFGHD VDRADPVEPG LTMYKQKRLV
151  RRVIEESGIP YTYICCNSIA SWPYYDNCHP SQLPPPLDQL HIYGHGDVKA
201  YFVDGYDIGK FTMKVIDDER TINKNVHFRP SNNCYSMNEL ASLWENKIAR
251  KIPRVIVSED DLLAIAAENC IPESVVAPIT HDIFINGCQV NFKIDGIHDV
301  EIGTLYPGES VRSLEECYEK FVVMAADKIH KEETGVTAGG GGTTAMVEPV
351  PITASC
```

FIGURE 31

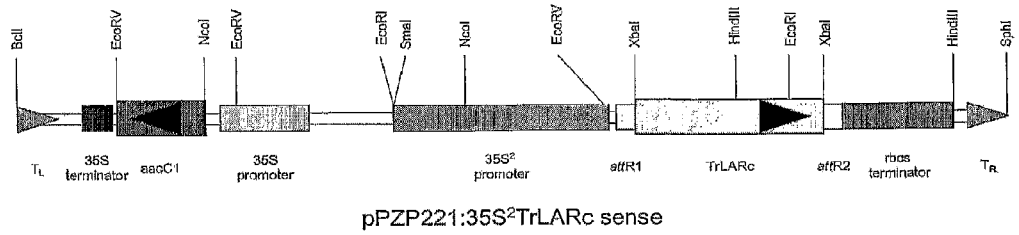
pPZP221:35S²TrLARc sense
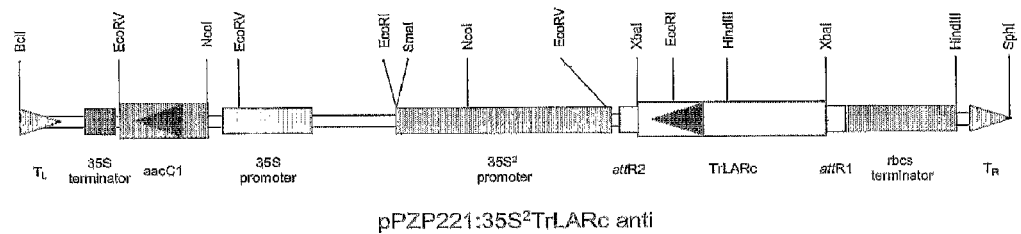
pPZP221:35S²TrLARc anti
FIGURE 32

SEQUENCE LISTING

```
<160> NUMBER OF SEQ ID NOS: 77

<210> SEQ ID NO 1
<211> LENGTH: 1447
<212> TYPE: DNA
<213> ORGANISM: Trifolium repens

<400> SEQUENCE: 1
gaattcacta gtgattaagc agtggtaaca acgcagagta cgcggggaac aaaaacaact      60
acgcatatta tatatatata tatatagtct ataattgaaa gaaactgcta aagatattat     120
taagatatgg tgagtgtagc tgaaattcgc aaggctcaga gggctgaagg ccctgcaacc     180
attttggcca ttggcactgc aaatccacca aaccgtgttg agcagagcac atatcctgat     240
ttctacttca aaattacaaa cagtgagcac aagactgagc tcaaagagaa gttccaacgc     300
atgtgtgaca aatccatgat caagagcaga tacatgtatc taacagaaga gattttgaaa     360
gaaaatccta gtctttgtga atacatggca ccttcattgg atgctaggca agacatggtg     420
gtggttgagg tacctagact tgggaaggag gctgcagtca aggccattaa agaatgggt      480 caaccaaagt caaagattac tcacttaatc ttttgcacca caagtggtgt tgacatgcct     540
ggtgctgatt accaactcac aaaactctta ggtcttcgcc catatgtgaa aaggtatatg     600
atgtaccaac aaggttgttt tgcaggaggc acggtgcttc gtttggcaaa agatttggcc     660
gagaacaaca aaggtgctcg tgtgctagtt gtttgttctg aagtcaccgc agtcacatttt    720
```

```
cgcggcccca gtgatactca cttggacagt cttgttggac aagcattgtt tggagatgga    780
gccgctgcac taattgttgg ttctgatcca gtgcctgaaa ttgagaaacc aatatttgag    840
atggtttgga ctgcacaaac aattgctcca gacagtgaag gtgccattga tggtcatctt    900
cgtgaagctg gctaacatt tcatcttctt aaagatgttc ctgggattgt atcaaagaac    960
attaataaag cattggttga ggctttccaa ccattaggaa tttctgacta caactcaatc   1020
ttttggattg cacacccggg tggacctgca attcttgatc aagtagaaca aaagctagcc   1080
ttgaagcccg aaaagatgag ggccacgagg gaagttctaa gtgaatatgg aaacatgtca   1140
agcgcatgtg tattgttcat cttagatgag atgcggaaga atcggctca aaatggactt    1200 aagacaactg gagaaggact tgattggggt gtgttgttcg gcttcggacc aggacttacc   1260
attgaaaccg ttgttcttcg tagcgtggct atataagatg tgtgattgtt tttattttaa   1320
tgtattactt ttaatcttgc tgccttgaat ttcgatttaa gaataaataa atatatcttt   1380
tgataaaaaa aaaaaaaaaa aaaaaaaaaa aagtactctg cgttgttacc actgcttaat   1440
cgaattc                                                             1447
```

<210> SEQ ID NO 2
<211> LENGTH: 389
<212> TYPE: PRT
<213> ORGANISM: Trifolium repens

<400> SEQUENCE: 2

```
Met Val Ser Val Ala Glu Ile Arg Lys Ala Gln Arg Ala Glu Gly Pro
1               5                   10                  15

Ala Thr Ile Leu Ala Ile Gly Thr Ala Asn Pro Pro Asn Arg Val Glu
            20                  25                  30

Gln Ser Thr Tyr Pro Asp Phe Tyr Phe Lys Ile Thr Asn Ser Glu His
        35                  40                  45

Lys Thr Glu Leu Lys Glu Lys Phe Gln Arg Met Cys Asp Lys Ser Met
    50                  55                  60

Ile Lys Ser Arg Tyr Met Tyr Leu Thr Glu Glu Ile Leu Lys Glu Asn
65                  70                  75                  80

Pro Ser Leu Cys Glu Tyr Met Ala Pro Ser Leu Asp Ala Arg Gln Asp
                85                  90                  95

Met Val Val Glu Val Pro Arg Leu Gly Lys Glu Ala Ala Val Lys
            100                 105                 110

Ala Ile Lys Glu Trp Gly Gln Pro Lys Ser Lys Ile Thr His Leu Ile
        115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Tyr Val Lys Arg Tyr Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Val Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ser Asp Pro Val Pro Glu Ile Glu Lys Pro Ile Phe Glu Met Val
225                 230                 235                 240
```

```
Trp Thr Ala Gln Thr Ile Ala Pro Asp Ser Glu Gly Ala Ile Asp Gly
                245                 250                 255

His Leu Arg Glu Ala Gly Leu Thr Phe His Leu Leu Lys Asp Val Pro
            260                 265                 270

Gly Ile Val Ser Lys Asn Ile Asn Lys Ala Leu Val Glu Ala Phe Gln
        275                 280                 285

Pro Leu Gly Ile Ser Asp Tyr Asn Ser Ile Phe Trp Ile Ala His Pro
    290                 295                 300

Gly Gly Pro Ala Ile Leu Asp Gln Val Glu Gln Lys Leu Ala Leu Lys
305                 310                 315                 320

Pro Glu Lys Met Arg Ala Thr Arg Glu Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Ala Gln Asn Gly Leu Lys Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

Arg Ser Val Ala Ile
385

<210> SEQ ID NO 3
<211> LENGTH: 2394
<212> TYPE: DNA
<213> ORGANISM: Trifolium repens

<400> SEQUENCE: 3
gaattcgatt aagcagtggt acaacgcag agtacgcggg gattcaatct gttgtgcata      60
aaattcactc attgcataga aaccataca catttgatct tgcaaagaag aaatatggga     120
gacgaaggta tagtgagagg tgtcacaaag cagacaaccc ctgggaaggc tactatattg     180
gctcttggca aggcattccc tcaccaactt gtgatgcaag agtgtttagt tgatggttat     240
tttagggaca ctaattgtga caatcctgaa cttaagcaga aacttgctag actttgtaag     300
acaaccacgg taaaaacaag gtatgttgtt atgaatgagg agatactaaa gaaatatcca     360
gaacttgttg tcgaaggcgc ctcaactgta aaacaacgtt tagagatatg taatgaggca     420
gtaacacaaa tggcaattga agcttcccaa gtttgcctaa agaattgggg tagatcctta     480
tcggacataa ctcatgtggt ttatgtttca tctagtgaag ctagattacc cggtggtgac     540
ctatacttgt caaaaggact aggactaaac cctaaaattc aagaaccat gctctatttc     600 tctggatgct cgggaggcgt agccggcctt cgcgttgcga aagacgtagc tgagaacaac     660
cctggaagta gagttttgct tgctacttcg gaaactacaa ttattggatt caagccacca     720
agtgttgata gaccttatga tcttgttggt gtggcactct ttggagatgg tgctggtgca     780
atgataattg gctcagaccc ggtatttgaa actgagacac cattgtttga gctgcatact     840
tcagctcagg agtttatacc agacaccgag aagaaaattg atgggcggct gacggaggag     900
ggcataagtt tcacactagc aagggaactt ccgcagataa tcgaagacaa tgttgaggga     960
ttctgtaata aactaattga tgttgttggg ttggagaata aggagtacaa taagttgttt    1020
tgggctgtgc atccaggtgg gcctgcgata ttgaatcgcg tggagaagcg gcttgagttg    1080
tcgccgcaga agctgaatgc tagtagaaaa gctctaatgg attatggaaa tgctagcagc    1140
aatactattg tttatgtgct ggaatatatg ctagaagagg aaaagaagat taaaaggcg    1200 ggtggaggag attctgaatg ggattgata cttgcttttg gacctggaat tacttttgag    1260
```

```
gggattctag caaggaactt gtgtgcatga agtcttatac aattgtgatg catgacttat    1320
actcttattt ctactaatta ttatattaag caaattcaga acttttaagt aatgatttaa    1380
tgaagaatac ttatagtata ttgactttat tcactttcaa agcaagttta tgatcctaag    1440
acatggtaga acttgagcat gtggaatagt tgtaacaaaa actctaagca aatagagact    1500
ttatgtagta taaagcattt ccagacatga taaataatgg tacctcagaa cataaaatat    1560
atttagctat ctttcatccc caactttaca catccaccaa ggtacagaat aagcatatgt    1620
caacacaaaa tgtactctaa gtctaacatg agtaaccaaa catgatgcct gattaagtta    1680
aaagaaaaga aaatctgagg gcatagatct tcaatcacac cactccagag ggaaggcgta    1740
gaacaagctg tccgccgaaa acactgcaat tcaataaata tcattaggac aacagtgcag    1800
agtcatgcgg gaaatgtctt aagtcactgt actaaaaata taggattata ttatgaacta    1860
tactaacctt ttcacataat agtaacagaa atcagctaag atgaatgtct ggacaatttc    1920
tgagataaga accatgacgg ccataagcca taccccaagg caaccaataa atgtccacgg    1980
gtatctaaca cctgttgcaa gaaatagtaa gttattagga gatgtgcggt tacgaaattc    2040
aagctacaca acaaaaggag gccagaacaa cagcaatctt gtaaccagat gacaacaata    2100
aaatgtaaac ttaaagagac cgaacacaca aacattgcaa ctcagatgga attgctgcca    2160
tgtaactagt aggagatttg ggacgtcaaa tcagtatatt atgcaaatac aaggtatgac    2220
cgccttgtct attgtagcat acaacaaacg tacagtgggt ttgtccctct caaaatggca    2280
ggatctttac agcacaatat ttggttttgt catacttata ccataaaaaa aaaaaaaaaa    2340 aaaaaaaaa aaagtactct gcgttgttac cactgcttaa tcactagtga attc          2394
```

<210> SEQ ID NO 4
<211> LENGTH: 391
<212> TYPE: PRT
<213> ORGANISM: Trifolium repens

<400> SEQUENCE: 4

```
Met Gly Asp Glu Gly Ile Val Arg Gly Val Thr Lys Gln Thr Thr Pro
1               5                   10                  15

Gly Lys Ala Thr Ile Leu Ala Leu Gly Lys Ala Phe Pro His Gln Leu
            20                  25                  30

Val Met Gln Glu Cys Leu Val Asp Gly Tyr Phe Arg Asp Thr Asn Cys
        35                  40                  45

Asp Asn Pro Glu Leu Lys Gln Lys Leu Ala Arg Leu Cys Lys Thr Thr
    50                  55                  60

Thr Val Lys Thr Arg Tyr Val Val Met Asn Glu Glu Ile Leu Lys Lys
65                  70                  75                  80

Tyr Pro Glu Leu Val Val Glu Gly Ala Ser Thr Val Lys Gln Arg Leu
                85                  90                  95

Glu Ile Cys Asn Glu Ala Val Thr Gln Met Ala Ile Glu Ala Ser Gln
            100                 105                 110

Val Cys Leu Lys Asn Trp Gly Arg Ser Leu Ser Asp Ile Thr His Val
        115                 120                 125

Val Tyr Val Ser Ser Glu Ala Arg Leu Pro Gly Gly Asp Leu Tyr
    130                 135                 140

Leu Ser Lys Gly Leu Gly Leu Asn Pro Lys Ile Gln Arg Thr Met Leu
145                 150                 155                 160

Tyr Phe Ser Gly Cys Ser Gly Gly Val Ala Gly Leu Arg Val Ala Lys
                165                 170                 175
```

```
Asp Val Ala Glu Asn Asn Pro Gly Ser Arg Val Leu Leu Ala Thr Ser
            180                 185                 190

Glu Thr Thr Ile Ile Gly Phe Lys Pro Pro Ser Val Asp Arg Pro Tyr
        195                 200                 205

Asp Leu Val Gly Val Ala Leu Phe Gly Asp Gly Ala Gly Ala Met Ile
    210                 215                 220

Ile Gly Ser Asp Pro Val Phe Glu Thr Glu Thr Pro Leu Phe Glu Leu
225                 230                 235                 240

His Thr Ser Ala Gln Glu Phe Ile Pro Asp Thr Glu Lys Lys Ile Asp
                245                 250                 255

Gly Arg Leu Thr Glu Glu Gly Ile Ser Phe Thr Leu Ala Arg Glu Leu
            260                 265                 270

Pro Gln Ile Ile Glu Asp Asn Val Glu Gly Phe Cys Asn Lys Leu Ile
        275                 280                 285

Asp Val Val Gly Leu Glu Asn Lys Glu Tyr Asn Lys Leu Phe Trp Ala
    290                 295                 300

Val His Pro Gly Gly Pro Ala Ile Leu Asn Arg Val Glu Lys Arg Leu
305                 310                 315                 320

Glu Leu Ser Pro Gln Lys Leu Asn Ala Ser Arg Lys Ala Leu Met Asp
                325                 330                 335

Tyr Gly Asn Ala Ser Ser Asn Thr Ile Val Tyr Val Leu Glu Tyr Met
            340                 345                 350

Leu Glu Glu Glu Lys Lys Ile Lys Lys Ala Gly Gly Asp Ser Glu
        355                 360                 365

Trp Gly Leu Ile Leu Ala Phe Gly Pro Gly Ile Thr Phe Glu Gly Ile
    370                 375                 380

Leu Ala Arg Asn Leu Cys Ala
385                 390

<210> SEQ ID NO 5
<211> LENGTH: 1653
<212> TYPE: DNA
<213> ORGANISM: Trifolium repens

<400> SEQUENCE: 5
gaattcgatt aagcagtggt aacaacgcag agtacgcggg actaagcctt gattcattgt      60
ttgtttccat aacacaagaa ctagtgtttg cttgaatctt aagaaaaaat gcctcaaggt     120
gatttgaatg gaagttcctc ggtgaatgga gcacgtgcta gacgtgctcc tactcaggga     180
aaggcaacga tacttgcatt aggaaaggct ttccccgccc aggtcctccc tcaagagtgc     240
ttggtggaag gattcattcg cgacactaag tgtgacgata cttatattaa ggagaaattg     300
gagcgtcttt gcaaaaacac aactgtgaaa acaagataca cagtaatgtc aaaggagatc     360
ttagacaact atccagagct agccatagat ggaacaccaa caataaggca aaagcttgaa     420
atagcaaatc cagcagtagt tgaaatggca acaagagcaa gcaaagattg catcaaagaa     480
tggggaaggt cacctcaaga tatcacacac atagtctatg tttcctcgag cgaaattcgt     540
ctacccggtg gtgacccttta tcttgcaaat gaactcggct taaacagcga tgttaatcgc     600
gtaatgctct atttcctcgg ttgctacggc ggtgtcactg gcttacgtgt cgccaaagac     660
atcgccgaaa ataaccctgg tagtagggtg ttactcacaa catccgagac cactattctc     720
ggttttcgac caccgagtaa agctagacct tatgacctcg ttggcgctgc acttttcggt     780
gatggcgccg ctgctgcaat aattggaaca gaccctatat gaatcaaga atcacctttc     840
```

```
atggaattga accatgcagt ccaaaaattc ttgcctgata cacaaaatgt gattgatggt      900
agaatcactg aagagggtat taattttaag cttggaagag accttcctca aaaaattgaa      960
gacaatattg aagaattttg caagaaaatt atggctaaaa gtgatgttaa ggaatttaat     1020
gacttatttt gggctgttca tcctggtggg ccagctatac tcaataagct agaaaatata     1080
ctcaaattga aaagtgataa attggattgt agtaggaagg cattaatgga ttatggaaat     1140
gttagtagca atactatatt ctatgtgatg gagtatatga gagattattt gaaggaagat     1200
ggaagtgaag aatggggatt aggattggct tttggaccag ggattacttt tgaaggggtt     1260
ctcctccgta gcctttaatc ttgaaataat aattcatatg aaattacttg tcttaagatt     1320
gtgataggaa gatgaatatg tattggatta atattgatat ggtgttattt taagttgatt     1380
ttaaaaaaag tttattaata aagtatgatg taacaattgt tgtttgaatg ttaaaaggga     1440
agtatactat tttaagttct tgaccatact gatttttct ttacacatttt tcatatctaa      1500 aattgttcta tgatatcttc attgttgata ctgtaataat ataatatcta atttggctgg     1560
caaaatgaaa gattttcac cgaaaaaaaa aaaaaaaaa aaaaaaaaa aagtactctg       1620 cgttgttacc actgcttaat cactagtgaa ttc                                 1653
```

<210> SEQ ID NO 6
<211> LENGTH: 389
<212> TYPE: PRT
<213> ORGANISM: Trifolium repens

<400> SEQUENCE: 6

```
Met Pro Gln Gly Asp Leu Asn Gly Ser Ser Val Asn Gly Ala Arg
1               5                   10                  15

Ala Arg Arg Ala Pro Thr Gln Gly Lys Ala Thr Ile Leu Ala Leu Gly
            20                  25                  30

Lys Ala Phe Pro Ala Gln Val Leu Pro Gln Glu Cys Leu Val Glu Gly
        35                  40                  45

Phe Ile Arg Asp Thr Lys Cys Asp Asp Thr Tyr Ile Lys Glu Lys Leu
    50                  55                  60

Glu Arg Leu Cys Lys Asn Thr Thr Val Lys Thr Arg Tyr Thr Val Met
65                  70                  75                  80

Ser Lys Glu Ile Leu Asp Asn Tyr Pro Glu Leu Ala Ile Asp Gly Thr
                85                  90                  95

Pro Thr Ile Arg Gln Lys Leu Glu Ile Ala Asn Pro Ala Val Val Glu
            100                 105                 110

Met Ala Thr Arg Ala Ser Lys Asp Cys Ile Lys Glu Trp Gly Arg Ser
        115                 120                 125

Pro Gln Asp Ile Thr His Ile Val Tyr Val Ser Ser Ser Glu Ile Arg
    130                 135                 140

Leu Pro Gly Gly Asp Leu Tyr Leu Ala Asn Glu Leu Gly Leu Asn Ser
145                 150                 155                 160

Asp Val Asn Arg Val Met Leu Tyr Phe Leu Gly Cys Tyr Gly Gly Val
                165                 170                 175

Thr Gly Leu Arg Val Ala Lys Asp Ile Ala Glu Asn Asn Pro Gly Ser
            180                 185                 190

Arg Val Leu Leu Thr Thr Ser Glu Thr Thr Ile Leu Gly Phe Arg Pro
        195                 200                 205

Pro Ser Lys Ala Arg Pro Tyr Asp Leu Val Gly Ala Ala Leu Phe Gly
    210                 215                 220

Asp Gly Ala Ala Ala Ala Ile Ile Gly Thr Asp Pro Ile Leu Asn Gln
```

```
                225                 230                 235                 240
Glu Ser Pro Phe Met Glu Leu Asn His Ala Val Gln Lys Phe Leu Pro
                    245                 250                 255

Asp Thr Gln Asn Val Ile Asp Gly Arg Ile Thr Glu Glu Gly Ile Asn
                260                 265                 270

Phe Lys Leu Gly Arg Asp Leu Pro Gln Lys Ile Glu Asp Asn Ile Glu
            275                 280                 285

Glu Phe Cys Lys Lys Ile Met Ala Lys Ser Asp Val Lys Glu Phe Asn
        290                 295                 300

Asp Leu Phe Trp Ala Val His Pro Gly Gly Pro Ala Ile Leu Asn Lys
305                 310                 315                 320

Leu Glu Asn Ile Leu Lys Leu Lys Ser Asp Lys Leu Asp Cys Ser Arg
                325                 330                 335

Lys Ala Leu Met Asp Tyr Gly Asn Val Ser Ser Asn Thr Ile Phe Tyr
                340                 345                 350

Val Met Glu Tyr Met Arg Asp Tyr Leu Lys Glu Asp Gly Ser Glu Glu
            355                 360                 365

Trp Gly Leu Gly Leu Ala Phe Gly Pro Gly Ile Thr Phe Glu Gly Val
        370                 375                 380

Leu Leu Arg Ser Leu
385

<210> SEQ ID NO 7
<211> LENGTH: 1600
<212> TYPE: DNA
<213> ORGANISM: Trifolium repens

<400> SEQUENCE: 7
gaattcacta gtgattaagc agtggtaaca acgcagagta cgcggggaa tccaccaaat     60
caacaccatt aataaccttc caaattctcg ttacctcacc aaatctcatt tttcattata    120
tatcttgggt acatcttttg ttacctccaa caaaaaaatg gtgaccgtag aagagattcg    180
taacgcccaa cgttcaaatg gccctgccac tatcttagct tttggcacag ccactccttc    240
taactgtgtc actcaagctg attatcctga ttactacttt cgtatcacca acagcgaaca    300
tatgactgat cttaaggaaa aattcaagcg gatgtgtgat agatcaatga taaagaaacg    360
ttacatgcac ctaacagaag actttctgaa ggagaatcca aatatgtgtg aatacatggc    420
accatcacta gatgtaagac gagacatagt ggttgttgaa gtaccaaagc taggtaaaga    480
agcagcaaaa aaagccatat gtgaatgggg acaaccaaaa tccaaaatca cacatcttgt    540
tttctgcacc acttccggtg ttgacatgcc gggagccgat taccaactca ccaaactttt    600
aggcttaaaa ccttctgtca agcgtctcat gatgtatcaa caaggttgtt tcgctggcgg    660
cacagttctc cgcttagcaa aagaccttgt tgagaataac aaaaatgcaa gagttcttgt    720
tgtttgttct gaaattactg cggttacttt tcgtggacca tcggatactc atcttgattc    780
gctcgtggga caggcgcttt tggtgatgga agccgcagca atgattattg gtgcggatcc    840
tgatttaacc gtggagcgtc cgattttcga gattgtttcg gctgctcaga ctattcttcc    900
tgattctgat ggcgcaattg atggacatct tcgtgaagtg gggctcactt ttcatttatt    960
gaaagatgtt ccggggatta tttcaaagaa cattgaaaaa gtttagttg aagcttttgc   1020
gcctattggg attaatgatt ggaactcaat attttgggtt gcacatccag gtggaccggc   1080
tattttagac caggttgaag agaaactcca tcttaaagag gagaaactcc ggtccacccg   1140
gcatgtgctt agtgaatatg gaaatatgtc aagtgcatgt gttttattta ttttggatga   1200
```

-continued

```
aatgagaaag aggtctaaag aggaagggat gattacaact ggtgaagggt tggaatgggg    1260
tgtgttgttt gggtttggac cgggtttaac tgttgaaacc gttgtgcttc atagtgttcc    1320
ggttcagggt tgaatttatt atacatagat tggaaaataa aatttgcctg ccgagagatg    1380
tgaactaact ttgtaggcaa gctcaaatta aagtttgaga taatattgtg ctttagttat    1440
tatggtatgt aatgtaatgt ttttactttt ttcgaaattc atgtaatttg atatgtaaag    1500
taatatgttt gggttggaat ataattattg gttaactaaa aaaaaaaaaa aaaaaaaaa     1560 aaaaagtact ctgcgttgtt accactgctt aatcgaattc                          1600
```

<210> SEQ ID NO 8
<211> LENGTH: 391
<212> TYPE: PRT
<213> ORGANISM: Trifolium repens

<400> SEQUENCE: 8

Met Val Thr Val Glu Glu Ile Arg Asn Ala Gln Arg Ser Asn Gly Pro
1               5                   10                  15

Ala Thr Ile Leu Ala Phe Gly Thr Ala Thr Pro Ser Asn Cys Val Thr
            20                  25                  30

Gln Ala Asp Tyr Pro Asp Tyr Tyr Phe Arg Ile Thr Asn Ser Glu His
        35                  40                  45

Met Thr Asp Leu Lys Glu Lys Phe Lys Arg Met Cys Asp Arg Ser Met
50                  55                  60

Ile Lys Lys Arg Tyr Met His Leu Thr Glu Asp Phe Leu Lys Glu Asn
65                  70                  75                  80

Pro Asn Met Cys Glu Tyr Met Ala Pro Ser Leu Asp Val Arg Arg Asp
                85                  90                  95

Ile Val Val Val Glu Val Pro Lys Leu Gly Lys Glu Ala Ala Lys Lys
            100                 105                 110

Ala Ile Cys Glu Trp Gly Gln Pro Lys Ser Lys Ile Thr His Leu Val
        115                 120                 125

Phe Cys Thr Thr Ser Gly Val Asp Met Pro Gly Ala Asp Tyr Gln Leu
    130                 135                 140

Thr Lys Leu Leu Gly Leu Lys Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Val Glu Asn Asn Lys Asn Ala Arg Val Leu Val Val Cys Ser Glu
            180                 185                 190

Ile Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Met Ile Ile
    210                 215                 220

Gly Ala Asp Pro Asp Leu Thr Val Glu Arg Pro Ile Phe Glu Ile Val
225                 230                 235                 240

Ser Ala Ala Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
            260                 265                 270

Gly Ile Ile Ser Lys Asn Ile Glu Lys Ser Leu Val Glu Ala Phe Ala
        275                 280                 285

Pro Ile Gly Ile Asn Asp Trp Asn Ser Ile Phe Trp Val Ala His Pro
    290                 295                 300

Gly Gly Pro Ala Ile Leu Asp Gln Val Glu Glu Lys Leu His Leu Lys
305                 310                 315                 320

Glu Glu Lys Leu Arg Ser Thr Arg His Val Leu Ser Glu Tyr Gly Asn
            325                 330                 335

Met Ser Ser Ala Cys Val Leu Phe Ile Leu Asp Glu Met Arg Lys Arg
                340                 345                 350

Ser Lys Glu Glu Gly Met Ile Thr Thr Gly Glu Gly Leu Glu Trp Gly
        355                 360                 365

Val Leu Phe Gly Phe Gly Pro Gly Leu Thr Val Glu Thr Val Val Leu
    370                 375                 380

His Ser Val Pro Val Gln Gly
385                 390

<210> SEQ ID NO 9
<211> LENGTH: 1309
<212> TYPE: DNA
<213> ORGANISM: Trifolium repens

<400> SEQUENCE: 9
gaattcgatt aagcagtggt aacaacgcag agtacgcggg ataaaaactg cactagtgtg    60
tataagtttc ttggtgaaaa aagagtttgt aaattaacat catggctagt atcaaacaaa   120
ttggaaacaa gaaagcatgt gtgattggtg gcactggttt tgttgcatct atgttgatca   180
agcagttact tgaaaagggt tatgctgtta atactaccgt tagagaccca gatagcccta   240
agaaaatatc tcacctagtg gcactgcaaa gtttggggga actgaatcta tttagagcag   300
acttaacagt tgaagaagat tttgatgctc ctatagcagg atgtgaactt gtttttcaac   360
ttgctacacc tgtgaacttt gcttctcaag atcctgagaa tgacatgata aagccagcaa   420 tcaaggtgt gttgaatgtg ttgaaagcaa ttgcaagagc aaaagaagtt aaaagagtta   480
tcttaacatc ttcggcagcc gcggtgacta taaatgaact caagggaca ggtcatgtta   540 tggatgaaac caactggtct gatgttgaat ttctcaacac tgcaaaacca cccacttggg   600
gttatcctgc ctcaaaaatg ctagctgaaa aggctgcatg gaaatttgct gaagaaaatg   660
acattgatct aatcactgtg atacctagtt taacaactgg tccttctctc acaccagata   720
tcccatctag tgttggcttg gcaatgtctc taataacagg caatgatttt ctcataaatg   780 cttttgaaagg aatgcagttt ctgtcgggtt cgttatccat cactcatgtt gaggatattt   840
gccgagctca tatatttctt gcagagaaag aatcagcttc tggtagatac atttgctgtg   900
ctcacaatac tagtgttccc gagcttgcaa agtttctcaa caacgatat cctcagtata   960 aagttccaac tgaatttgat gattgcccca gcaaggcaaa gttgataatc tcttctgaaa  1020
agcttatcaa agaagggttc agtttcaagc atggtattgc cgaaactttc gaccagactg  1080
tcgagtattt taagactaag ggggcactga agaattagat tttgatattt ctaattcaat  1140
agcaaactct aagcttgtta tgtgtttgtg aagttcagag tgaaatatca aatgaataag  1200
tggagagagc acaataagag gagagcacaa taattttgga aaaaaaaaa aaaaaaaaa   1260 aaaaaaagt actctgcgtt gttaccactg cttaatcact agtgaattc              1309

<210> SEQ ID NO 10
<211> LENGTH: 338
<212> TYPE: PRT
<213> ORGANISM: Trifolium repens

<400> SEQUENCE: 10

Met Ala Ser Ile Lys Gln Ile Gly Asn Lys Ala Cys Val Ile Gly
1               5                   10                  15

Gly Thr Gly Phe Val Ala Ser Met Leu Ile Lys Gln Leu Leu Glu Lys
            20                  25                  30

Gly Tyr Ala Val Asn Thr Thr Val Arg Asp Pro Asp Ser Pro Lys Lys
            35                  40                  45

Ile Ser His Leu Val Ala Leu Gln Ser Leu Gly Glu Leu Asn Leu Phe
        50                  55                  60

Arg Ala Asp Leu Thr Val Glu Glu Asp Phe Ala Pro Ile Ala Gly
65                  70                  75                  80

Cys Glu Leu Val Phe Gln Leu Ala Thr Pro Val Asn Phe Ala Ser Gln
                85                  90                  95

Asp Pro Glu Asn Asp Met Ile Lys Pro Ala Ile Lys Gly Val Leu Asn
            100                 105                 110

Val Leu Lys Ala Ile Ala Arg Ala Lys Glu Val Lys Arg Val Ile Leu
        115                 120                 125

Thr Ser Ser Ala Ala Ala Val Thr Ile Asn Glu Leu Lys Gly Thr Gly
        130                 135                 140

His Val Met Asp Glu Thr Asn Trp Ser Asp Val Glu Phe Leu Asn Thr
145                 150                 155                 160

Ala Lys Pro Pro Thr Trp Gly Tyr Pro Ala Ser Lys Met Leu Ala Glu
                165                 170                 175

Lys Ala Ala Trp Lys Phe Ala Glu Glu Asn Asp Ile Asp Leu Ile Thr
            180                 185                 190

Val Ile Pro Ser Leu Thr Thr Gly Pro Ser Leu Thr Pro Asp Ile Pro
        195                 200                 205

Ser Ser Val Gly Leu Ala Met Ser Leu Ile Thr Gly Asn Asp Phe Leu
210                 215                 220

Ile Asn Ala Leu Lys Gly Met Gln Phe Leu Ser Gly Ser Leu Ser Ile
225                 230                 235                 240

Thr His Val Glu Asp Ile Cys Arg Ala His Ile Phe Leu Ala Glu Lys
                245                 250                 255

Glu Ser Ala Ser Gly Arg Tyr Ile Cys Cys Ala His Asn Thr Ser Val
            260                 265                 270

Pro Glu Leu Ala Lys Phe Leu Asn Lys Arg Tyr Pro Gln Tyr Lys Val
        275                 280                 285

Pro Thr Glu Phe Asp Asp Cys Pro Ser Lys Ala Lys Leu Ile Ile Ser
        290                 295                 300

Ser Glu Lys Leu Ile Lys Glu Gly Phe Ser Phe Lys His Gly Ile Ala
305                 310                 315                 320

Glu Thr Phe Asp Gln Thr Val Glu Tyr Phe Lys Thr Lys Gly Ala Leu
                325                 330                 335

Lys Asn

<210> SEQ ID NO 11
<211> LENGTH: 1409
<212> TYPE: DNA
<213> ORGANISM: Trifolium repens

<400> SEQUENCE: 11
gaattcgatt aagcagtggt aacaacgcag agtacgcggg gataccaaca ttgtcacaat       60
taactctaaa agcaaagcaa tggcaccagc agcaacatca tcaccaacca ctcctactac      120
taccaagggt cgtgtcctaa ttgttggagg aacaggtttc attggaaaat tgtaactga       180

```
ggcaagtctt tccacaacac acccaaccta cttgttggtt cggccaggac ctcttctctc      240
ttctaaggct gccactatta aggcattcca agagaaaggt gccattgtca tttatggtcg      300
ggtaaataat aaggagttca tggagatgat tttgaaaaag tatgagataa atgtagtcat      360
ttctgcaata ggaggctctg atggcttgct ggaacagctt actttggtgg aggccatgaa      420
atctattaac accattaaga ggttttttgcc ttcggaattt ggtcacgatg tggacagagc     480
aaatcctgtg gaacctggcc taacaatgta caaacagaaa cgtttggtta gacgtgtgat      540
cgaagaatct ggtataccat acacctacat ctgttgcaat tcgatcgcat cttggccgta      600
ctatgacaat tgtcatccat cacagcttcc tccaccgttg gatcaattac atatttatgg      660
tcatggcgat gtcaaagctt actttgttga tggctatgat attgggaaat tcacaatgaa      720
ggtcattgat gatgaaagaa caatcaacaa aatgttcat tttcgacctt ctaacaattg       780
ttatagcatg aatgagcttg cttctttgtg ggaaaacaaa attgcacgaa aaattcctag      840
agtgatcgtc tctgaagacg atcttctagc aatagccgca gaaaattgca taccggaaag      900
tgtcgtggca ccaatcactc atgatatatt catcaatgga tgtcaagtta acttcaagat      960
agatggaatt catgatgttg aaattggcac tctatatcct ggtgaatcgg taagaagttt     1020
ggaggaatgc tatgagaaat tgttgtcat ggcggctgac aagattcata agaagaaac      1080 tggagttacc gcaggtgggg gcggcacaac ggctatggta gagccggtgc caatcacagc     1140
ttcctgttga aaaggttcac ctgaggtgga tattcttttg agtcataaga catgttgatt     1200
gttgatgttg ttttcaagaa tgtttcatca tttcatgtgt tttattaatc ctaagtacaa     1260
ataattgctc tctacgtacg ttcttagttg caaaaattct tgttattctc tattgaggta     1320
aaagtcttca tgtttacaaa aaaaaaaaaa aaaaaaaaa aaaaaaagt actctgcgtt       1380 gttaccactg cttaatcact agtgaattc                                       1409
```

<210> SEQ ID NO 12
<211> LENGTH: 356
<212> TYPE: PRT
<213> ORGANISM: Trifolium repens

<400> SEQUENCE: 12

```
Met Ala Pro Ala Ala Thr Ser Ser Pro Thr Thr Pro Thr Thr Thr Lys
1               5                   10                  15

Gly Arg Val Leu Ile Val Gly Thr Gly Phe Ile Gly Lys Phe Val
            20                  25                  30

Thr Glu Ala Ser Leu Ser Thr Thr His Pro Thr Tyr Leu Leu Val Arg
        35                  40                  45

Pro Gly Pro Leu Leu Ser Ser Lys Ala Ala Thr Ile Lys Ala Phe Gln
    50                  55                  60

Glu Lys Gly Ala Ile Val Ile Tyr Gly Arg Val Asn Asn Lys Glu Phe
65                  70                  75                  80

Met Glu Met Ile Leu Lys Lys Tyr Glu Ile Asn Val Val Ile Ser Ala
                85                  90                  95

Ile Gly Gly Ser Asp Gly Leu Leu Glu Gln Leu Thr Leu Val Glu Ala
            100                 105                 110

Met Lys Ser Ile Asn Thr Ile Lys Arg Phe Leu Pro Ser Glu Phe Gly
        115                 120                 125

His Asp Val Asp Arg Ala Asn Pro Val Glu Pro Gly Leu Thr Met Tyr
    130                 135                 140

Lys Gln Lys Arg Leu Val Arg Arg Val Ile Glu Glu Ser Gly Ile Pro
145                 150                 155                 160
```

```
Tyr Thr Tyr Ile Cys Cys Asn Ser Ile Ala Ser Trp Pro Tyr Tyr Asp
                165                 170                 175

Asn Cys His Pro Ser Gln Leu Pro Pro Leu Asp Gln Leu His Ile
        180                 185                 190

Tyr Gly His Gly Asp Val Lys Ala Tyr Phe Val Asp Gly Tyr Asp Ile
            195                 200                 205

Gly Lys Phe Thr Met Lys Val Ile Asp Asp Glu Arg Thr Ile Asn Lys
        210                 215                 220

Asn Val His Phe Arg Pro Ser Asn Asn Cys Tyr Ser Met Asn Glu Leu
225                 230                 235                 240

Ala Ser Leu Trp Glu Asn Lys Ile Ala Arg Lys Ile Pro Arg Val Ile
                245                 250                 255

Val Ser Glu Asp Asp Leu Leu Ala Ile Ala Ala Glu Asn Cys Ile Pro
            260                 265                 270

Glu Ser Val Val Ala Pro Ile Thr His Asp Ile Phe Ile Asn Gly Cys
        275                 280                 285

Gln Val Asn Phe Lys Ile Asp Gly Ile His Asp Val Glu Ile Gly Thr
    290                 295                 300

Leu Tyr Pro Gly Glu Ser Val Arg Ser Leu Glu Glu Cys Tyr Glu Lys
305                 310                 315                 320

Phe Val Val Met Ala Ala Asp Lys Ile His Lys Glu Glu Thr Gly Val
                325                 330                 335

Thr Ala Gly Gly Gly Gly Thr Thr Ala Met Val Glu Pro Val Pro Ile
            340                 345                 350

Thr Ala Ser Cys
        355

<210> SEQ ID NO 13
<211> LENGTH: 1551
<212> TYPE: DNA
<213> ORGANISM: Trifolium repens

<400> SEQUENCE: 13
gaattcgatt aagcagtggt aacaacgcag agtacgcggg aggatccttc cattttgcat    60
accaacattg tcacaattaa ctctaaaagc aaagcaatgg caccagcagc aacatcatca   120
ccaaccactc ctactactac caagggtcgt gtcctaattg ttggaggaac aggtttcatt   180 ggaaatttg taactgaggc aagtctttcc acaacacacc caacctactt gttggttcgg   240
ccaggacctc ttctctcttc taaggctgcc actattaagg cattccaaga gaaaggtgcc   300
attgtcattt atggtcgggt aaataataag gagttcatgg agatgatttt gaaaaagtat   360
gagataaatg tagtcatttc tgcaatagga ggctctgatg gcttgctgga cagcttact   420 ttggtggagg ccatgaaatc tattaacacc attaagaggt ttttgccttc agaatttggt   480
cacgatgtgg acagagcaaa tcctgtggaa cctggcctaa caatgtacaa acagaaacgt   540
ttggttagac gtgtgatcga agaatctggt gtaccataca cctacatctg ttgcaattcg   600
atcgcatcct ggccgtacta tgacaattgt catccatcac agcttcctcc accgttggat   660
caattacata tttatggtca tggcgatgtc aaagcttact tgttgatgg ctatgatatt   720 gggaaattca caatgaaggt cattgatgat gaaagaacaa tcaacaaaaa tgttcatttt   780
cgaccttcta caattgttta gcatgaatg agcttgcttt ctttgtggga aaacaaaatt   840
gcacgaaaaa ttcctagagt gatcgtctct gaagacgatc ttctagcaat agccgcagaa   900
aactgcatac cggaaagtgt tgtggcatca atcactcatg atatattcat caatggatgt   960
```

```
caagttaact tcaaggtaga tggaattcat gatgttgaaa ttggcactct atatcctggt    1020
gaatcggtaa aagtttgga ggaatgctat gagaaatttg ttgtcatggc ggctgacaag    1080
attcataaag aagaaactgg agttaccgca ggtggggcg gcacaacggc tatggtagag    1140
ccggtgccaa tcacagcttc ctgttgaaaa ggttcacctg aggtggatat tcttttgagt    1200
cataagacat gttgattgtt gatgttgttt tcaagaatgt ttcatcattt catgtgtttt    1260
attaatccta agtacaaata attgctgtct acgtacgttc ttagttgcga aaattcttgt    1320
tattctctat tggggtaaaa gtcttcatgt ttattgtagt tgtgttggtt tttcatatat    1380
gctatttgca ataatgattt ttgtgaagca cttgtggtgt atttacttac tactgaaaat    1440
aatggttaca caaatatat aaaaaaataa aaataagcaa aaaaaaaaa aaaaaaaaa      1500 aaaaaaaaaa gtactctgcg ttgttaccac tgcttaatca ctagtgaatt c            1551
```

<210> SEQ ID NO 14
<211> LENGTH: 356
<212> TYPE: PRT
<213> ORGANISM: Trifolium repens

<400> SEQUENCE: 14

```
Met Ala Pro Ala Ala Thr Ser Ser Pro Thr Thr Pro Thr Thr Thr Lys
1               5                   10                  15

Gly Arg Val Leu Ile Val Gly Gly Thr Gly Phe Ile Gly Lys Phe Val
            20                  25                  30

Thr Glu Ala Ser Leu Ser Thr Thr His Pro Thr Tyr Leu Leu Val Arg
        35                  40                  45

Pro Gly Pro Leu Leu Ser Ser Lys Ala Ala Thr Ile Lys Ala Phe Gln
    50                  55                  60

Glu Lys Gly Ala Ile Val Ile Tyr Gly Arg Val Asn Asn Lys Glu Phe
65                  70                  75                  80

Met Glu Met Ile Leu Lys Lys Tyr Glu Ile Asn Val Val Ile Ser Ala
                85                  90                  95

Ile Gly Gly Ser Asp Gly Leu Leu Glu Gln Leu Thr Leu Val Glu Ala
            100                 105                 110

Met Lys Ser Ile Asn Thr Ile Lys Arg Phe Leu Pro Ser Glu Phe Gly
        115                 120                 125

His Asp Val Asp Arg Ala Asn Pro Val Glu Pro Gly Leu Thr Met Tyr
    130                 135                 140

Lys Gln Lys Arg Leu Val Arg Arg Val Ile Glu Ser Gly Val Pro
145                 150                 155                 160

Tyr Thr Tyr Ile Cys Cys Asn Ser Ile Ala Ser Trp Pro Tyr Tyr Asp
                165                 170                 175

Asn Cys His Pro Ser Gln Leu Pro Pro Leu Asp Gln Leu His Ile
            180                 185                 190

Tyr Gly His Gly Asp Val Lys Ala Tyr Phe Val Asp Gly Tyr Asp Ile
        195                 200                 205

Gly Lys Phe Thr Met Lys Val Ile Asp Asp Glu Arg Thr Ile Asn Lys
    210                 215                 220

Asn Val His Phe Arg Pro Ser Asn Asn Cys Tyr Ser Met Asn Glu Leu
225                 230                 235                 240

Ala Ser Leu Trp Glu Asn Lys Ile Ala Arg Lys Ile Pro Arg Val Ile
                245                 250                 255

Val Ser Glu Asp Asp Leu Leu Ala Ile Ala Ala Glu Asn Cys Ile Pro
            260                 265                 270
```

Glu Ser Val Ala Ser Ile Thr His Asp Ile Phe Ile Asn Gly Cys
        275                 280                 285

Gln Val Asn Phe Lys Val Asp Gly Ile His Asp Val Glu Ile Gly Thr
    290                 295                 300

Leu Tyr Pro Gly Glu Ser Val Arg Ser Leu Glu Glu Cys Tyr Glu Lys
305                 310                 315                 320

Phe Val Val Met Ala Ala Asp Lys Ile His Lys Glu Glu Thr Gly Val
                325                 330                 335

Thr Ala Gly Gly Gly Thr Thr Ala Met Val Glu Pro Val Pro Ile
            340                 345                 350

Thr Ala Ser Cys
        355

<210> SEQ ID NO 15
<211> LENGTH: 1384
<212> TYPE: DNA
<213> ORGANISM: Trifolium repens

<400> SEQUENCE: 15
gaattcgatt aagcagtggt aacaacgcag agtacgcggg gataccaaca ttgtcacaat      60
taactctaaa agtaaagcaa tggcaccagc agcaacatca tcaccaacca ctcccactac    120
taccaagggt cgtgtcctaa ttgttggagg aacaggtttc attggaaaat tgtaactga    180 ggcaagtctt ccacaacac acccaaccta cttgttggtt cggccaggac ctcttctctc    240
ttctaaggct gccactatta aggcattcca agagaaaggt gccattgtca tttatggtcg    300
ggtaaataat aaggagttca tggagatgat tttgaaaaag tatgagataa atgtagtcat    360
ttctgcaata ggaggctctg atggcttgct ggaacagctt actttggtgg aggccatgaa    420
atctattaac accattaaga ggttttttgcc ttcggaattt ggtcacgatg tggacagagc    480
agatcctgtg gaacctggcc taacaatgta caaacagaaa cgtttggtta gacgtgtgat    540
cgaagaatct ggtataccat acacctacat ctgttgcaat tcgatcgcat cttggccgta    600
ctatgacaat tgtcatccat cacagcttcc tccaccgttg gatcaattac atatttatgg    660
tcatggcgat gtcaaagctt actttgttga tggctatgat attgggaaat tcacaatgaa    720
ggtcattgat gatgaaagaa caatcaacaa aaatgttcat tttcgacctt ctaacaattg    780
ttatagcatg aatgagcttg cttcttttgtg ggaaaacaaa attgcacgaa aaattcctag    840
agtgatcgtc tctgaagacg atcttctagc aatagccgca gaaaattgca taccggaaag    900
tgtcgtggca ccaatcactc atgatatatt catcaatgga tgtcaagtta acttcaagat    960
agatggaatt catgatgttg aaattggcac tctatatcct ggtgaatcgg taagaagttt   1020
ggaggaatgc tatgagaaat tgttgtcat ggcggctgac aagattcata agaagaaac   1080 tggagttacc gcaggtgggg gcggcacaac ggctatggta gagccggtgc caatcacagc   1140
ttcctgttga aaaggttcac ctgaggtgga tattcttttg agtcataaga catgttgatt   1200
gttgatgttg ttttcaagaa tgtttcatca tttcatgtgt tttattaatc ctaagtacaa   1260
ataattgctg tctacgtacg ttcttagttg caaaaattct tgttattctc tatcaaaaaa   1320
aaaaaaaaaa aaaaaaaaaa aaagtactct gcgttgttac cactgcttaa tcactagtga   1380
attc                                                               1384

<210> SEQ ID NO 16
<211> LENGTH: 356
<212> TYPE: PRT

<213> ORGANISM: Trifolium repens

<400> SEQUENCE: 16

Met Ala Pro Ala Ala Thr Ser Ser Pro Thr Thr Pro Thr Thr Thr Lys
1               5                   10                  15
Gly Arg Val Leu Ile Val Gly Gly Thr Gly Phe Ile Gly Lys Phe Val
            20                  25                  30
Thr Glu Ala Ser Leu Ser Thr Thr His Pro Thr Tyr Leu Leu Val Arg
        35                  40                  45
Pro Gly Pro Leu Leu Ser Ser Lys Ala Ala Thr Ile Lys Ala Phe Gln
    50                  55                  60
Glu Lys Gly Ala Ile Val Ile Tyr Gly Arg Val Asn Asn Lys Glu Phe
65                  70                  75                  80
Met Glu Met Ile Leu Lys Lys Tyr Glu Ile Asn Val Val Ile Ser Ala
            85                  90                  95
Ile Gly Gly Ser Asp Gly Leu Leu Glu Gln Leu Thr Leu Val Glu Ala
            100                 105                 110
Met Lys Ser Ile Asn Thr Ile Lys Arg Phe Leu Pro Ser Glu Phe Gly
        115                 120                 125
His Asp Val Asp Arg Ala Asp Pro Val Glu Pro Gly Leu Thr Met Tyr
    130                 135                 140
Lys Gln Lys Arg Leu Val Arg Val Ile Glu Glu Ser Gly Ile Pro
145                 150                 155                 160
Tyr Thr Tyr Ile Cys Cys Asn Ser Ile Ala Ser Trp Pro Tyr Tyr Asp
            165                 170                 175
Asn Cys His Pro Ser Gln Leu Pro Pro Leu Asp Gln Leu His Ile
            180                 185                 190
Tyr Gly His Gly Asp Val Lys Ala Tyr Phe Val Asp Gly Tyr Asp Ile
        195                 200                 205
Gly Lys Phe Thr Met Lys Val Ile Asp Asp Glu Arg Thr Ile Asn Lys
    210                 215                 220
Asn Val His Phe Arg Pro Ser Asn Asn Cys Tyr Ser Met Asn Glu Leu
225                 230                 235                 240
Ala Ser Leu Trp Glu Asn Lys Ile Ala Arg Lys Ile Pro Arg Val Ile
            245                 250                 255
Val Ser Glu Asp Asp Leu Leu Ala Ile Ala Ala Glu Asn Cys Ile Pro
            260                 265                 270
Glu Ser Val Val Ala Pro Ile Thr His Asp Ile Phe Ile Asn Gly Cys
        275                 280                 285
Gln Val Asn Phe Lys Ile Asp Gly Ile His Asp Val Glu Ile Gly Thr
    290                 295                 300
Leu Tyr Pro Gly Glu Ser Val Arg Ser Leu Glu Glu Cys Tyr Glu Lys
305                 310                 315                 320
Phe Val Val Met Ala Ala Asp Lys Ile His Lys Glu Glu Thr Gly Val
            325                 330                 335
Thr Ala Gly Gly Gly Gly Thr Thr Ala Met Val Glu Pro Val Pro Ile
        340                 345                 350
Thr Ala Ser Cys
        355

<210> SEQ ID NO 17
<211> LENGTH: 18
<212> TYPE: DNA
<213> ORGANISM: Artificial
<220> FEATURE:

```
<223> OTHER INFORMATION: Primer sequence

<400> SEQUENCE: 17
aggaggctgc agtcaagg                                                   18

<210> SEQ ID NO 18
<211> LENGTH: 19
<212> TYPE: DNA
<213> ORGANISM: Artificial
<220> FEATURE:
<223> OTHER INFORMATION: Primer sequence

<400> SEQUENCE: 18
tgcctgaaat tgagaaacc                                                  19

<210> SEQ ID NO 19
<211> LENGTH: 18
<212> TYPE: DNA
<213> ORGANISM: Artificial
<220> FEATURE:
<223> OTHER INFORMATION: Primer sequence

<400> SEQUENCE: 19
aaagctagcc ttgaagcc                                                   18

<210> SEQ ID NO 20
<211> LENGTH: 19
<212> TYPE: DNA
<213> ORGANISM: Artificial
<220> FEATURE:
<223> OTHER INFORMATION: Primer sequence

<400> SEQUENCE: 20
tcggacataa ctcatgtgg                                                  19

<210> SEQ ID NO 21
<211> LENGTH: 18
<212> TYPE: DNA
<213> ORGANISM: Artificial
<220> FEATURE:
<223> OTHER INFORMATION: Primer sequence

<400> SEQUENCE: 21
ttgggttgga gaataagg                                                   18

<210> SEQ ID NO 22
<211> LENGTH: 18
<212> TYPE: DNA
<213> ORGANISM: Artificial
<220> FEATURE:
<223> OTHER INFORMATION: Primer sequence

<400> SEQUENCE: 22
tggacattta ttggttgc                                                   18

<210> SEQ ID NO 23
<211> LENGTH: 18
<212> TYPE: DNA
<213> ORGANISM: Artificial
<220> FEATURE:
<223> OTHER INFORMATION: Primer sequence

<400> SEQUENCE: 23
tatcatgtct ggaaatgc                                                   18
```

```
<210> SEQ ID NO 24
<211> LENGTH: 19
<212> TYPE: DNA
<213> ORGANISM: Artificial
<220> FEATURE:
<223> OTHER INFORMATION: Primer sequence

<400> SEQUENCE: 24
agattgcatc aaagaatgg                                                      19

<210> SEQ ID NO 25
<211> LENGTH: 17
<212> TYPE: DNA
<213> ORGANISM: Artificial
<220> FEATURE:
<223> OTHER INFORMATION: Primer sequence

<400> SEQUENCE: 25
ggtccaaaag ccaatcc                                                        17

<210> SEQ ID NO 26
<211> LENGTH: 18
<212> TYPE: DNA
<213> ORGANISM: Artificial
<220> FEATURE:
<223> OTHER INFORMATION: Primer sequence

<400> SEQUENCE: 26
taagacgaga catagtgg                                                       18

<210> SEQ ID NO 27
<211> LENGTH: 18
<212> TYPE: DNA
<213> ORGANISM: Artificial
<220> FEATURE:
<223> OTHER INFORMATION: Primer sequence

<400> SEQUENCE: 27
tattcactaa gcacatgc                                                       18

<210> SEQ ID NO 28
<211> LENGTH: 19
<212> TYPE: DNA
<213> ORGANISM: Artificial
<220> FEATURE:
<223> OTHER INFORMATION: Primer sequence

<400> SEQUENCE: 28
tcatttctgc aataggagg                                                      19

<210> SEQ ID NO 29
<211> LENGTH: 18
<212> TYPE: DNA
<213> ORGANISM: Artificial
<220> FEATURE:
<223> OTHER INFORMATION: Primer sequence

<400> SEQUENCE: 29
atccacctca ggtgaacc                                                       18

<210> SEQ ID NO 30
<211> LENGTH: 18
<212> TYPE: DNA
<213> ORGANISM: Artificial
<220> FEATURE:
<223> OTHER INFORMATION: Primer sequence
```

<400> SEQUENCE: 30
aataggaggc tctgatgg                                                         18

<210> SEQ ID NO 31
<211> LENGTH: 18
<212> TYPE: DNA
<213> ORGANISM: Artificial
<220> FEATURE:
<223> OTHER INFORMATION: Primer sequence

<400> SEQUENCE: 31
atccacctca ggtgaacc                                                         18

<210> SEQ ID NO 32
<211> LENGTH: 17
<212> TYPE: DNA
<213> ORGANISM: Artificial
<220> FEATURE:
<223> OTHER INFORMATION: Primer sequence

<400> SEQUENCE: 32
aggctctgat ggcttgc                                                          17

<210> SEQ ID NO 33
<211> LENGTH: 18
<212> TYPE: DNA
<213> ORGANISM: Artificial
<220> FEATURE:
<223> OTHER INFORMATION: Primer sequence

<400> SEQUENCE: 33
atccacctca ggtgaacc                                                         18

<210> SEQ ID NO 34
<211> LENGTH: 30
<212> TYPE: DNA
<213> ORGANISM: Artificial
<220> FEATURE:
<223> OTHER INFORMATION: Primer sequence

<400> SEQUENCE: 34
gaattctaga agatatggtg agtgtagctg                                            30

<210> SEQ ID NO 35
<211> LENGTH: 30
<212> TYPE: DNA
<213> ORGANISM: Artificial
<220> FEATURE:
<223> OTHER INFORMATION: Primer sequence

<400> SEQUENCE: 35
gaattctaga atcacacatc ttatatagcc                                            30

<210> SEQ ID NO 36
<211> LENGTH: 55
<212> TYPE: DNA
<213> ORGANISM: Artificial
<220> FEATURE:
<223> OTHER INFORMATION: Primer sequence

<400> SEQUENCE: 36
ggggacaagt ttgtacaaaa aagcaggctt ctagaagata tggtgagtgt agctg               55

<210> SEQ ID NO 37
<211> LENGTH: 55

```
<212> TYPE: DNA
<213> ORGANISM: Artificial
<220> FEATURE:
<223> OTHER INFORMATION: Primer sequence

<400> SEQUENCE: 37
ggggaccact tgtacaaga aagctgggtt ctagaatcac acatcttata tagcc      55

<210> SEQ ID NO 38
<211> LENGTH: 33
<212> TYPE: DNA
<213> ORGANISM: Artificial
<220> FEATURE:
<223> OTHER INFORMATION: Primer sequence

<400> SEQUENCE: 38
gaattctaga agaagaaata tgggagacga agg                             33

<210> SEQ ID NO 39
<211> LENGTH: 33
<212> TYPE: DNA
<213> ORGANISM: Artificial
<220> FEATURE:
<223> OTHER INFORMATION: Primer sequence

<400> SEQUENCE: 39
gaattctaga aagacttcat gcacacaagt tcc                             33

<210> SEQ ID NO 40
<211> LENGTH: 34
<212> TYPE: DNA
<213> ORGANISM: Artificial
<220> FEATURE:
<223> OTHER INFORMATION: Primer sequence

<400> SEQUENCE: 40
gaattctaga tgattcattg tttgtttcca taac                            34

<210> SEQ ID NO 41
<211> LENGTH: 31
<212> TYPE: DNA
<213> ORGANISM: Artificial
<220> FEATURE:
<223> OTHER INFORMATION: Primer sequence

<400> SEQUENCE: 41
gaattctaga acatattcat cttcctatca c                               31

<210> SEQ ID NO 42
<211> LENGTH: 31
<212> TYPE: DNA
<213> ORGANISM: Artificial
<220> FEATURE:
<223> OTHER INFORMATION: Primer sequence

<400> SEQUENCE: 42
gaattctaga tccaaattct cgtacctcac c                               31

<210> SEQ ID NO 43
<211> LENGTH: 31
<212> TYPE: DNA
<213> ORGANISM: Artificial
<220> FEATURE:
<223> OTHER INFORMATION: Primer sequence

<400> SEQUENCE: 43
```

```
gaattctaga tagttcacat ctctcggcag g                                    31
```

<210> SEQ ID NO 44
<211> LENGTH: 37
<212> TYPE: DNA
<213> ORGANISM: Artificial
<220> FEATURE:
<223> OTHER INFORMATION: Primer sequence

<400> SEQUENCE: 44

```
ggatcctcta gagcactagt gtgtataagt ttcttgg                              37
```

<210> SEQ ID NO 45
<211> LENGTH: 35
<212> TYPE: DNA
<213> ORGANISM: Artificial
<220> FEATURE:
<223> OTHER INFORMATION: Primer sequence

<400> SEQUENCE: 45

```
ggatcctcta gacccccttta gtcttaaaat actcg                               35
```

<210> SEQ ID NO 46
<211> LENGTH: 52
<212> TYPE: DNA
<213> ORGANISM: Artificial
<220> FEATURE:
<223> OTHER INFORMATION: Primer sequence

<400> SEQUENCE: 46

```
ggggacaagt ttgtacaaaa aagcaggctc tagaaagcaa agcaatggca cc             52
```

<210> SEQ ID NO 47
<211> LENGTH: 51
<212> TYPE: DNA
<213> ORGANISM: Artificial
<220> FEATURE:
<223> OTHER INFORMATION: Primer sequence

<400> SEQUENCE: 47

```
ggggaccact ttgtacaaga aagctgggtc tagatccacc tcaggtgaac c              51
```

<210> SEQ ID NO 48
<211> LENGTH: 53
<212> TYPE: DNA
<213> ORGANISM: Artificial
<220> FEATURE:
<223> OTHER INFORMATION: Primer sequence

<400> SEQUENCE: 48

```
ggggacaagt ttgtacaaaa aagcaggctc tagaaagcaa tggcaccagc agc            53
```

<210> SEQ ID NO 49
<211> LENGTH: 51
<212> TYPE: DNA
<213> ORGANISM: Artificial
<220> FEATURE:
<223> OTHER INFORMATION: Primer sequence

<400> SEQUENCE: 49

```
ggggaccact ttgtacaaga aagctgggtc tagatccacc tcaggtgaac c              51
```

<210> SEQ ID NO 50
<211> LENGTH: 52
<212> TYPE: DNA
<213> ORGANISM: Artificial

```
<220> FEATURE:
<223> OTHER INFORMATION: Primer sequence

<400> SEQUENCE: 50
ggggacaagt ttgtacaaaa aagcaggctc tagataaagc aatggcacca gc        52

<210> SEQ ID NO 51
<211> LENGTH: 51
<212> TYPE: DNA
<213> ORGANISM: Artificial
<220> FEATURE:
<223> OTHER INFORMATION: Primer sequence

<400> SEQUENCE: 51
ggggaccact ttgtacaaga aagctgggtc tagatccacc tcaggtgaac c          51

<210> SEQ ID NO 52
<211> LENGTH: 36
<212> TYPE: DNA
<213> ORGANISM: Artificial
<220> FEATURE:
<223> OTHER INFORMATION: Primer sequence

<400> SEQUENCE: 52
ccaccatgtt tgaaatttat tatgtgtttt tttccg                           36

<210> SEQ ID NO 53
<211> LENGTH: 35
<212> TYPE: DNA
<213> ORGANISM: Artificial
<220> FEATURE:
<223> OTHER INFORMATION: Primer sequence

<400> SEQUENCE: 53
taatcccggg taagggcagc ccatacaaat gaagc                            35

<210> SEQ ID NO 54
<211> LENGTH: 36
<212> TYPE: DNA
<213> ORGANISM: Artificial
<220> FEATURE:
<223> OTHER INFORMATION: Primer sequence

<400> SEQUENCE: 54
ataataaccg gttgatcatg agcggagaat taaggg                           36

<210> SEQ ID NO 55
<211> LENGTH: 36
<212> TYPE: DNA
<213> ORGANISM: Artificial
<220> FEATURE:
<223> OTHER INFORMATION: Primer sequence

<400> SEQUENCE: 55
ataatagcgg ccgctagtaa catagatgac accgcg                           36

<210> SEQ ID NO 56
<211> LENGTH: 32
<212> TYPE: DNA
<213> ORGANISM: Artificial
<220> FEATURE:
<223> OTHER INFORMATION: Primer sequence

<400> SEQUENCE: 56
aatagcggcc gcgatttagt actggatttt gg                               32
```

<210> SEQ ID NO 57
<211> LENGTH: 31
<212> TYPE: DNA
<213> ORGANISM: Artificial
<220> FEATURE:
<223> OTHER INFORMATION: Primer sequence

<400> SEQUENCE: 57 ataaccggt acccacgaag gagcatcgtg g            31

<210> SEQ ID NO 58
<211> LENGTH: 32
<212> TYPE: DNA
<213> ORGANISM: Artificial
<220> FEATURE:
<223> OTHER INFORMATION: Primer sequence

<400> SEQUENCE: 58
ataataaccg gtgcccgggg atctcctttg cc           32

<210> SEQ ID NO 59
<211> LENGTH: 36
<212> TYPE: DNA
<213> ORGANISM: Artificial
<220> FEATURE:
<223> OTHER INFORMATION: Primer sequence

<400> SEQUENCE: 59
ataatagcgg ccgcatgcat gttgtcaatc aattgg       36

<210> SEQ ID NO 60
<211> LENGTH: 34
<212> TYPE: DNA
<213> ORGANISM: Artificial
<220> FEATURE:
<223> OTHER INFORMATION: Primer sequence

<400> SEQUENCE: 60
taataccggt aaatttatta tgrgtttttt tccg         34

<210> SEQ ID NO 61
<211> LENGTH: 37
<212> TYPE: DNA
<213> ORGANISM: Artificial
<220> FEATURE:
<223> OTHER INFORMATION: Primer sequence

<400> SEQUENCE: 61
taatgcggcc gctaagggca gcccatacaa atgaagc      37

<210> SEQ ID NO 62
<211> LENGTH: 23
<212> TYPE: DNA
<213> ORGANISM: Artificial
<220> FEATURE:
<223> OTHER INFORMATION: Primer sequence

<400> SEQUENCE: 62
catttcattt ggagaggaca cgc                    23

<210> SEQ ID NO 63
<211> LENGTH: 21
<212> TYPE: DNA
<213> ORGANISM: Artificial
<220> FEATURE:
<223> OTHER INFORMATION: Primer sequence

<400> SEQUENCE: 63
aacacggttt ggtggatttg c                                              21

<210> SEQ ID NO 64
<211> LENGTH: 22
<212> TYPE: DNA
<213> ORGANISM: Artificial
<220> FEATURE:
<223> OTHER INFORMATION: Primer sequence

<400> SEQUENCE: 64
ttggagagga cacgctgaaa tc                                             22

<210> SEQ ID NO 65
<211> LENGTH: 21
<212> TYPE: DNA
<213> ORGANISM: Artificial
<220> FEATURE:
<223> OTHER INFORMATION: Primer sequence

<400> SEQUENCE: 65
acaagttggt gagggaatgc c                                              21

<210> SEQ ID NO 66
<211> LENGTH: 23
<212> TYPE: DNA
<213> ORGANISM: Artificial
<220> FEATURE:
<223> OTHER INFORMATION: Primer sequence

<400> SEQUENCE: 66
catttcattt ggagaggaca cgc                                            23

<210> SEQ ID NO 67
<211> LENGTH: 22
<212> TYPE: DNA
<213> ORGANISM: Artificial
<220> FEATURE:
<223> OTHER INFORMATION: Primer sequence

<400> SEQUENCE: 67
tcgttgcctt tccctgagta gg                                             22

<210> SEQ ID NO 68
<211> LENGTH: 21
<212> TYPE: DNA
<213> ORGANISM: Artificial
<220> FEATURE:
<223> OTHER INFORMATION: Primer sequence

<400> SEQUENCE: 68
tcatttggag aggacacgct g                                              21

<210> SEQ ID NO 69
<211> LENGTH: 24
<212> TYPE: DNA
<213> ORGANISM: Artificial
<220> FEATURE:
<223> OTHER INFORMATION: Primer sequence

<400> SEQUENCE: 69
cggtcaccat tttttgttg gagg                                            24

<210> SEQ ID NO 70

<211> LENGTH: 22
<212> TYPE: DNA
<213> ORGANISM: Artificial
<220> FEATURE:
<223> OTHER INFORMATION: Primer sequence

<400> SEQUENCE: 70
ttggagagga cacgctgaaa tc                                          22

<210> SEQ ID NO 71
<211> LENGTH: 19
<212> TYPE: DNA
<213> ORGANISM: Artificial
<220> FEATURE:
<223> OTHER INFORMATION: Primer sequence

<400> SEQUENCE: 71
caacaaaacc agtgccacc                                              19

<210> SEQ ID NO 72
<211> LENGTH: 22
<212> TYPE: DNA
<213> ORGANISM: Artificial
<220> FEATURE:
<223> OTHER INFORMATION: Primer sequence

<400> SEQUENCE: 72
atgacgcaca atcccactat cc                                          22

<210> SEQ ID NO 73
<211> LENGTH: 24
<212> TYPE: DNA
<213> ORGANISM: Artificial
<220> FEATURE:
<223> OTHER INFORMATION: Primer sequence

<400> SEQUENCE: 73
agccttagaa gagagaagag gtcc                                        24

<210> SEQ ID NO 74
<211> LENGTH: 22
<212> TYPE: DNA
<213> ORGANISM: Artificial
<220> FEATURE:
<223> OTHER INFORMATION: Primer sequence

<400> SEQUENCE: 74
atgacgcaca atcccactat cc                                          22

<210> SEQ ID NO 75
<211> LENGTH: 24
<212> TYPE: DNA
<213> ORGANISM: Artificial
<220> FEATURE:
<223> OTHER INFORMATION: Primer sequence

<400> SEQUENCE: 75
agccttagaa gagagaagag gtcc                                        24

<210> SEQ ID NO 76
<211> LENGTH: 22
<212> TYPE: DNA
<213> ORGANISM: Artificial
<220> FEATURE:
<223> OTHER INFORMATION: Primer sequence

<400> SEQUENCE: 76

```
atgacgcaca atcccactat cc                                              22

<210> SEQ ID NO 77
<211> LENGTH: 24
<212> TYPE: DNA
<213> ORGANISM: Artificial
<220> FEATURE:
<223> OTHER INFORMATION: Primer sequence

<400> SEQUENCE: 77
agccttagaa gagagaagag gtcc                                            24
```

CHALCONE SYNTHASE DIHYRDOFLAVONOL 4-REDUCTASE AND LEUCOANTHOCYANIDINE REDUCTASE FROM CLOVER, MEDIC RYEGRASS OR FESCUE

The present invention relates to nucleic acid fragments encoding amino acid sequences for flavonoid biosynthetic enzyme polypeptides in plants, and the use thereof for the modification of, for example, flavonoid biosynthesis in plants, and more specifically the modification of the content of condensed tannins. In particularly preferred embodiments, the invention relates to the combinatorial expression of chalcone synthase (CHS) and/or dihydroflavonol 4-reductase (BAN) and/or leucoanthocyanidine reductase (LAR) in plants to modify, for example, flavonoid biosynthesis or more specifically the content of condensed tannins.

Flavonoids constitute a relatively diverse family of aromatic molecules that are derived from phenylalanine and malonyl-coenzyme A (CoA, via the fatty acid pathway). These compounds include six major subgroups that are found in most higher plants: the chalcones, flavones, flavonols, flavandiols, anthocyanins and condensed tannins (or proanthocyanidins). A seventh group, the aurones, is widespread, but not ubiquitous.

Some plant species also synthesize specialised forms of flavonoids, such as the isoflavonoids that are found in legumes and a small number of non-legume plants. Similarly, sorghum, maize and gloxinia are among the few species known to synthesize 3-deoxyanthocyanins (or phlobaphenes in the polymerised form). The stilbenes, which are closely related to flavonoids, are synthesised by another group of unrelated species that includes grape, peanut and pine.

Besides providing pigmentation to flowers, fruits, seeds, and leaves, flavonoids also have key roles in signalling between plants and microbes, in male fertility of some species, in defence as antimicrobial agents and feeding deterrents, and in UV protection.

Flavonoids also have significant activities when ingested by animals, and there is great interest in their potential health benefits, particularly for compounds such as isoflavonoids, which have been linked to anticancer benefits, and stilbenes that are believed to contribute to reduced heart disease. Condensed tannins which are plant polyphenols with protein-precipitating and antioxidant properties are involved in protein binding, metal chelation, anti-oxidation, and UV-light absorption. As a result condensed tannins inhibit viruses, microorganisms, insects, fungal pathogens, and monogastric digestion. Moderate amounts of tannins improve forage quality by disrupting protein foam and conferring protection from rumen pasture bloat. Bloat is a digestive disorder that occurs on some highly nutritious forage legumes such as alfalfa (*Medicago sativa*) and white clover (*Trifolium repens*). Moderate amounts of tannin can also reduce digestion rates in the rumen and can reduce parasitic load sufficiently to increase the titre of amino acids and small peptides in the small intestine without compromising total digestion.

The major branch pathways of flavonoid biosynthesis start with general phenylpropanoid metabolism and lead to the nine major subgroups: the colourless chalcones, aurones, isoflavonoids, flavones, flavonols, flavandiols, anthocyanins, condensed tannins, and phlobaphene pigments. The enzyme phenylalanine ammonia-lyase (PAL) of the general phenylpropanoid pathway will lead to the production of cinnamic acid. Cinnamate-4-hydroxylase (C4H) will produce p-coumaric acid which will be converted through the action of 4-coumaroyl:CoA-ligase (4CL) to the production of 4-coumaroyl-CoA and malonyl-CoA. The first committed step channeling carbon into the flavonoid biosynthesis pathway is catalysed by chalcone synthase (CHS), which uses malonyl CoA and 4-coumaryl CoA as substrates.

The *Arabidopsis* BANYULS gene encodes a dihydroflavonol 4-reductase-like protein (BAN) that may be an anthocyanine reductase (ACR). The reaction catalysed by BAN is considered to be one possible branching point from the general flavonoid pathway to the condensed tannin biosynthesis.

An alternative pathway to condensed tannins is via leucoanthocyanidine reductase (LAR). LAR utilises the same substrate as the ACR (BAN) but produces a 2,3-trans isomer as compared to the 2,3-cis isomer produced by ACR.

While nucleic acid sequences encoding the key enzymes in the condensed tannins biosynthetic pathway CHS, BAN and LAR have been isolated for certain species of plants, there remains a need for materials useful in modifying flavonoid biosynthesis and more specifically in modifying condensed tannin biosynthesis and therewith in modifying forage quality, for example by disrupting protein foam and conferring protection from rumen pasture bloat, particularly in forage legumes and grasses, including alfalfa, medics, clovers, ryegrasses and fescues, and for methods for their use.

It is an object of the present invention to overcome, or at least alleviate, one or more of the difficulties or deficiencies associated with the prior art.

In one aspect, the present invention provides substantially purified or isolated nucleic acids or nucleic acid fragments encoding key polypeptide enzymes in the condensed tannins biosynthetic pathway CHS, BAN and LAR, or functionally active fragments or variants of these enzymes, from a clover (*Trifolium*), medic (*Medicago*), ryegrass (*Lolium*) or fescue (*Festuca*) species.

The present invention also provides substantially purified or isolated nucleic acids or nucleic acid fragments encoding amino acid sequences for a class of polypeptides which are related to CHS, BAN and LAR or functionally active fragments or variants of CHS, BAN or LAR. Such polypeptides are referred to herein as CHS-like, BAN-like and LAR-like, respectively, and includes polypeptides having similar functional activity.

The individual or simultaneous enhancement or otherwise manipulation of CHS, BAN and LAR or like gene activities in plants may enhance or otherwise alter flavonoid biosynthesis; may enhance or otherwise alter the plant capacity for protein binding, metal chelation, anti-oxidation, and UV-light absorption; may enhance or reduce or otherwise alter plant pigment production; and may enhance or otherwise alter the amount of condensed tannins contained within forage legumes and grasses, including alfalfa, medics, clovers, ryegrasses and fescues and therewith the capacity to reduce bloating by disrupting protein foam.

Methods for the manipulation of CHS, BAN and LAR or like gene activities in plants, including legumes such as clovers (*Trifolium* species), lucerne (*Medicago sativa*) and grass species such as ryegrasses (*Lolium* species) and fescues (*Festuca* species) may facilitate the production of, for example, forage legumes and forage grasses and other crops with enhanced tolerance to biotic stresses such as viruses, microorganisms, insects and fungal pathogens; altered pigmentation in flowers; forage legumes with enhanced herbage quality and bloat-safety.

The clover (*Trifolium*), medic (*Medicago*), ryegrass (*Lolium*) or fescue (*Festuca*) species may be of any suitable type, including white clover (*Trifolium repens*), red clover (*Trifolium pratense*), subterranean clover (*Trifolium subterraneum*), alfalfa (*Medicago sativa*), Italian or annual ryegrass (*Lolium multiflorum*), perennial ryegrass (*Lolium perenne*), tall fescue (*Festuca arundinacea*), meadow fescue (*Festuca pratensis*) and red fescue (*Festuca rubra*). Preferably the species is a clover or a ryegrass, more preferably white clover (*T. repens*) or perennial ryegrass (*L. perenne*). White clover (*Trifolium repens* L.) and perennial ryegrass (*Lolium perenne* L.) are key pasture legumes and grasses, respectively, in temperate climates throughout the world. Perennial ryegrass is also an important turf grass.

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof. The RNA is readily obtainable, for example, by transcription of a DNA sequence according to the present invention, to produce an RNA corresponding to the DNA sequence. The RNA may be synthesised, in vivo or in vitro or by chemical synthesis to produce a sequence corresponding to a DNA sequence by methods well known in the art. In this specification, where the degree of sequence similarity between an RNA and DNA is such that the strand of the DNA could encode the RNA, then the RNA is said to "correspond" to that DNA.

In a preferred embodiment of this aspect of the invention, the substantially purified or isolated nucleic acid or nucleic acid fragment encoding a CHS or CHS-like protein includes the nucleotide sequences shown in FIGS. 2, 6, 10 and 14 hereto (Sequence ID Nos. 1, 3, 5 and 7, respectively); (b) complements of the sequences recited in (a); (c) sequences antisense to the sequences recited in (a) and (b); and (d) functionally active fragments and variants of the sequences recited in (a), (b) and (c); and (e) RNA sequences corresponding to the sequences recited in (a), (b), (c), and (d).

In a further preferred embodiment of this aspect of the invention, the substantially purified or isolated nucleic acid or nucleic acid fragment encoding a BAN or BAN-like protein includes the nucleotide sequence shown in FIG. 18 hereto (Sequence ID No. 9); (b) complements of the sequence recited in (a); (c) sequences antisense to the sequences recited in (a) and (b); and (d) functionally active fragments and variants of the sequences recited in (a), (b) and (c); and (e) RNA sequences corresponding to the sequences recited in (a), (b), (c), and (d).

In a still further preferred embodiment of this aspect of the invention, the substantially purified or isolated nucleic acid or nucleic acid fragment encoding a LAR or LAR-like protein includes the nucleotide sequence shown in FIGS. 22, 26 and 30 hereto (Sequence ID Nos. 11, 13 and 15 respectively); (b) complements of the sequences recited in (a); (c) sequences antisense to the sequences recited in (a) and (b); and (d) functionally active fragments and variants of the sequences recited in (a), (b) and (c); and (e) RNA sequences corresponding to the sequences recited in (a), (b), (c), and (d).

The term "isolated" means that the material is removed from its original environment (e.g. the natural environment if it is naturally occurring). For example, a naturally occurring nucleic acid or polypeptide present in a living plant is not isolated, but the same nucleic acid or polypeptide separated from some or all of the coexisting materials in the natural system, is isolated. Such nucleic acids could be part of a vector and/or such nucleic acids could be part of a composition, and still be isolated in that such a vector or composition is not part of its natural environment. An isolated polypeptide could be part of a composition and still be isolated in that such a composition is not part of its natural environment.

The term "purified" means that the nucleic acid or polypeptide is substantially free of other nucleic acids or polypeptides.

By "functionally active" in respect of a nucleic acid it is meant that the fragment or variant (such as an analogue, derivative or mutant) is capable of modifying flavonoid biosynthesis in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

By "functionally active" in respect of a polypeptide is meant that the fragment or variant has one or more of the biological properties or functions of the polypeptides CHS, CHS-like, BAN, BAN-like, LAR and LAR-like, respectively. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "vector" as used herein encompasses both cloning and expression vectors. Vectors are often recombinant molecules containing nucleic acid molecules from several sources.

By "operatively linked" is meant that said regulatory element(s) is capable of causing expression of said nucleic acid(s) or nucleic acid fragment(s) in a plant cell and said terminator(s) is capable of terminating expression of said nucleic acid(s) or nucleic acid fragment(s) in a plant cell.

Preferably, said regulatory element(s) is upstream of said nucleic acid(s) or nucleic acid fragment(s) and said terminator(s) is downstream of said nucleic acid(s) or nucleic acid fragment(s). In a particularly preferred embodiment, each nucleic acid or nucleic acid fragment has one or more upstream promoters and one or more downstream terminators, although expression of more than one nucleic acid or nucleic acid fragment from an upstream regulatory element(s) or termination of more than one nucleic acid or nucleic acid fragment from a downstream terminator(s) is not precluded.

By "an effective amount" it is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Sambrook et al., Molecular Cloning: A Laboratory Manual, Cold Spring Harbor Laboratory, Cold Spring Harbor, the entire disclosure of which is incorporated herein by reference.

It will also be understood that the term "comprises" (or its grammatical variants) as used in this specification is equivalent to the term "includes" and should not be taken as excluding the presence of other elements or features.

Genes encoding other CHS or CHS-like, BAN or BAN-like and LAR or LAR-like proteins, either as cDNAs or genomic DNAs, may be isolated directly by using all or a portion of the nucleic acids or nucleic acid fragments of the present invention as hybridisation probes to screen libraries from the desired plant employing the methodology well known to those skilled in the art. Specific oligonucleotide probes based upon the nucleic acid sequences of the present invention may be designed and synthesized by methods known in the art. Moreover, the entire sequences may be used directly to synthesize DNA probes by methods known to the skilled artisan such as random primer DNA labelling, nick translation, or end-labelling techniques, or RNA probes using available in vitro transcription systems. In addition, specific primers may be designed and used to amplify a part or all of the sequences of the present invention. The resulting amplification products may be labelled directly during amplification reactions or labelled after amplification reactions, and used as probes to isolate full-length cDNA or genomic fragments under conditions of appropriate stringency.

In addition, short segments of the nucleic acids or nucleic acid fragments of the present invention may be used in protocols to amplify longer nucleic acids or nucleic acid fragments encoding homologous genes from DNA or RNA. For example, polymerase chain reaction may be performed on a library of cloned nucleic acid fragments wherein the sequence of one primer is derived from the nucleic acid sequences of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol [Frohman et al. (1988), *Proc. Natl. Acad. Sci. USA* 85:8998, the entire disclosure of which is incorporated herein by reference] to generate cDNAs by using PCR to amplify copies of the region between a single point in the transcript and the 3' or 5' end. Using commercially available 3' RACE and 5' RACE systems (BRL), specific 3' or 5' cDNA fragments may be isolated [Ohara et al. (1989), *Proc. Natl. Acad. Sci. USA* 86:5673; Loh et al. (1989), *Science* 243:217, the entire disclosures of which are incorporated herein by reference]. Products generated by the 3' and 5' RACE procedures may be combined to generate full-length cDNAs.

In a second aspect of the present invention there is provided a substantially purified or isolated polypeptide from a clover, (*Trifolium*), medic (*Medicago*), ryegrass (*Lolium*) or fescue (*Festuca*) species, selected from the group consisting of CHS and CHS-like, BAN and BAN-like, and LAR and LAR-like proteins; and functionally active fragments and variants thereof.

The clover (*Trifolium*), medic (*Medicago*), ryegrass (*Lolium*) or fescue (*Festuca*) species may be of any suitable type, including white clover (*Trifolium repens*), red clover (*Trifolium pratense*), subterranean clover (*Trifolium subterraneum*), alfalfa (*Medicago sativa*), Italian or annual ryegrass (*Lolium multiflorum*), perennial ryegrass (*Lolium perenne*), tall fescue (*Festuca arundinacea*), meadow fescue (*Festuca pratensis*) and red fescue (*Festuca rubra*). Preferably the species is a clover or a ryegrass, more preferably white clover (*T. repens*) or perennial ryegrass (*L. perenne*).

In a preferred embodiment of this aspect of the invention, the substantially purified or isolated CHS or CHS-like polypeptide includes an amino acid sequence selected from the group consisting of sequences shown in FIGS. 3, 7, 11 and 15 hereto (Sequence ID Nos. 2, 4, 6 and 8, respectively) and functionally active fragments and variants thereof.

In a further preferred embodiment of this aspect of the invention, the substantially purified or isolated BAN or BAN-like polypeptide includes an amino acid sequence shown in FIG. 19 hereto (Sequence ID No. 10), and functionally active fragments and variants thereof.

In a still further preferred embodiment of this aspect of the invention, the substantially purified or isolated LAR or LAR-like polypeptide includes an amino acid sequence selected from the group consisting of sequences shown in FIGS. 23, 27 and 31 hereto (Sequence ID Nos. 12, 14 and 16, respectively), and functionally active fragments and variants thereof.

In a further embodiment of this aspect of the invention, there is provided a polypeptide produced (e.g. recombinantly) from a nucleic acid or nucleic acid fragment according to the present invention. Techniques for recombinantly producing polypeptides are well known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins including the amino acid sequences. These antibodies may be then used to screen cDNA expression libraries to isolate full-length cDNA clones of interest.

In a still further aspect of the present invention there is provided a construct including one or more nucleic acids or nucleic acid fragments according to the present invention.

In a particularly preferred embodiment the construct may include nucleic acids or nucleic acid fragments encoding both CHS or CHS-like and BAN or BAN-like polypeptides.

In another preferred embodiment the construct may include nucleic acids or nucleic acid fragments encoding both CHS or CHS-like and LAR or LAR-like polypeptides.

In yet another preferred embodiment the construct may include nucleic acids or nucleic acid fragments encoding both LAR or LAR-like and BAN or BAN-like polypeptides.

In an even more preferred embodiment the construct may include nucleic acids or nucleic acid fragments encoding all three of CHS or CHS-like, BAN or BAN-like and LAR or LAR-like polypeptides.

Constructs including nucleic acids or nucleic acid fragments encoding CHS or CHS-like and BAN or BAN-like, and optionally further including nucleic acids or nucleic acid fragments encoding LAR or LAR-like, are particularly preferred.

In a still further aspect of the present invention there is provided a vector including one or more nucleic acids or nucleic acid fragments according to the present invention.

In a preferred embodiment of this aspect of the invention, the construct may include one or several of the following: one or more regulatory elements such as promoters, one or more nucleic acids or nucleic acid fragments according to the present invention and one or more terminators; said on or more regulatory elements, one or more nucleic acids or nucleic acid fragments and one or more terminators being operatively linked.

In a particularly preferred embodiment the construct may contain nucleic acids or nucleic acid fragments encoding both CHS or CHS-like and BAN or BAN-like polypeptides, operatively linked to a regulatory element or regulatory elements, such that both CHS or CHS-like and BAN or BAN-like polypeptides are expressed.

In another preferred embodiment the construct may contain nucleic acids or nucleic acid fragments encoding both CHS or CHS-like and LAR or LAR-like polypeptides, operatively linked to a regulatory element or regulatory elements, such that both CHS or CHS-like and LAR or LAR-like polypeptides are expressed.

In yet another preferred embodiment the construct may contain nucleic acids or nucleic acid fragments encoding both LAR or LAR-like and BAN or BAN-like polypeptides, operatively linked to a regulatory element or regulatory elements, such that both LAR or LAR-like and BAN or BAN-like polypeptides are expressed.

In an even more preferred embodiment the construct may contain nucleic acids or nucleic acid fragments encoding all three of CHS or CHS-like, BAN or BAN-like and LAR or LAR-like polypeptides, operatively linked to a regulatory element or regulatory elements, such that all three of CHS or CHS-like, BAN or BAN-like and LAR or LAR-like polypeptides are expressed.

Constructs including nucleic acids or nucleic acid fragments encoding CHS or CHS-like and BAN or BAN-like, and optionally further including nucleic acids or nucleic acid fragments encoding LAR or LAR-like, are particularly preferred.

The construct or vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (e.g. monocotyledon or dicotyledon). Particularly suitable promoters include but are not limited to the constitutive Cauliflower Mosaic Virus 35S (CaMV 35S) promoter and derivatives thereof, the maize Ubiquitin promoter, the rice Actin promoter, and the tissue-specific *Arabidopsis* small subunit (ASSU) promoter.

A variety of terminators which may be employed in the vectors and constructs of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos), the octopine synthase (ocs) and the rbcS genes.

The construct or vector, in addition to the regulatory element(s), the nucleic acid(s) or nucleic acid fragment(s) of the present invention and the terminator(s), may include further elements necessary for expression of the nucleic acid(s) or nucleic acid fragment(s), in different combinations, for example vector backbone, origin of replication (ori), multiple cloning sites, recognition sites for recombination events, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene and the gentamycin acetyl transferase (aacC1) gene], and reporter genes [such as beta-glucuronidase (GUS) gene (gusA) and green fluorescent protein (gfp)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, visual examination including microscopic examination of fluorescence emitted by gfp, northern and Western blot hybridisation analyses.

Those skilled in the art will appreciate that the various components of the construct or vector are operatively linked, so as to result in expression of said nucleic acid(s) or nucleic acid fragment(s). Techniques for operatively linking the components of the vector of the present invention are well known to those skilled in the art. Such techniques include the use of linkers, such as synthetic linkers, for example including one or more restriction enzyme sites.

The constructs and vectors of the present invention may be incorporated into a variety of plants, including monocotyledons (such as grasses from the genera *Lolium, Festuca, Paspalum, Pennisetum, Panicum* and other forage and turfgrasses, corn, oat, sugarcane, wheat and barley), dicotyledons (such as *Arabidopsis*, tobacco, clovers, medics, eucalyptus, potato, sugarbeet, canola, soybean, chickpea) and gymnosperms. In a preferred embodiment, the vectors may be used to transform monocotyledons, preferably grass species such as ryegrasses (*Lolium* species) and fescues (*Festuca* species), more preferably perennial ryegrass, including forage- and turf-type cultivars. In an alternate preferred embodiment, the constructs and vectors may be used to transform dicotyledons, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*). Clovers, alfalfa and medics are key pasture legumes in temperate climates throughout the world.

Techniques for incorporating the constructs and vectors of the present invention into plant cells (for example by transduction, transfection or transformation) are known to those skilled in the art. Such techniques include *Agrobacterium*-mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

In a further aspect of the present invention there is provided a method of isogenic transformation of a dicotyledonous plant, said method including transforming only one of each pair of cotyledons. This enables the production of pairs of transgenic plant and corresponding untransformed negative control in an otherwise isogenic genetic background for detailed functional assessment of the impact of the transgene on plant phenotype. In a preferred embodiment of this aspect of the invention, the method may include isogenic transformation of a dicotyledonous plant with a construct or vector according to the present invention.

Cells incorporating the constructs and vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, one or more constructs, vectors, nucleic acids or nucleic acid fragments of the present invention.

The plant cell, plant, plant seed or other plant part may be from any suitable species, including monocotyledons, dicotyledons and gymnosperms. In a preferred embodiment the plant cell, plant, plant seed or other plant part may be from a monocotyledon, preferably a grass species, more preferably a ryegrass (*Lolium* species) or fescue (*Festuca* species), more preferably perennial ryegrass, including both forage- and turf-type cultivars. In an alternate preferred embodiment the plant cell, plant, plant seed or other plant part may be from a dicotyledon, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*).

The present invention also provides a plant, plant seed or other plant part, or a plant extract derived from a plant cell of the present invention.

The present invention also provides a plant, plant seed or other plant part, or a plant extract derived from a plant of the present invention.

In a further aspect of the present invention there is provided a method of modifying condensed tannin biosynthesis; of modifying flavonoid biosynthesis; of modifying protein binding, metal chelation, anti-oxidation, and UV-light absorption; of modifying plant pigment production; of modifying plant defence to biotic stresses such as viruses, microorganisms, insects, fungal pathogens; of modifying forage quality by disrupting protein foam and conferring protection from rumen pasture bloat, said method including introducing into said plant an effective amount of a nucleic acid or nucleic acid fragment, construct and/or vector according to the present invention.

In a particularly preferred embodiment the method may include introducing into said plant nucleic acids or nucleic acid fragments encoding both CHS or CHS-like and BAN or BAN-like polypeptides.

In another preferred embodiment the method may include introducing into said plant nucleic acids or nucleic acid fragments encoding both CHS or CHS-like and LAR or LAR-like polypeptides.

In yet another preferred embodiment the method may include introducing into said plant nucleic acids or nucleic acid fragments encoding both LAR or LAR-like and BAN or BAN-like polypeptides.

In an even more preferred embodiment the method may include introducing into said plant nucleic acids or nucleic acid fragments encoding all three of CHS or CHS-like, BAN or BAN-like and LAR or LAR-like polypeptides.

Methods including the combinatorial expression of nucleic acids or nucleic acid fragments encoding CHS or CHS-like and BAN or BAN-like, and optionally further including the use of nucleic acids or nucleic acid fragments encoding LAR or LAR-like, are particularly preferred.

In a further aspect of the present invention there is provided a method of inhibiting bloat in an animal, said method including providing the animal with a forage plant including a construct, vector, nucleic acid or nucleic acid fragment according to the present invention. The animal is preferably a ruminant, including sheep, goats and cattle. The forage plant including a construct vector, nucleic acid or nucleic acid fragment according to the present invention may form all or part of the feed of the animal. The forage plant preferably expresses CHS or CHS-like proteins, BAN or BAN-like proteins, and/or LAR or LAR-like proteins at higher levels than the equivalent wild-type plant. More preferably, the forage plant expresses both CHS or CHS-like proteins and BAN or BAN-like proteins; both CHS or CHS-like proteins and LAR or LAR-like proteins; or both BAN or BAN-like proteins and LAR or LAR-like proteins; at higher levels than the equivalent wild-type plant. More preferably, the forage plant expresses all three of CHS or CHS-like proteins, BAN or BAN-like proteins, and LAR or LAR-like proteins; at higher levels than the equivalent wild-type plant.

In a further aspect of the present invention there is provided a method for enhancing an animal's growth rate, said method including providing the animal with a forage plant including a construct, vector, nucleic acid or nucleic acid fragment according to the present invention. The animal is preferably a ruminant, including sheep, goats and cattle. The forage plant including a construct, vector, nucleic acid or nucleic acid fragment according to the present invention may form all or part of the feed of the animal. The forage plant preferably expresses CHS or CHS-like proteins, BAN or BAN-like proteins, and/or LAR or LAR-like proteins at higher levels than the equivalent wild-type plant. More preferably, the forage plant expresses both CHS or CHS-like proteins and BAN or BAN-like proteins; both CHS or CHS-like proteins and LAR or LAR-like proteins; or both BAN or BAN-like proteins and LAR or LAR-like proteins; at higher levels than the equivalent wild-type plant. More preferably, the forage plant expresses all three of CHS or CHS-like proteins, BAN or BAN-like proteins, and LAR or LAR-like proteins; at higher levels than the equivalent wild-type plant.

It is estimated that the method of enhancing an animal's growth rate according to this invention should result in an increase in, for example, lamb growth rate of at least approximately 5%, more preferably at least approximately 10%.

Using the methods and materials of the present invention, condensed tannin biosynthesis, flavonoid biosynthesis, protein binding, metal chelation, anti-oxidation, UV-light absorption, tolerance to biotic stresses such as viruses, microorganisms, insects and fungal pathogens; pigmentation in for example flowers and leaves; herbage quality and bloat-safety; isoflavonoid content leading to health benefits, may be increased or otherwise altered, for example by incorporating additional copies of one or more sense nucleic acids or nucleic acid fragments of the present invention. They may be decreased or otherwise altered, for example by incorporating one or more antisense nucleic acids or nucleic acid fragments of the present invention.

Documents cited in this specification are for reference purposes only and their inclusion is not acknowledgment that they form part of the common general knowledge in the relevant art.

The present invention will now be more fully described with reference to the accompanying Examples and drawings. It should be understood, however, that the description following is illustrative only and should not be taken in any way as a restriction on the generality of the invention described above.

In the Figures

FIG. 2 shows the nucleotide sequence of TrCHSa3 (Sequence ID No. 1).

FIG. 3 shows the deduced amino acid sequence of TrCHSa3 (Sequence ID No. 2).

Figure 4:
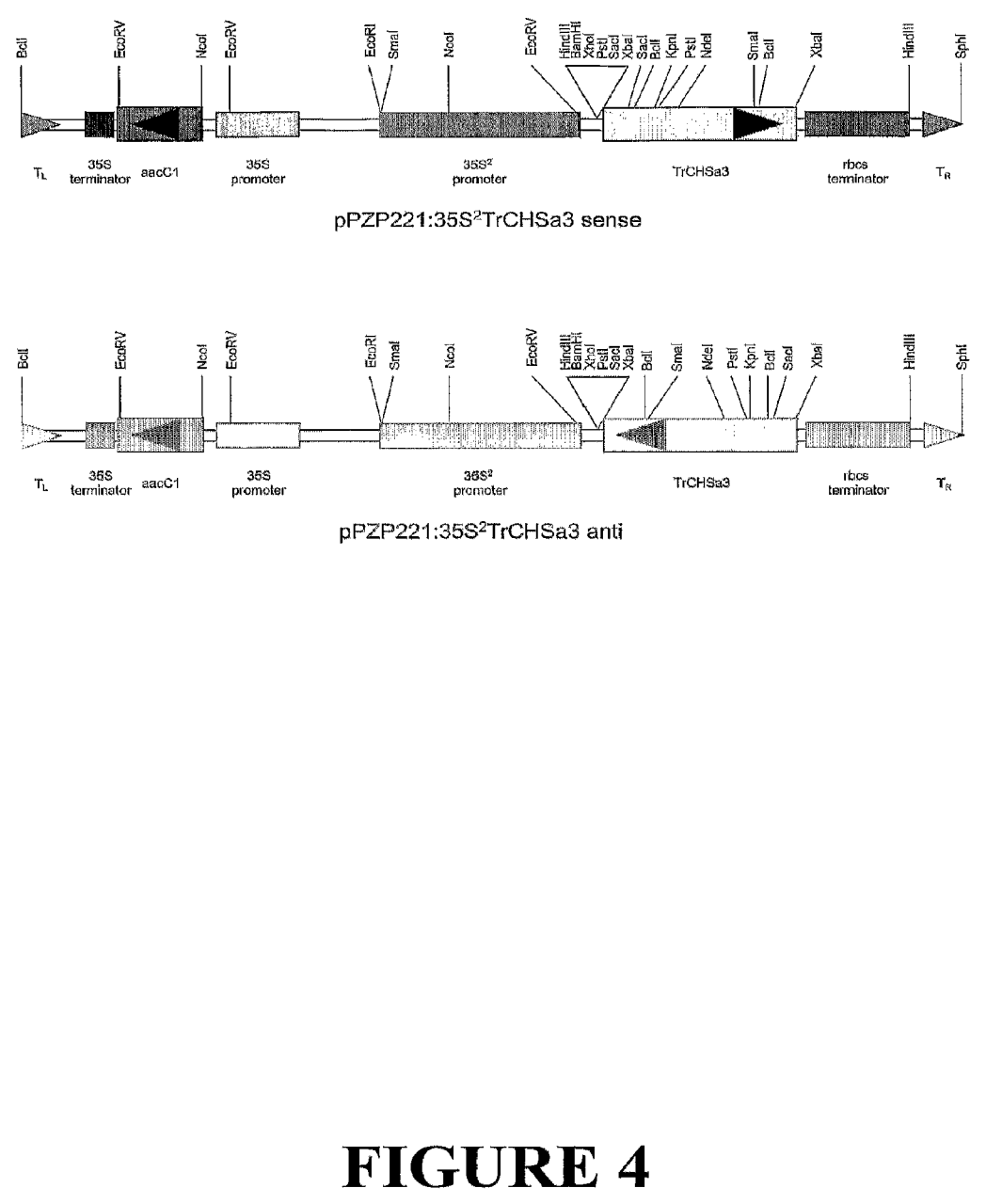

FIG. 4 shows plasmid maps of sense and antisense constructs of TrCHSa3 in the binary vector pPZP221:35 $S^2$.

FIG. 6 shows the nucleotide sequence of TrCHSc (Sequence ID No. 3).

FIG. 7 shows the deduced amino acid sequence of TrCHSc (Sequence ID No. 4).

FIG. 8 shows plasmid maps of sense and antisense constructs of TrCHSc in the binary vector pPZP221:35 $S^2$.

FIG. 10 shows the nucleotide sequence of TrCHSf (Sequence ID No. 5).

FIG. 11 shows the deduced amino acid sequence of TrCHSf (Sequence ID No. 6).

FIG. 12 shows plasmid maps of sense and antisense constructs of TrCHSf in the binary vector pPZP221:35 $S^2$.

FIG. 14 shows the nucleotide sequence of TrCHSh (Sequence ID No. 7).

FIG. 15 shows the deduced amino acid sequence of TrCHSh (Sequence ID No. 8).

FIG. 16 shows plasmid maps of sense and antisense constructs of TrCHSh in the binary vector pPZP221:35 $S^2$.

FIG. 18 shows the nucleotide sequence of TrBANa (Sequence ID No. 9).

FIG. 19 shows the deduced amino acid sequence of TrBANa (Sequence ID No. 10).

FIG. 20 shows plasmid maps of sense and antisense constructs TrBANa in the binary vector pPZP221:35 $S^2$.

FIG. 22 shows the nucleotide sequence of TrLARa (Sequence ID No. 11).

FIG. 23 shows the deduced amino acid sequence of TrLARa (Sequence ID No. 12).

FIG. 24 shows plasmid maps of sense and antisense constructs of TrLARa in the binary vector pPZP221:35 $S^2$.

FIG. 26 shows the nucleotide sequence of TrLARb (Sequence ID No. 13).

FIG. 27 shows the deduced amino acid sequence of TrLARb (Sequence ID No. 14).

FIG. 30 shows the nucleotide sequence of TrLARc (Sequence ID No. 15).

FIG. 31 shows the deduced amino acid sequence of TrLARc (Sequence ID No. 16).

FIG. 32 shows plasmid maps of sense and antisense constructs of TrLARc in the binary vector pPZP221:35 $S^2$.

Figure 36:
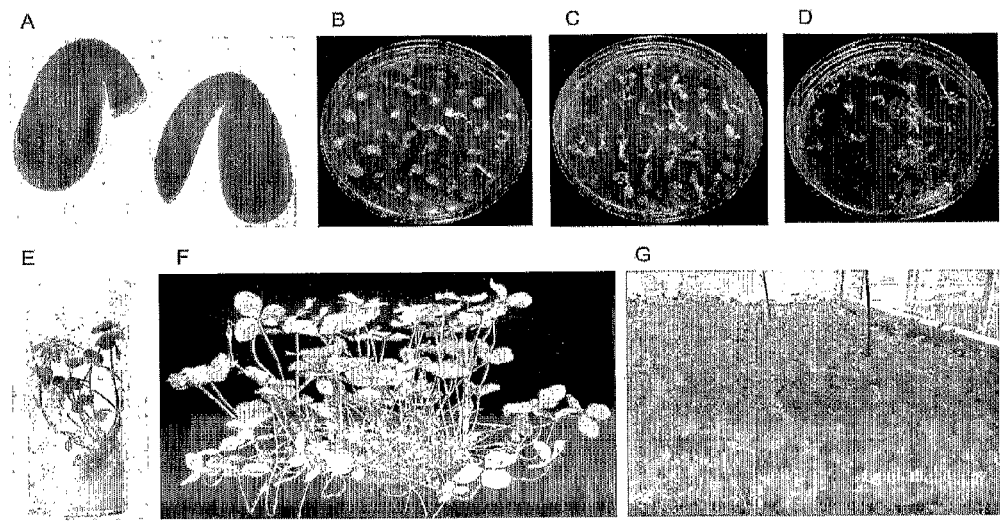

FIG. 36 shows A, white clover cotyledons; B, C, D, selection of plantlets transformed with a binary transformation vector constructed as described in Examples 4 and 5; E, putative transgenic white clover on root-inducing medium; F, G, white clover plants transgenic for genes involved in condensed tannin biosynthesis.

Figure 37:
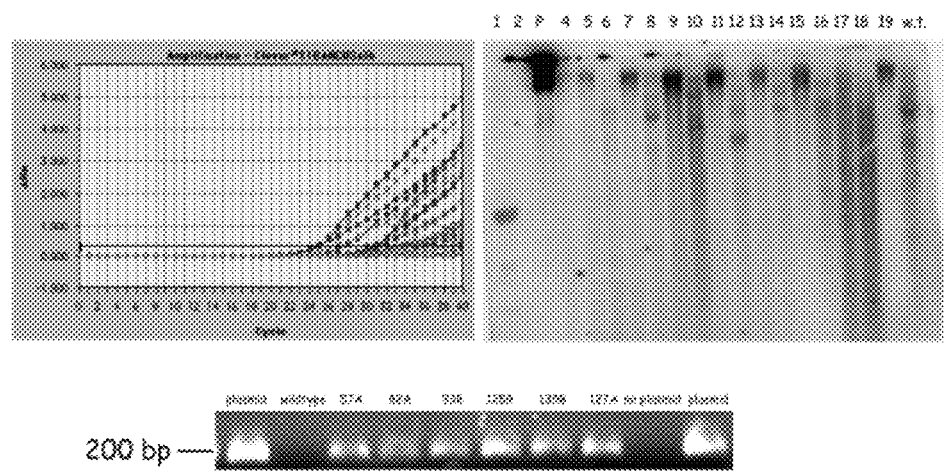

FIG. 37 shows the molecular analysis of white clover plants transgenic for the TrBAN gene with Q-PCR amplification plot, agarose gel of PCR product and Southern hybridisation blot.

Figure 38:
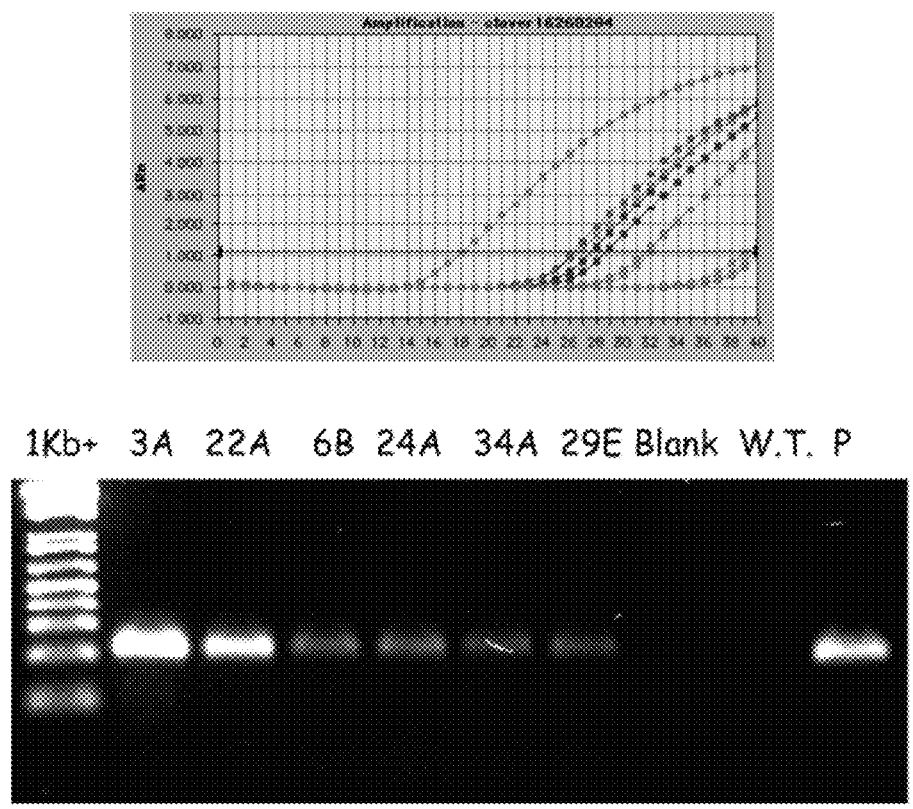

FIG. 38 shows the molecular analysis of white clover plants transgenic for the TrCHSf gene with Q-PCR amplification plot and agarose gel of PCR product.

Figure 39:
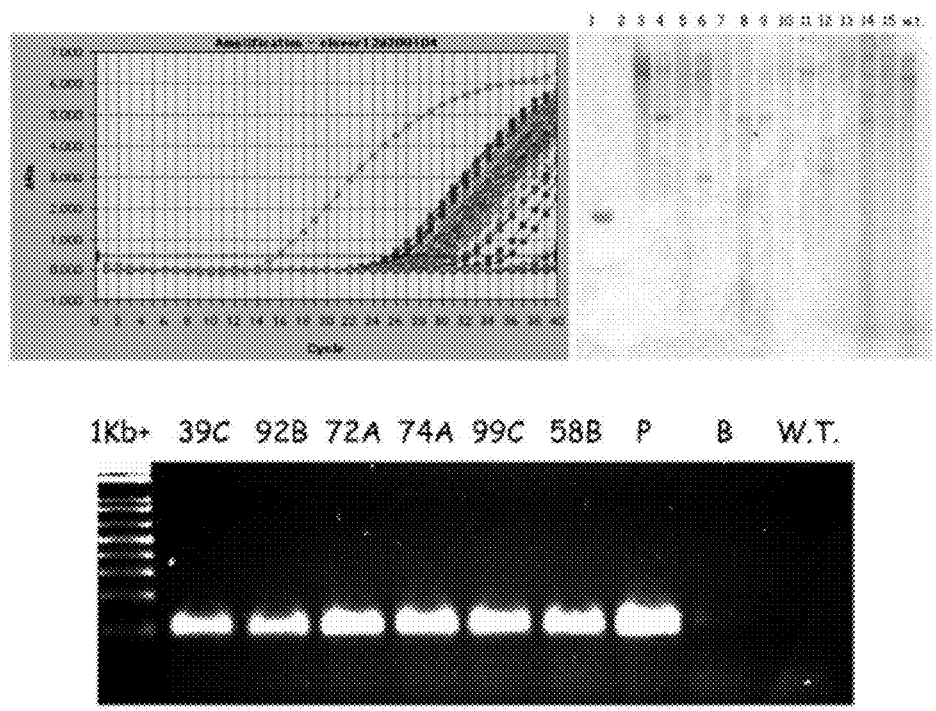

FIG. 39 shows the molecular analysis of white clover plants transgenic for the TrLARb gene with Q-PCR amplification plot, agarose gel of PCR product and Southern hybridisation blot.

EXAMPLE 1

Preparation of cDNA Libraries, Isolation and Sequencing of cDNAs Coding for CHS, CHS-like, BAN, BAN-like, LAR and LAR-Like Proteins from White Clover *Trifolium repens* cDNA libraries representing mRNAs from various organs and tissues of white clover (*Trifolium repens*) were prepared. The characteristics of the white clover libraries are described below (Table 1).

TABLE 1 cDNA libraries from white clover (*Trifolium repens*)

| Library | Organ/Tissue |
|---|---|
| 01wc | Whole seedling, light grown |
| 02wc | Nodulated root 3, 5, 10, 14, 21 & 28 day old seedling |
| 03wc | Nodules pinched off roots of 42 day old *rhizobium* inoculated plants |
| 04wc | Cut leaf and stem collected after 0, 1, 4, 6 & 14 h after cutting |
| 05wc | Inflorescences: <50% open, not fully open and fully open |
| 06wc | Dark grown etiolated |
| 07wc | Inflorescence-very early stages, stem elongation, <15 petals, 15-20 petals |
| 08wc | seed frozen at −80° C., imbibed in dark overnight at 10° C. |
| 09wc | Drought stressed plants |
| 10wc | AMV infected leaf |
| 11wc | WCMV infected leaf |
| 12wc | Phosphorus starved plants |
| 13wc | Vegetative stolon tip |
| 14wc | stolon root initials |
| 15wc | Senescing stolon |
| 16wc | Senescing leaf |

The cDNA libraries may be prepared by any of many methods available. For example, total RNA may be isolated using the Trizol method (Gibco-BRL, USA) or the RNeasy Plant Mini kit (Qiagen, Germany), following the manufacturers' instructions. cDNAs may be generated using the SMART PCR cDNA synthesis kit (Clontech, USA), cDNAs may be amplified by long distance polymerase chain reaction using the Advantage 2 PCR Enzyme system (Clontech, USA), cDNAs may be cleaned using the GeneClean spin column (Bio 101, USA), tailed and size fractionated, according to the protocol provided by Clontech. The cDNAs may be introduced into the pGEM-T Easy Vector system 1 (Promega, USA) according to the protocol provided by Promega. The cDNAs in the pGEM-T Easy plasmid vector are transfected into *Escherichia coli* Epicurean coli XL10-Gold ultra competent cells (Stratagene, USA) according to the protocol provided by Stratagene.

Alternatively, the cDNAs may be introduced into plasmid vectors for first preparing the cDNA libraries in Uni-ZAP XR vectors according to the manufacturer's protocol (Stratagene Cloning Systems, La Jolla, Calif., USA). The Uni-ZAP XR libraries are converted into plasmid libraries according to the protocol provided by Stratagene. Upon conversion, cDNA inserts will be contained in the plasmid vector pBlueScript. In addition, the cDNAs may be introduced directly into precut pBlueScript II SK(+) vectors (Stratagene) using T4 DNA ligase (New England Biolabs), followed by transfection into *E. coli* DH10B cells according to the manufacturer's protocol (GIBCO BRL Products).

Once the cDNA inserts are in plasmid vectors, plasmid DNAs are prepared from randomly picked bacterial colonies containing recombinant plasmids, or the insert cDNA sequences are amplified via polymerase chain reaction using primers specific for vector sequences flanking the inserted cDNA sequences. Plasmid DNA preparation may be performed robotically using the Qiagen QiaPrep Turbo kit (Qiagen, Germany) according to the protocol provided by Qiagen. Amplified insert DNAs are sequenced in dye-terminator sequencing reactions to generate partial cDNA sequences (expressed sequence tags or "ESTs"). The resulting ESTs are analysed using an Applied Biosystems ABI 3700 sequence analyser.

EXAMPLE 2

DNA Sequence Analyses

The cDNA clones encoding CHS, CHS-like, BAN, BAN-like, LAR and LAR-like proteins were identified by conducting BLAST (Basic Local Alignment Search Tool; Altschul et al. (1993), *J. Mol. Biol.* 215:403-410) searches. The cDNA sequences obtained were analysed for similarity to all publicly available DNA sequences contained in the eBioinformatics nucleotide database using the BLASTn algorithm provided by the National Center for Biotechnology Information (NCBI). The DNA sequences were translated in all reading frames and compared for similarity to all publicly available protein sequences contained in the SWISS-PROT protein sequence database using BLASTx algorithm (v 2.0.1) (Gish and States (1993), *Nature Genetics* 3:266-272) provided by the NCBI.

The cDNA sequences obtained and identified were then used to identify additional identical and/or overlapping cDNA sequences generated using the BLASTn algorithm. The identical and/or overlapping sequences were subjected to a multiple alignment using the CLUSTALw algorithm, and to generate a consensus contig sequence derived from this multiple sequence alignment. The consensus contig sequence was then used as a query for a search against the SWISS-PROT protein sequence database using the BLASTx algorithm to confirm the initial identification.

EXAMPLE 3

Identification and Full-Length Sequencing of cDNAs Encoding White Clover CHS, BAN and LAR Proteins To fully characterise for the purposes of the generation of probes for hybridisation experiments and the generation of transformation vectors, a set of cDNAs encoding white clover CHS, BAN and LAR proteins was identified and fully sequenced.

Full-length cDNAs were identified from our EST sequence database using relevant published sequences (NCBI databank) as queries for BLAST searches. Full-length cDNAs were identified by alignment of the query and hit sequences using Sequencher (Gene Codes Corp., Ann Arbor, Mich. 48108, USA). The original plasmid was then used to transform chemically competent XL-1 cells (prepared in-house, $CaCl_2$ protocol). After colony PCR (using HotStarTaq, Qiagen) a minimum of three PCR-positive colonies per transformation were picked for initial sequencing with M13F and M13R primers. The resulting sequences were aligned with the original EST sequence using Sequencher to confirm identity and one of the three clones was picked for full-length sequencing, usually the one with the best initial sequencing result.

Sequencing of TrBAN could be completed with M13F and M13R primers. Sequencing of TrCHSa3, TrCHSc, TrCHSf, TrCHSh, TrLARa, TrLARb and TrLARc was completed by primer walking, i.e. oligonucleotide primers were designed to the initial sequence and used for further sequencing. The sequences of the oligonucleotide primers are shown in Table 2.

Contigs were then assembled in Sequencher. The contigs include the sequences of the SMART primers used to generate the initial cDNA library as well as pGEM-T Easy vector sequence up to the EcoRI cut site both at the 5' and 3' end.

Plasmid maps and the full cDNA sequences of TrCHSa3, TrCHSc, TrCHSf, TrCHSh, TrBANa, TrLARa, TrLARb and TrLARc proteins were obtained (FIGS. 1, 2, 5, 6, 9, 10, 13, 14, 17, 18, 21, 22, 25, 26, 29 and 30).

restriction enzymes, for example EcoRI and XbaI, for directional and non-directional cloning into the target vector. After PCR amplification and restriction digest with the appropriate restriction enzyme (usually XbaI), the cDNA fragments were cloned into the corresponding site in a modified pPZP binary vector (Hajdukiewicz et al., 1994). The pPZP221 vector was modified to contain the $35S^2$ cassette from pKYLX71:35 $S^2$ (Schardl et al., 1987) as follows: pKYLX71:35 $S^2$ was cut with ClaI. The 5' overhang was filled in using Klenow and the blunt end was A-tailed with Taq polymerase. After cutting with EcoRI, the 2 kb fragment with an EcoRI-compatible and a 3'-A tail was gel-purified. pPZP221 was cut with HindIII and the resulting 5' overhang filled in and T-tailed with Taq polymerase. The remainder of the original pPZP221 multi-cloning site was removed by digestion with EcoRI, and the expression cassette cloned into the EcoRI site and the 3' T overhang restoring the HindIII site. This binary vector contains between the left and right border the plant selectable marker gene aacC1 under the control of the 35S promoter and 35S terminator and the pKYLX71:35 $S^2$-derived expression cassette with a CaMV 35S promoter with a duplicated enhancer region and an rbcS terminator.

Alternatively, the primers for the amplification of cDNA fragments contained attB sequences for use with recombinases utilising the GATEWAY® system (Invitrogen). The resulting PCR fragments were used in a recombination reaction with pDONR® vector (Invitrogen) to generate entry vectors. A GATEWAY® cloning cassette (Invitrogen) was introduced into the multicloning site of the pPZP221:35 $S^2$ vector following the manufacturer's protocol. In a further recombination reaction, the cDNAs encoding the open read-

TABLE 2

List of primers used for sequencing of the full-length cDNAs of TrCHSa3, TrCHSc, TrCHSf, TrCHSh, TrLARa, TrLARb and TrLARc

| gene name | clone ID | sequencing primer | primer sequence (5' > 3') |
|---|---|---|---|
| TrCHSa3 | 05wc1RsB06 | 05wc1RsB06.f1 | AGGAGGCTGCAGTCAAGG |
| | | 05wc1RsB06.f2 | TGCCTGAAATTGAGAAACC |
| | | 05wc1RsB06.f3 | AAAGCTAGCCTTGAAGCC |
| TrCHSc | 07wc1TsE12 | 07wc1TsE12.f1 | TCGGACATAACTCATGTGG |
| | | 07wc1TsE12.f2 | TTGGGTTGGAGAATAAGG |
| | | 07wc1TsE12.r1 | TGGACATTTATTGGTTGC |
| | | 07wc1TsE12.r2 | TATCATGTCTGGAAATGC |
| TrCHSf | 07wc1UsD07 | 07wc1UsD07.f1 | AGATTGCATCAAAGAATGG |
| | | 07wc1UsD07.r1 | GGTCCAAAAGCCAATCC |
| TrCHSh | 13wc21sG04 | 13wc21sG04.f1 | TAAGACGAGACATAGTGG |
| | | 13wc21sG04.r1 | TATTCACTAAGCACATGC |
| TrLARa | 05wc1CsA02 | 05wc1CsA02.f1 | TCATTTCTGCAATAGGAGG |
| | | 05wc1CsA02.r1 | ATCCACCTCAGGTGAACC |
| TrLARb | 05wc3EsA03 | 05wc3EsA03.f1 | AATAGGAGGCTCTGATGG |
| | | 05wc3EsA03r1 | ATCCACCTCAGGTGAACC |
| TrLARc | 07wc1VsF06 | 07wc1VsF06.f1 | AGGCTCTGATGGCTTGC |
| | | 07wc1VsF06.r1 | ATCCACCTCAGGTGAACC |

EXAMPLE 4

Development of Binary Transformation Vectors Containing Chimeric Genes with cDNA Sequences from White Clover TrCHSa3, TrCHSc, TrCHSf, TrCHSh, TrBANa, TrLARa, TrLARb and TrLARc To alter the expression of the proteins involved in flavonoid biosynthesis, and more specifically condensed tannin biosynthesis to improve herbage quality and bloat-safety, a set of sense and antisense binary transformation vectors was produced.

cDNA fragments were generated by high fidelity PCR with a proofreading DNA polymerase using the original pGEM-T Easy plasmid cDNA as a template. The primers used (Table 3) contained recognition sites for appropriate ing frame sequences were transferred from the entry vector to the GATEWAY®-enabled pPZP221:35 S² vector.

The orientation of the constructs (sense or antisense) was checked by restriction enzyme digest and sequencing which also confirmed the correctness of the sequence. Transformation vectors containing chimeric genes using full-length open reading frame cDNAs encoding white clover TrCHSa3, TrCHSc, TrCHSf, TrCHSh, TrBANa, TrLARa, TrLARb and TrLARc proteins in sense and antisense orientation under the control of the CaMV 35S² promoter were generated (FIGS. 4, 8, 12, 16, 20, 24, 28 and 32).

TABLE 3

List of primers used to PCR-amplify the open reading frames

| gene name | primer | primer sequence (5' -> 3') |
|---|---|---|
| TrCHSa3 | 05wc1RsB06f | GAATTCTAGAAGATATGGTGAGTGTAGCTG |
|  | 05wc1RsB06r | GAATTCTAGAATCACACATCTTATATAGCC |
| TrCHSa3 | 05wc1RsB06fG | GGGGACAAGTTTGTACAAAAAAGCAGGCTTCTAGAAGATATGGTGAGTGTAGCTG |
|  | 05wc1RsB06rG | GGGGACCACTTTGTACAAGAAAGCTGGGTTCTAGAATCACACATCTTATATAGCC |
| TrCHSc | 07wc1TsE12f | GAATTCTAGAAGAAGAAATATGGGAGACGAAGG |
|  | 07wc1TsE12r | GAATTCTAGAAAGACTTCATGCACACAAGTTCC |
| TrCHSf | 07wc1UsD07f | GAATTCTAGATGATTCATTGTTTGTTTCCATAAC |
|  | 07wc1UsD07r | GAATTCTAGAACATATTCATCTTCCTATCAC |
| TrCHSh | 13wc21sG04f | GAATTCTAGATCCAAATTCTCGTACCTCACC |
|  | 13wc21sG04r | GAATTCTAGATAGTTCACATCTCTCGGCAGG |
| TrBANa | 05wc2XsG02f | GGATCCTCTAGAGCACTAGTGTGTATAAGTTTCTTGG |
|  | 05wc2XsG02r | GGATCCTCTAGACCCCCTTAGTCTTAAAATACTCG |
| TrLARa | 05wc1CsA02fG | GGGGACAAGTTTGTACAAAAAAGCAGGCTCTAGAAAGCAAAGCAATGGCACC |
|  | 05wc1CsA02rG | GGGGACCACTTTGTACAAGAAAGCTGGGTCTAGATCCACCTCAGGTGAACC |
| TrLARb | 05wc3EsA03fG | GGGGACAAGTTTGTACAAAAAAGCAGGCTCTAGAAAGCAATGGCACCAGCAGC |
|  | 05wc3EsA03rG | GGGGACCACTTTGTACAAGAAAGCTGGGTCTAGATCCACCTCAGGTGAACC |
| TrLARc | 07wc1VsF06fG | GGGGACAAGTTTGTACAAAAAAGCAGGCTCTAGATAAAGCAATGGCACCAGC |
|  | 07wc1VsF06rG | GGGGACCACTTTGTACAAGAAAGCTGGGTCTAGATCCACCTCAGGTGAACC |

The pPZP221:35 S² binary vector was further modified to contain two expression cassettes within one T-DNA. The expression cassette from the binary vector pWM5 consisting of the ASSU promoter and the tob terminator was PCR-amplified with a proofreading DNA polymerase using oligonucleotide primers with the following sequences:

```
forward primer   5'-CCACCATGTTTGAAATTTATTATGTGTTTT
                 TTTCCG-3';

reverse primer   5'-TAATCCCGGGTAAGGGCAGCCCATACAAAT
                 GAAGC-3'.
```

Figure 1:
FIG. 1 shows the plasmid map in pGEM-T Easy of TrCHSa3.
Figure 5:
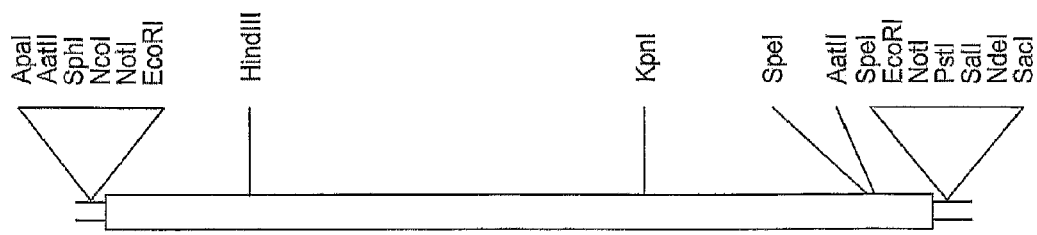
FIG. 5 shows the plasmid map in pGEM-T Easy of TrCHSc.
Figure 9:
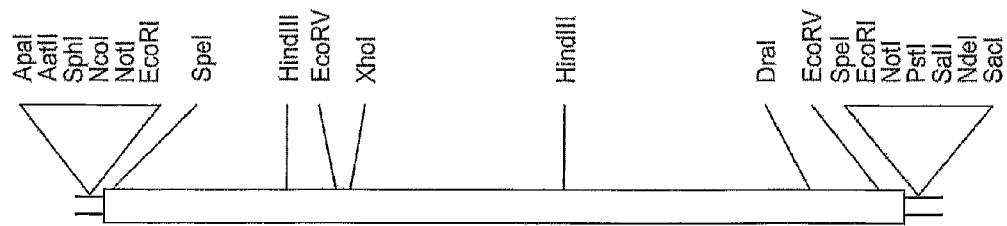
FIG. 9 shows the plasmid map in pGEM-T Easy of TrCHSf.
Figure 13:
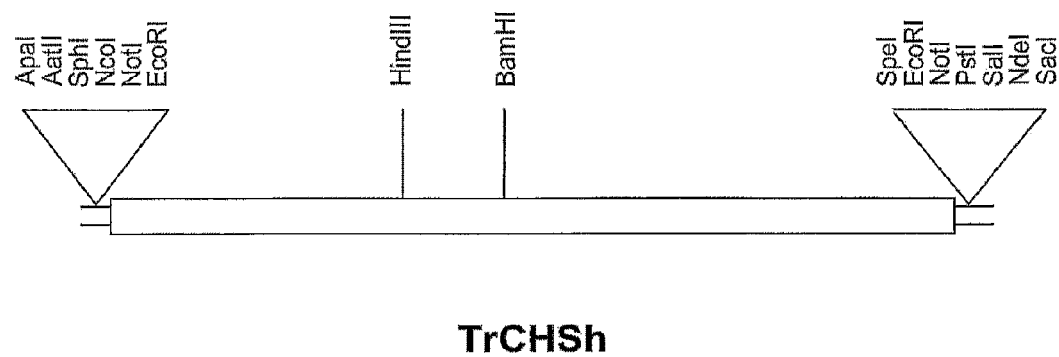
FIG. 13 shows the plasmid map in pGEM-T Easy of TrCHSh.
Figure 17:
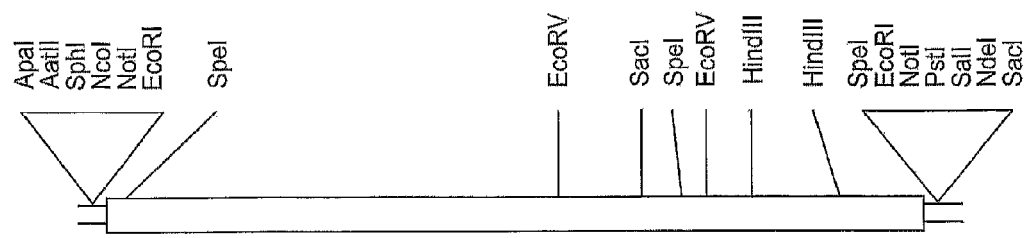
FIG. 17 shows the plasmid map in pGEM-T Easy of TrBANa.
Figure 21:
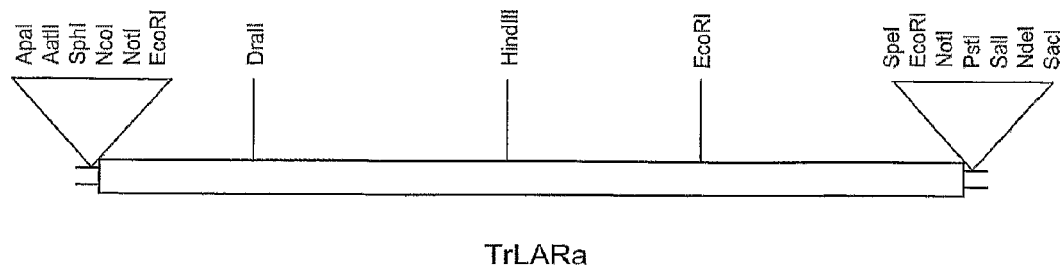
FIG. 21 shows the plasmid map in pGEM-T Easy of TrLARa.
Figure 25:
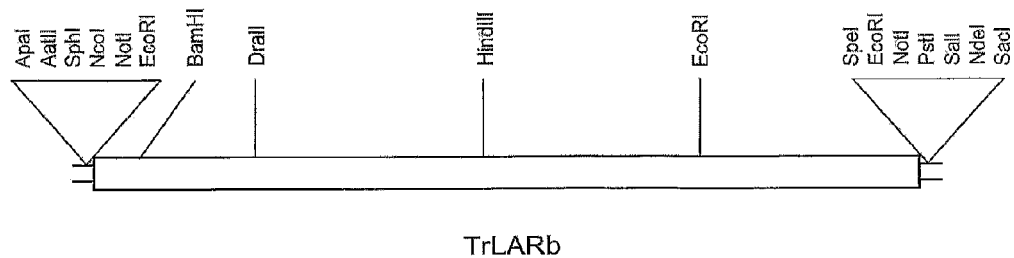
FIG. 25 shows the plasmid map in pGEM-T Easy of TrLARb.
Figure 28:
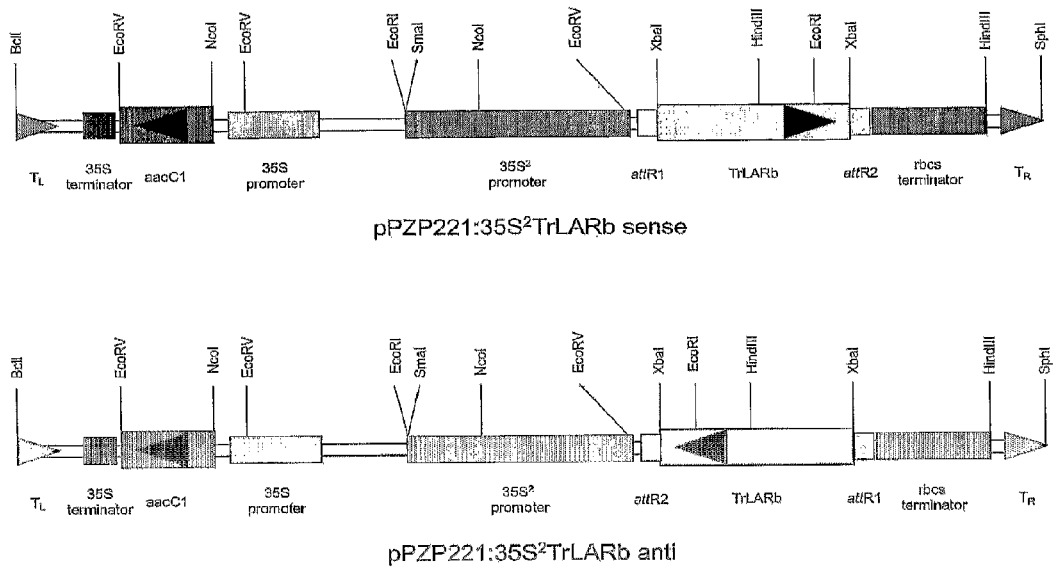
FIG. 28 shows plasmid maps of sense and antisense constructs of TrLARb in the binary vector pPZP221:35 $S^2$.
Figure 29:
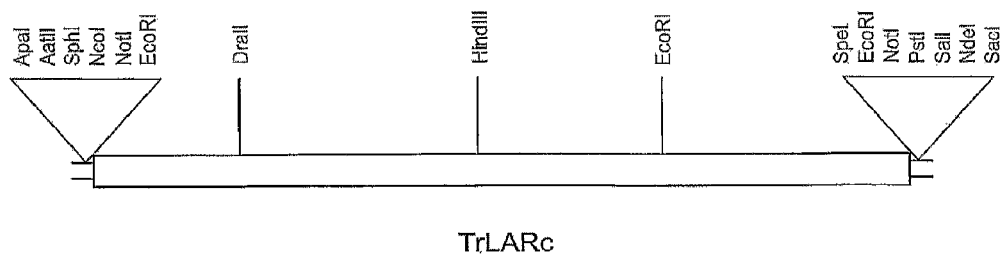
FIG. 29 shows the plasmid map in pGEM-T Easy of TrLARc.
Figure 33:
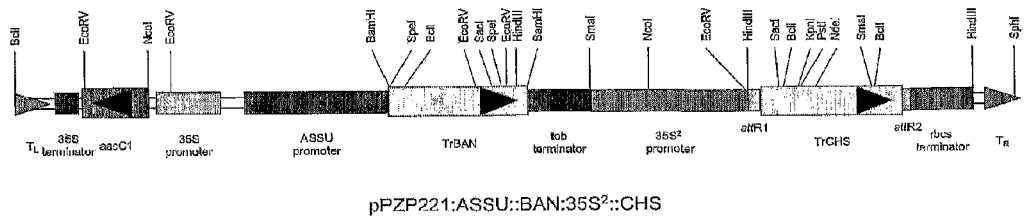
FIG. 33 shows the plasmid map of the binary vector pPZP221:ASSU::TrBAN:35$S^2$::TrCHS.

The PCR product was cut with BstXI and SmaI and cloned directionally into the equally cut pPZP221:35 S² vector. Additionally, a GATEWAY® cloning cassette (Invitrogen) was introduced into the multicloning site in the 35S²:rbcS expression cassette following the manufacturer's protocol. TrBANa was cloned into the ASSU:tob expression cassette, TrCHSa3 was amplified with the GATEWAY®-compatible primers (see Table 3) and cloned into the 35S²:rbcS expression cassette. A transformation vector containing chimeric genes using full-length open reading frame cDNAs encoding white clover TrBANa protein in sense orientation under the control of the ASSU promoter and TrCHSc3 protein in sense orientation under the control of the CaMV 35S² promoter within the same T-DNA was generated (FIG. 33).

EXAMPLE 5

Figure 34:
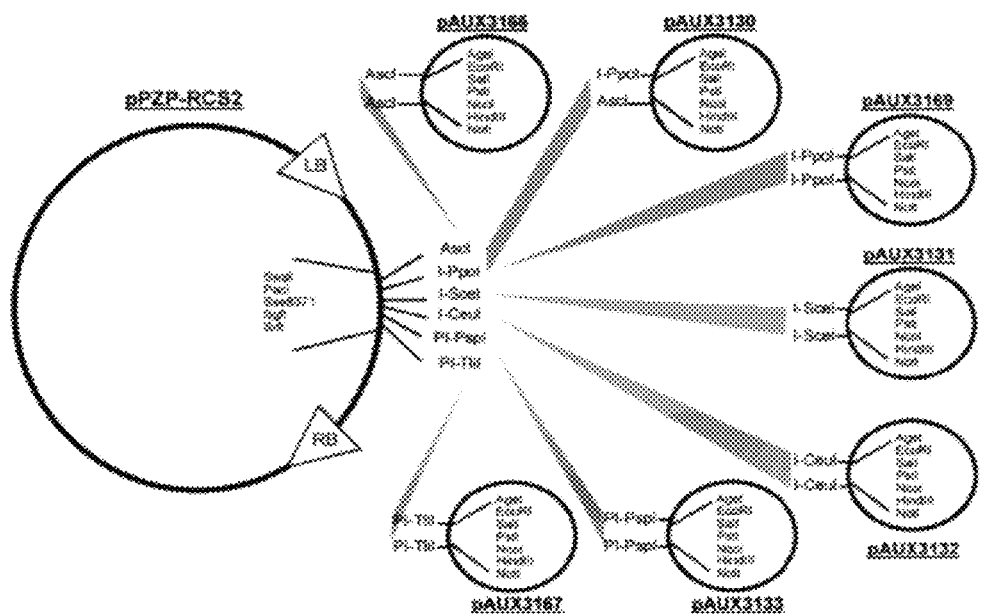
FIG. 34 shows the plasmid maps of the modular vector system comprising a binary base vector and 7 auxiliary vectors.

Development of Binary Transformation Vectors Containing Chimeric Genes with a Combination of 2 or More cDNA Sequences from White Clover TrCHSa3, TrCHSc, TrCHSf, TrCHSh, TrBANa, TrLARa, and TrLARc To alter the expression of the proteins involved in flavonoid biosynthesis, and more specifically condensed tannin biosynthesis to improve herbage quality and bloat-safety, a modular binary transformation vector system was used (FIG. 34). The modular binary vector system enables simultaneous integration of up to seven transgenes the expression of which is controlled by individual promoter and terminator sequences into the plant genome (Goderis et al., 2002).

The modular binary vector system consists of a pPZP200-derived vector (Hajdukiewicz et al., 1994) backbone containing within the T-DNA a number of unique restriction sites recognised by homing endonucleases. The same restriction sites are present in pUC18-based auxiliary vectors flanking standard multicloning sites. Expression cassettes comprising a selectable marker gene sequence or a cDNA sequence to be introduced into the plant under the control of regulatory sequences like promoter and terminator can be constructed in the auxiliary vectors and then transferred to the binary vector backbone utilising the homing endonuclease restriction sites. Up to seven expression cassettes can thus be integrated into a single binary transformation vector. The system is highly flexible and allows for any combination of cDNA sequence to be introduced into the plant with any regulatory sequence.

For example, a selectable marker cassette comprising the nos promoter and nos terminator regulatory sequences controlling the expression of the nptII gene was PCR-amplified using a proofreading DNA polymerase from the binary vector pKYLX71:35 S$^2$ and directionally cloned into the AgeI and NotI sites of the auxiliary vector pAUX3166. Equally, other selectable marker cassettes can be introduced into any of the auxiliary vectors.

In another example, the expression cassette from the binary vector pWM5 consisting of the ASSU promoter and the tob terminator was PCR-amplified with a proofreading DNA polymerase and directionally cloned into the AgeI and NotI sites of the auxiliary vector pAUX3169. Equally, other expression cassettes can be introduced into any of the auxiliary vectors.

In yet another example, the expression cassette from the direct gene transfer vector pDH51 was cut using EcoRI and cloned directly into the EcoRI site of the auxiliary vector pAUX3132.

TABLE 4

List of primers used to PCR-amplify plant selectable marker cassettes and the regulatory elements used to control the expression of TrCHSa3, TrCHSc, TrCHSf, TrCHSh, TrBANa, TrLARa, TrLARb and TrLARc genes

| expression cassette | primer | primer sequence (5' > 3') |
|---|---|---|
| nos::nptII-nos | forward | ATAATAACCGGTTGATCATGAGC GGAGAATTAAGGG |
|  | reverse | ATAATAGCGGCCGCTAGTAACAT AGATGACACCGCG |
| 35S::aacC1-35S | forward | AATAGCGGCCGCGATTTAGTACT GGATTTTGG |
|  | reverse | AATAACCGGTACCCACGAAGGAG CATCGTGG |
| 35S$^2$::rbcS | forward | ATAATAACCGGTGCCCGGGGATC TCCTTTGCC |
|  | reverse | ATAATAGCGGCCGCATGCATGTT GTCAATCAATTGG |
| assu::tob | forward | TAATACCGGTAAATTTATTATGR GTTTTTTTCCG |
|  | reverse | TAATGCGGCCGCTAAGGGCAGCC CATACAAATGAAGC |

Figure 35:
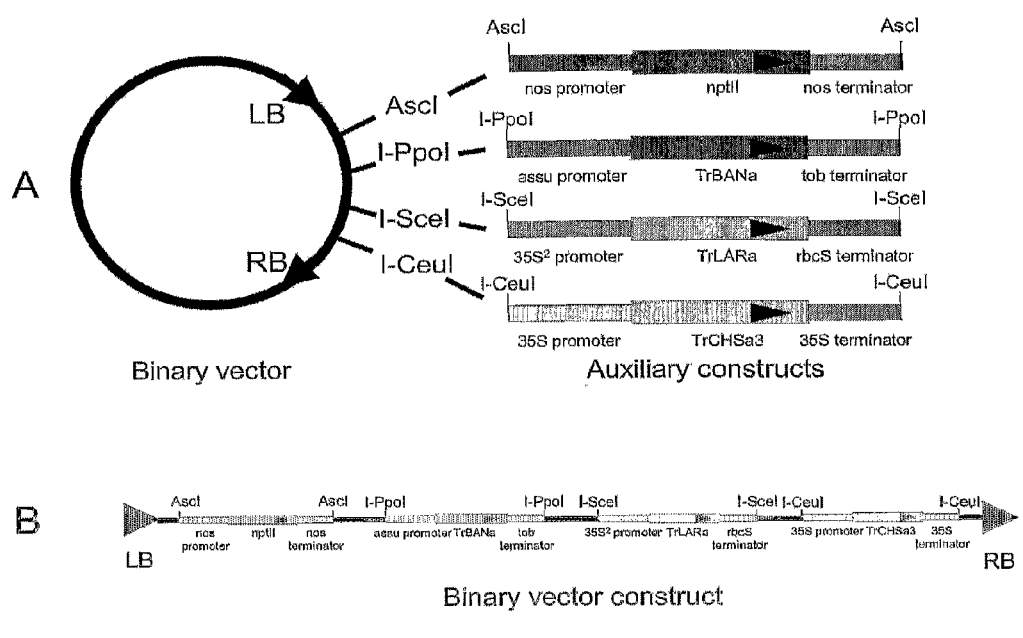
FIG. 35 shows an example of the modular binary transformation vector system comprising plasmid maps of the binary transformation vector backbone and 4 expression cassettes in auxiliary vectors (A) and the plasmid map of the T-DNA region of the final binary transformation vector.

The expression cassettes were further modified by introducing a GATEWAY® cloning cassette (Invitrogen) into the multicloning site of the respective pAUX vector following the manufacturer's protocol. In a recombination reaction, the cDNAs encoding the open reading frame sequences were transferred from the entry vector obtained as described in Example 4 to the GATEWAY®-enabled pAUX vector. Any combination of the regulatory elements with cDNA sequences of TrCHSa3, TrCHSc, TrCHSf, TrCHSh, TrBANa, TrLARa, TrLARb and TrLARc can be obtained. One typical example is given in FIG. 35 with expression cassettes for the nptII plant selectable marker, TrBANa, TrLARa and TrCHSa3.

Complete expression cassettes comprising any combination of regulatory elements and cDNA sequences to be introduced into the plant were then cut from the auxiliary vectors using the respective homing endonuclease and cloned into the respective restriction site on the binary vector backbone. After verification of the construct by nucleotide sequencing, the binary transformation vector comprising a number of expression cassettes was used to generate transgenic white clover plants.

EXAMPLE 6

Production by *Agrobacterium*-Mediated Transformation and Analysis of Transgenic White Clover Plants Carrying Chimeric White Clover TrCHSa3, TrCHSc, TrCHSf, TrCHSh, TrBANa, TrLARa, TrLARb and TrLARc Genes Involved in Flavonoid Biosynthesis A set of binary transformation vectors carrying chimeric white clover genes involved in flavonoid biosynthesis, and more specifically condensed tannin biosynthesis to improve herbage quality and bloat-safety, were produced as detailed in Examples 4 and 5.

*Agrobacterium*-mediated gene transfer experiments were performed using these transformation vectors.

The production of transgenic white clover plants carrying the white clover TrCHSa3, TrCHSc, TrCHSf, TrCHSh, TrBANa, TrLARa, TrLARb and TrLARc cDNAs, either singly or in combination, is described here in detail.

Preparation of *Agrobacterium*

*Agrobacterium tumefaciens* strain AGL-1 transformed with one of the binary vector constructs detailed in Example 6 were streaked on LB medium containing 50 μg/ml rifampicin and 50 μg/ml kanamycin and grown at 27° C. for 48 hours. A single colony was used to inoculate 5 ml of LB medium containing 50 μg/ml rifampicin and 50 μg/ml kanamycin and grown over night at 27° C. and 250 rpm on an orbital shaker. The overnight culture was used as an inoculum for 500 ml of LB medium containing 50 μg/ml kanamycin only. Incubation was over night at 27° C. and 250 rpm on an orbital shaker in a 2 l Erlenmeyer flask.

Preparation of White Clover Seeds 1 spoon of seeds (ca. 500) was placed into a 280 μm mesh size sieve and washed for 5 min under running tap water, taking care not to wash seeds out of sieve. In a laminar flow hood, seeds were transferred with the spoon into an autoclaved 100 ml plastic culture vessel. A magnetic stirrer (wiped with 70% EtOH) and ca. 30 ml 70% EtOH were added, and the seeds were stirred for 5 min. The EtOH was discarded and replaced by 50 ml 1.5% sodium hypochlorite. The seeds were stirred for an additional 45-60 min on a magnetic stirrer. The sodium hypochlorite was then discarded and the seeds rinsed 3 to 4 times with autoclaved ddH$_2$O. Finally 30 ml of ddH$_2$O were added, and seeds incubated over night at 10-15° C. in an incubator.

Agrobacterium-Mediated Transformation of White Clover

The seed coat and endosperm layer of the white clover seeds prepared as above were removed with a pair of 18 G or 21 G needles. The cotyledons were cut from the hypocotyl leaving a ca. 1.5 mm piece of the cotyledon stalk. The cotyledons were transferred to a petridish containing ddH$_2$O. After finishing the isolation of clover cotyledons, ddH$_2$O in the petridish was replaced with Agrobacterium suspension (diluted to an OD$_{600}$=0.2-0.4). The petridish was sealed with its lid and incubated for 40 min at room temperature.

After the incubation period, each cotyledon was transferred to paper towel using the small dissection needle, dried and plated onto regeneration medium RM73. The plates were incubated at 25° C. with a 16 h light/8 h dark photoperiod. On day 4, the explants were transferred to fresh regeneration medium. Cotyledons transformed with Agrobacterium were transferred to RM73 containing cefotaxime (antibacterial agent) and gentamycin. The dishes were sealed with Parafilm and incubated at 25° C. under a 16/8 h photoperiod. Explants were subcultured every three weeks for a total of nine weeks onto fresh RM 73 containing cefotaxime and gentamycin. Shoots with a green base were then transferred to root-inducing medium RIM. Roots developed after 1-3 weeks, and plantlets were transferred to soil when the roots were well established.

This process is shown in detail in FIG. 36.

Preparation of Genomic DNA for Real-Time PCR and Analysis for the Presence of Transgenes 3-4 leaves of white clover plants regenerated on selective medium were harvested and freeze-dried. The tissue was homogenised on a Retsch MM300 mixer mill, then centrifuged for 10 min at 1700×g to collect cell debris. Genomic DNA was isolated from the supernatant using Wizard Magnetic 96 DNA Plant System kits (Promega) on a Biomek FX (Beckman Coulter). 5 µl of the sample (50 µl) were then analysed on an agarose gel to check the yield and the quality of the genomic DNA.

Genomic DNA was analysed for the presence of the transgene by real-time PCR using SYBR Green chemistry. PCR primer pairs (Table 4) were designed using MacVector (Accelrys) or PrimerExpress (ABI). The forward primer was located within the 35S$^2$ promoter region and the reverse primer within the transgene to amplify products of approximately 150-250 bp as recommended. The positioning of the forward primer within the 35S$^2$ promoter region guaranteed that endogenous genes in white clover were not detected.

TABLE 5

List of primers used for Real-time PCR analysis of white clover plants transformed with chimeric white clover genes involved in condensed tannin biosynthesis

| construct | primer 1 (forward), 5' -> 3' | primer 2 (reverse), 5' -> 3' |
|---|---|---|
| pPZP221TrCHSa3 | CATTTCATTTGGAGAGGACACGC | AACACGGTTTGGTGGATTTGC |
| pPZP221TrCHSc | TTGGAGAGGACACGCTGAAATC | ACAAGTTGGTGAGGGAATGCC |
| pPZP221TrCHSf | CATTTCATTTGGAGAGGACACGC | TCGTTGCCTTTCCCTGAGTAGG |
| pPZP221TrCHSh | TCATTTGGAGAGGACACGCTG | CGGTCACCATTTTTTGTTGGAGG |
| pPZP221TrBANa | TTGGAGAGGACACGCTGAAATC | CAACAAAACCAGTGCCACC |
| pPZP221TrLARa | ATGACGCACAATCCCACTATCC | AGCCTTAGAAGAGAGAAGAGGTCC |
| pPZP221TrLARb | ATGACGCACAATCCCACTATCC | AGCCTTAGAAGAGAGAAGAGGTCC |
| pPZP221TrLARc | ATGACGCACAATCCCACTATCC | AGCCTTAGAAGAGAGAAGAGGTCC |

5 µl of each genomic DNA sample was run in a 50 µl PCR reaction including SYBR Green on an ABI 7700 (Applied Biosystems) together with samples containing DNA isolated from wild type white clover plants (negative control), samples containing buffer instead of DNA (buffer control) and samples containing the plasmid used for transformation (positive plasmid control). Cycling conditions used were 2 min. at 50° C., 10 min. at 95° C. and then 40 cycles of 15 sec. at 95° C., 1 min. at 60° C.

Preparation of Genomic DNA and Analysis of DNA for Presence and Copy Number of Transgene by Southern Hybridisation Blotting Genomic DNA for Southern hybridisation blotting was obtained from leaf material of white clover plants following the CTAB method. Southern hybridisation blotting experiments were performed following standard protocols as described in Sambrook et al. (1989). In brief, genomic DNA samples were digested with appropriate restriction enzymes and the resulting fragments separated on an agarose gel. After transfer to a membrane, a cDNA fragment representing a transgene or selectable marker gene was used to probe the size-fractionated DNA fragments. Hybridisation was performed with either radioactively labelled probes or using the non-radioactive DIG labelling and hybridisation protocol (Boehringer) following the manufacturer's instructions.

Plants were obtained after transformation with all chimeric constructs and selection on medium containing gentamycin. Details of plant analysis are given in Table 5 and FIGS. 37, 38 and 39.

TABLE 5

Transformation of white clover with binary transformation vectors comprising cDNAs of white clover genes involved in condensed tannin biosyntheses, selection and molecular analysis of regenerated plants.

| construct | cotyledons transformed | selection into RIM | soil | QPCR-positive | Southern | copy number range |
|---|---|---|---|---|---|---|
| pPZP221-35S2::TrCHSa3 | 2358 | 135 | 32 | 23 | n/d | |
| pPZP221-35S2::TrCHSc | 3460 | 89 | 41 | 27 | n/d | |
| pPZP221-35S2::TrCHSf | 3931 | 113 | 44 | 27 | n/d | |
| pPZP221-35S2::TrCHSh | 3743 | 79 | 37 | 30 | n/d | |
| pPZP221-35S2::TrBANa | 2315 | 144 | 50 | 38 | 7 | 1 to 4 |
| pPZP221-35S2::TrLARa | 2487 | 88 | 45 | 38 | n/d | |
| pPZP221-35S2::TrLARb | 3591 | 133 | 47 | 47 | 5 | 1 to 3 |
| pPZP221-35S2::TrLARc | 2835 | 96 | 32 | 29 | n/d | |

REFERENCES

Altschul, S. F., Gish, W., Miller, W., Myers, E. W., Lipman, D. J. (1990) "Basic local alignment search tool." J. Mol. Biol. 215, 403-410.

Frohman, M. A., Dush, M. K., Martin, G. R. (1988) Rapid production of full-length cDNAs from rare transcripts: amplification using a single gene-specific oligonucleotide primer. Proc. Natl. Acad. Sci. USA 85, 8998.

Gish, W., States, D. J. (1993) Identification of protein coding regions by database similarity search. Nature Genetics 3, 266-272.

Goderis, I., De Bolle, M. F. C., Francois, I., Wouters, P. F. J., Broekaert, W. F., and Cammue, B. P. A. (2002) A set of modular plant transformation vectors allowing flexible insertion of up to six expression units. Plant Molecular Biology 50, 17-27.

Hajdukiewicz P, Svab Z, Maliga P. (1994) The small, versatile pPZP family of Agrobacterium binary vectors for plant transformation. Plant Mol Biol. 25, 989-94.

Loh, E. Y., Elliott, J. F., Cwirla, S., Lanier, L. L., Davis, M. M. (1989). Polymerase chain reaction with single-sided specificity: Analysis of T-cell receptor delta chain. Science 243, 217-220.

Ohara, O., Dorit, R. L., Gilbert, W. (1989). One-sided polymerase chain reaction: The amplification of cDNA. Proc. Natl. Acad Sci USA 86, 5673-5677

Sambrook, J., Fritsch, E. F., Maniatis, T. (1989). Molecular Cloning. A Laboratory Manual. Cold Spring Harbour Laboratory Press Schardl, C. L., Byrd, A. D., Benzion, G., Altschuler, M. A., Hildebrand, D. F., Hunt, A. G. (1987) Design and construction of a versatile system for the expression of foreign genes in plants. Gene 61, 1-11

Finally, it is to be understood that various alterations, modifications and/or additions may be made without departing from the spirit of the present invention as outlined herein.

The invention claimed is:

1. A purified or isolated nucleic acid comprising
(a) a sequence encoding a leucoanthocyanidine reductase (LAR) comprising a nucleic acid sequence selected from the group consisting of SEQ ID NOs: 11, 13, and 15, or
(b) a variant of the sequence of paragraph (a), wherein the variant has at least 80% nucleic acid identity to any one of SEQ ID NOs: 11, 13 or 15, and encodes a polypeptide comprising the entirety of SEQ ID NOs: 12, 14, or 16, respectively.

2. The purified or isolated nucleic acid of claim 1, wherein the nucleic acid is a variant and the variant has at least 95% nucleic acid identity to any one of SEQ ID NOs: 11, 13 or 15.

3. The purified or isolated nucleic acid of claim 1, comprising a sequence selected from the group consisting of SEQ ID NOs: 11, 13 and 15 as the sequence encoding the LAR.

4. The purified or isolated nucleic acid of claim 1, further comprising a promoter sequence effective to direct expression of the nucleic acid sequence of (a), or (b) in a plant cell.

5. A plant cell, plant, plant seed or other plant part, comprising a nucleic acid construct, said construct comprising
a nucleic acid sequence selected from the group consisting of:
(a) a sequence encoding a leucoanthocyanidine reductase (LAR) comprising a nucleic acid sequence selected from the group consisting of SEQ ID NOs: 11, 13, and 15, and
(b) a variant of the sequence of paragraph (a), wherein the variant has at least 80% nucleic acid identity to any one of SEQ ID NOs: 11, 13 or 15, and encodes a polypeptide comprising the entirety of SEQ ID NOs: 12, 14, or 16, respectively; and
a promoter sequence heterologous to the nucleic acid sequence effective to direct expression of the nucleic acid sequence in the plant cell, plant, plant seed or other plant part.

6. A method for modifying one or more processes selected from the group consisting of condensed tannin biosynthesis; protein binding; metal chelation; anti oxidation; UV-light absorption; and plant defense to a biotic stress in a plant, said method comprising
introducing into said plant an effective amount of a purified or isolated nucleic acid sequence comprising a sequence selected from the group consisting of:
(a) a sequence encoding a leucoanthocyanidine reductase (LAR) comprising a nucleic acid sequence selected from the group consisting of SEQ ID NOs: 11, 13, and 15, and
(b) a variant of the sequence of paragraph (a), wherein the variant has at least 80% nucleic acid identity to any one of SEQ ID NOs: 11, 13 or 15, and encodes a polypeptide comprising the entirety of SEQ ID NO: 12, 14, or 16, respectively; and
expressing the nucleic acid sequence in the plant, whereby at least one of the processes is modified.

7. A method of modifying forage quality of a plant by disrupting protein foam and/or conferring protection from rumen pasture bloat, said method comprising
introducing into said plant an effective amount of a purified or isolated nucleic acid sequence comprising a sequence selected from the group consisting of:
(a) a sequence encoding a leucoanthocyanidine reductase (LAR) comprising a nucleic acid sequence selected from the group consisting of SEQ ID NOs: 11, 13, and 15, and
(b) a variant of the sequence of paragraph (a), wherein the variant has at least 80% nucleic acid identity to any one of SEQ ID NOs: 11, 13 or 15, and encodes a polypeptide having LAR activity, and having at least 95% amino acid identity to SEQ ID NO: 12, 14, or 16, respectively; and
expressing the nucleic acid sequence in the plant, whereby the forage quality of the plant is modified.

* * * * *